United States Patent
Yee et al.

(10) Patent No.: US 11,766,539 B2
(45) Date of Patent: Sep. 26, 2023

(54) ENHANCED FLEXIBILITY NEUROVASCULAR CATHETER

(71) Applicant: INCEPT, LLC, Lexington, MA (US)

(72) Inventors: Brandon Yee, Oakland, CA (US); Ashoor Shahbazi Yourgenlow, San Jose, CA (US); Yi Yang, San Francisco, CA (US); Farhad Khosravi, Los Altos Hills, CA (US); Joseph Rimsa, Palo Alto, CA (US)

(73) Assignee: INCEPT, LLC, Lexington, MA (US)

( * ) Notice: Subject to any disclaimer, the term of this patent is extended or adjusted under 35 U.S.C. 154(b) by 593 days.

(21) Appl. No.: 16/833,585

(22) Filed: Mar. 28, 2020

(65) Prior Publication Data
US 2020/0306501 A1 Oct. 1, 2020

Related U.S. Application Data

(60) Provisional application No. 62/826,203, filed on Mar. 29, 2019.

(51) Int. Cl.
*A61M 25/00* (2006.01)
*A61M 25/01* (2006.01)
*A61B 17/22* (2006.01)

(52) U.S. Cl.
CPC .... *A61M 25/0012* (2013.01); *A61M 25/0013* (2013.01); *A61B 17/22031* (2013.01);
(Continued)

(58) Field of Classification Search
CPC ........ A61M 2025/0047; A61M 25/005; A61M 25/0053; A61M 25/0054; A61M 25/0012; A61M 25/0013
See application file for complete search history.

(56) References Cited

U.S. PATENT DOCUMENTS

| 4,030,503 A | 6/1977 | Clark, III |
| 4,319,580 A | 3/1982 | Colley et al. |

(Continued)

FOREIGN PATENT DOCUMENTS

| CN | 101123918 A | 2/2008 |
| CN | 101252958 A | 8/2008 |

(Continued)

OTHER PUBLICATIONS

U.S. Appl. No. 15/862,488 (U.S. Pat. No. 10,653,426), filed Jan. 4, 2018, Thromboresistant Coatings for Aneurysm Treatment Devices.

(Continued)

*Primary Examiner* — Christopher J Besler
(74) *Attorney, Agent, or Firm* — Knobbe, Martens Olson & Bear, LLP

(57) ABSTRACT

A catheter is provided comprising localized regions of modified flexibility. The regions of modified flexibility may comprise a softened inner liner, for example softened via stretching the inner liner or disposing a plurality of holes in the inner liner, to modify the bending stiffness and/or tensile stiffness of the catheter. The catheter may further include an axially extending filament that at least partially overlaps the softened portion of the inner liner. The axially extending filament may include an anchoring section to anchor the at least one axially extending filament in a section of the catheter that includes the helical coil.

26 Claims, 42 Drawing Sheets

(52) U.S. Cl.
CPC .... *A61B 2217/005* (2013.01); *A61M 25/0147* (2013.01); *A61M 2205/0266* (2013.01)

(56) References Cited

U.S. PATENT DOCUMENTS

| | | | |
|---|---|---|---|
| 4,611,594 A | 9/1986 | Grayhack et al. |
| 4,619,274 A | 10/1986 | Morrison et al. |
| 4,762,129 A | 8/1988 | Bonzel |
| 4,762,130 A | 8/1988 | Fogarty et al. |
| 4,810,582 A | 3/1989 | Gould et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,234,416 A | 8/1993 | Macaulay et al. |
| 5,243,997 A | 9/1993 | Uflacker |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,536,242 A | 7/1996 | Willard et al. |
| 5,549,119 A | 8/1996 | Solar |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,713,848 A | 2/1998 | Dubrul et al. |
| 5,766,191 A | 6/1998 | Trerotola |
| 5,776,141 A | 7/1998 | Klein et al. |
| 5,792,124 A | 8/1998 | Horrigan et al. |
| 5,827,242 A | 10/1998 | Follmer |
| 5,843,103 A | 12/1998 | Wulfman |
| 5,885,209 A | 3/1999 | Green |
| 5,891,114 A | 4/1999 | Chien et al. |
| 5,895,398 A | 4/1999 | Wensel |
| 5,899,892 A | 5/1999 | Mortier et al. |
| 5,916,192 A | 6/1999 | Nita et al. |
| 5,935,112 A | 8/1999 | Stevens |
| 5,951,539 A | 9/1999 | Nita |
| 6,007,530 A | 12/1999 | Dornhofer et al. |
| 6,090,118 A | 7/2000 | McGuckin, Jr. |
| 6,143,009 A | 11/2000 | Shiber |
| 6,152,909 A | 11/2000 | Bagaoisan et al. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates |
| 6,197,014 B1 | 3/2001 | Samson et al. |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal |
| 6,355,027 B1 | 3/2002 | Le et al. |
| 6,394,976 B1 | 5/2002 | Winston et al. |
| 6,451,036 B1 | 6/2002 | Heitzmann |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth |
| 6,524,303 B1 | 2/2003 | Garibaldi et al. |
| 6,520,934 B1 | 3/2003 | Lee |
| 6,533,751 B2 | 3/2003 | Cragg |
| 6,554,820 B1 | 4/2003 | Wendlandt |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,663,613 B1 | 12/2003 | Evans et al. |
| 6,666,874 B2 | 12/2003 | Heitzmann |
| 6,669,670 B1 | 12/2003 | Muni et al. |
| 6,824,550 B1 | 11/2004 | Pintor et al. |
| 6,824,553 B1 | 11/2004 | Samson et al. |
| 6,929,633 B2 | 8/2005 | Evans et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,572 B2 | 2/2007 | Diamond et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas |
| 7,229,461 B2 | 6/2007 | Chin et al. |
| 7,232,452 B2 | 6/2007 | Adams et al. |
| 7,235,088 B2 | 6/2007 | Pintor et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,335,216 B2 | 2/2008 | Bender |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,601,138 B2 | 10/2009 | Goebel et al. |
| 7,763,196 B2 | 7/2010 | Goebel et al. |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin |
| 7,905,891 B2 | 3/2011 | Self |
| 7,931,659 B2 | 4/2011 | Bose et al. |
| 7,938,820 B2 | 5/2011 | Webster et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel |
| 8,070,694 B2 | 12/2011 | Galdonik et al. |
| 8,084,246 B2 | 12/2011 | Hoon et al. |
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,298,591 B2 | 10/2012 | Srivastava et al. |
| 8,361,095 B2 | 1/2013 | Osborne |
| 8,366,735 B2 | 2/2013 | Bose et al. |
| 8,382,739 B2 | 2/2013 | Walak et al. |
| 8,394,078 B2 | 3/2013 | Torrance et al. |
| 8,460,312 B2 | 6/2013 | Bose et al. |
| 8,485,969 B2 | 7/2013 | Grayzel et al. |
| 8,517,955 B2 | 8/2013 | Keast |
| 8,535,293 B2 | 9/2013 | Faherty et al. |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |

(56) References Cited

U.S. PATENT DOCUMENTS

| | | |
|---|---|---|
| 8,684,963 B2 | 4/2014 | Qiu et al. |
| 8,696,698 B2 | 4/2014 | Chomas |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse |
| 8,876,854 B2 | 11/2014 | Christiansen et al. |
| 8,900,179 B2 | 12/2014 | Jenson et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,996,095 B2 | 3/2015 | Anderson et al. |
| 8,998,946 B2 | 4/2015 | Morero |
| 9,014,786 B2 | 4/2015 | Carmeli et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,199,064 B2 | 12/2015 | Morero |
| 9,220,878 B2 | 12/2015 | Kajii |
| 9,238,124 B2 | 1/2016 | Grayzel et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,345,856 B2 | 5/2016 | Witte |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,439,791 B2 | 9/2016 | Vong et al. |
| 9,446,216 B2 | 9/2016 | Olesky et al. |
| 9,451,884 B2 | 9/2016 | Palovich |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,854 B2 | 12/2016 | Mallaby |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,137 B2 | 5/2017 | Jenson et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,789,283 B2 | 10/2017 | Richter et al. |
| 9,801,643 B2 | 10/2017 | Hansen et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 9,913,960 B2 | 3/2018 | Blanchard et al. |
| 9,987,028 B2 | 6/2018 | Lowinger et al. |
| 9,999,355 B2 | 6/2018 | Kirenko |
| 10,010,698 B2 | 7/2018 | Watanabe et al. |
| 10,028,854 B2 | 7/2018 | Tatalovich et al. |
| 10,039,906 B2 | 8/2018 | Kume et al. |
| 10,070,878 B2 | 9/2018 | Ma |
| 10,086,169 B2 | 10/2018 | Grayzel et al. |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,207,077 B2 | 2/2019 | Griggin et al. |
| 10,213,582 B2 | 2/2019 | Garrison et al. |
| 10,219,814 B2 | 3/2019 | Feltyberger et al. |
| 10,238,833 B2 | 3/2019 | Christian et al. |
| 10,258,452 B2 | 4/2019 | Eckhouse et al. |
| 10,265,086 B2 | 4/2019 | Vale et al. |
| 10,271,864 B2 | 4/2019 | Greenhalgh et al. |
| 10,278,816 B2 | 5/2019 | Miller et al. |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,384,034 B2 | 8/2019 | Garrison et al. |
| 10,420,581 B2 | 9/2019 | Hehrlein et al. |
| 10,441,745 B2 | 10/2019 | Yang et al. |
| 10,456,552 B2 | 10/2019 | Goyal |
| 10,471,233 B2 | 11/2019 | Garrison et al. |
| 10,478,535 B2 | 11/2019 | Ogle |
| 10,499,944 B2 | 12/2019 | Mallaby |
| 10,524,814 B2 | 1/2020 | Chang et al. |
| 10,531,883 B1 | 1/2020 | Deville et al. |
| 10,569,049 B2 | 2/2020 | Garrison et al. |
| 10,646,239 B2 | 5/2020 | Garrison et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,695,159 B2 | 6/2020 | Hauser |
| 10,716,583 B2 | 7/2020 | Look et al. |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,856,898 B2 | 12/2020 | Matsushita et al. |
| 10,864,351 B2 | 12/2020 | Garrison et al. |
| 10,888,280 B2 | 1/2021 | Newberry |

(56) References Cited

U.S. PATENT DOCUMENTS

| | | |
|---|---|---|
| 10,905,850 B2 | 2/2021 | Christian et al. |
| 11,020,030 B2 | 6/2021 | Tao et al. |
| 11,065,018 B2 | 7/2021 | Buck et al. |
| 11,076,876 B2 | 8/2021 | Vale |
| 11,096,712 B2 | 8/2021 | Teigen et al. |
| 11,147,949 B2 * | 10/2021 | Yang ............... A61M 25/0009 |
| 11,197,683 B1 | 12/2021 | Teigen et al. |
| 11,207,497 B1 | 12/2021 | Yee et al. |
| 11,234,723 B2 | 2/2022 | Ogle |
| 11,253,277 B2 | 2/2022 | Buck et al. |
| 11,259,821 B2 | 3/2022 | Buck et al. |
| 11,318,282 B2 | 5/2022 | Garrison et al. |
| 11,337,712 B2 | 5/2022 | Teigen et al. |
| 11,395,665 B2 | 7/2022 | Yang et al. |
| 11,406,402 B2 | 8/2022 | Deville et al. |
| 11,439,799 B2 | 9/2022 | Buck et al. |
| 11,457,936 B2 | 10/2022 | Buck et al. |
| 11,464,528 B2 | 10/2022 | Brady et al. |
| 11,490,909 B2 | 11/2022 | Look et al. |
| 11,553,935 B2 | 1/2023 | Buck et al. |
| 11,565,082 B2 | 1/2023 | Yourgenlow |
| 2001/0031980 A1 | 10/2001 | Wensel et al. |
| 2001/0031981 A1 | 10/2001 | Evans |
| 2002/0016565 A1 | 2/2002 | Zadno-Azizi et al. |
| 2002/0026145 A1 | 2/2002 | Bagaoisan et al. |
| 2002/0091372 A1 | 7/2002 | Cragg |
| 2002/0156459 A1 | 10/2002 | Ye et al. |
| 2002/0156460 A1 | 10/2002 | Ye |
| 2002/0169467 A1 | 11/2002 | Heitzmann |
| 2002/0173812 A1 | 11/2002 | McGuckin et al. |
| 2002/0177800 A1 | 11/2002 | Bagaoisan et al. |
| 2002/0177899 A1 | 11/2002 | Eum et al. |
| 2002/0188314 A1 | 12/2002 | Anderson et al. |
| 2003/0071285 A1 | 4/2003 | Tsukernik |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153847 A1 | 8/2003 | Sandler et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1 | 10/2004 | Kellett |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell |
| 2005/0080400 A1 | 4/2005 | Corcoran et al. |
| 2005/0103332 A1 | 5/2005 | Gingles et al. |
| 2005/0124985 A1 | 6/2005 | Takayama et al. |
| 2005/0137680 A1 | 6/2005 | Ortiz et al. |
| 2005/0182386 A1 | 8/2005 | Aggerholm |
| 2005/0187570 A1 | 8/2005 | Nguyen et al. |
| 2006/0030835 A1 | 2/2006 | Sherman et al. |
| 2006/0064036 A1 | 3/2006 | Osborne et al. |
| 2006/0074401 A1 | 4/2006 | Ross |
| 2006/0089618 A1 | 4/2006 | McFerran et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0038225 A1 | 2/2007 | Osborne et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086051 A1 | 4/2008 | Voegele |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270800 A1 | 10/2009 | Spurchise et al. |
| 2009/0270888 A1 | 10/2009 | Patel |
| 2009/0275974 A1 | 11/2009 | Marchand et al. |
| 2009/0287190 A1 | 11/2009 | Shippert |
| 2009/0312699 A1 | 12/2009 | Pudelko |
| 2010/0023033 A1 | 1/2010 | Mauch et al. |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0077620 A1 | 3/2011 | deBeer |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0150147 A1 | 6/2012 | Leynov et al. |
| 2012/0179032 A1 | 7/2012 | Bromander et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0012924 A1 | 1/2013 | Davis et al. |
| 2013/0018318 A1 | 1/2013 | Ravichandran et al. |
| 2013/0018359 A1 | 1/2013 | Coyle |
| 2013/0030461 A1 | 1/2013 | Marks et al. |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0096551 A1 | 4/2013 | Govari et al. |
| 2013/0116701 A1 | 5/2013 | Wang et al. |
| 2013/0131499 A1 | 5/2013 | Chan et al. |
| 2013/0131641 A1 | 5/2013 | Jimenez et al. |
| 2013/0131710 A1 | 5/2013 | Carmeli |
| 2013/0144328 A1 | 6/2013 | Weber et al. |
| 2013/0158511 A1 | 6/2013 | Aggerholm et al. |
| 2013/0158578 A1 | 6/2013 | Ghodke et al. |
| 2014/0025043 A1 | 1/2014 | Wang et al. |
| 2014/0039461 A1 | 2/2014 | Anderson et al. |
| 2014/0046243 A1 | 2/2014 | Ray et al. |
| 2014/0046244 A1 | 2/2014 | Ray et al. |

(56) References Cited

U.S. PATENT DOCUMENTS

| | | |
|---|---|---|
| 2014/0074144 A1 | 3/2014 | Shrivastava et al. |
| 2014/0100531 A1 | 4/2014 | Ankrum et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0200608 A1 | 7/2014 | Brady et al. |
| 2014/0228808 A1 | 8/2014 | Webster et al. |
| 2014/0243882 A1 | 8/2014 | Ma |
| 2014/0249508 A1 | 9/2014 | Wang et al. |
| 2014/0271718 A1 | 9/2014 | Alvarez |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0173782 A1 | 6/2015 | Garrison et al. |
| 2015/0174363 A1 | 6/2015 | Sutermeister et al. |
| 2015/0174368 A1 | 6/2015 | Garrison et al. |
| 2015/0257659 A1 | 9/2015 | Broers et al. |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Caprio |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0058513 A1 | 3/2016 | Giorgi |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206216 A1 | 7/2016 | Kirenko |
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0000576 A1 | 1/2017 | Zirps |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143416 A1 | 5/2017 | Guler et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0238953 A1 | 8/2017 | Yang et al. |
| 2017/0246014 A1 | 8/2017 | Rapaport et al. |
| 2017/0252057 A1 | 9/2017 | Bonnette et al. |
| 2017/0252536 A1* | 9/2017 | Yang ............... B29C 41/14 |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0333000 A1 | 11/2017 | Nystrom et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055364 A1 | 3/2018 | Pierro |
| 2018/0055516 A1 | 3/2018 | Bagaoisan et al. |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0207412 A1 | 7/2018 | Malek |
| 2018/0228502 A1 | 8/2018 | Shaffer |

(56) References Cited

U.S. PATENT DOCUMENTS

| | | |
|---|---|---|
| 2018/0242962 A1 | 8/2018 | Walen et al. |
| 2018/0242980 A1 | 8/2018 | Lubock |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0304040 A1* | 10/2018 | Jalgaonkar ........ A61M 25/0052 |
| 2019/0022363 A1 | 1/2019 | Grayzel et al. |
| 2019/0029825 A1 | 1/2019 | Fitterer et al. |
| 2019/0070387 A1 | 3/2019 | Goyal |
| 2019/0105477 A1 | 4/2019 | Heilman |
| 2019/0105478 A1 | 4/2019 | Malek |
| 2019/0108540 A1 | 4/2019 | Look et al. |
| 2019/0167124 A1 | 6/2019 | Verkruijsse et al. |
| 2019/0175030 A1 | 6/2019 | Verkruijsse et al. |
| 2019/0183517 A1 | 6/2019 | Ogle |
| 2019/0200871 A1 | 7/2019 | De Haan |
| 2019/0239910 A1 | 8/2019 | Brade et al. |
| 2019/0269368 A1 | 9/2019 | Hauck et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0336149 A1 | 11/2019 | Yang |
| 2019/0336727 A1 | 11/2019 | Yang |
| 2019/0351182 A1 | 11/2019 | Chou et al. |
| 2019/0366041 A1 | 12/2019 | Yang |
| 2019/0381221 A1 | 12/2019 | Ogle |
| 2019/0381223 A1 | 12/2019 | Culbert et al. |
| 2020/0001046 A1 | 1/2020 | Yang |
| 2020/0008820 A1 | 1/2020 | Aboytes et al. |
| 2020/0009301 A1 | 1/2020 | Yee |
| 2020/0009350 A1 | 1/2020 | Goyal |
| 2020/0015840 A1 | 1/2020 | Mallaby |
| 2020/0022712 A1 | 1/2020 | Deville et al. |
| 2020/0023160 A1 | 1/2020 | Chou et al. |
| 2020/0155181 A1 | 5/2020 | Yang |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0188630 A1 | 6/2020 | Fujita et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297362 A1 | 9/2020 | Deville et al. |
| 2020/0297972 A1 | 9/2020 | Yee |
| 2020/0323535 A1 | 10/2020 | Yang |
| 2020/0337716 A1 | 10/2020 | Garrison et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0397957 A1 | 12/2020 | Teigen et al. |
| 2021/0045622 A1 | 2/2021 | Petroff et al. |
| 2021/0045758 A1 | 2/2021 | Garrison et al. |
| 2021/0052296 A1 | 2/2021 | Garrison |
| 2021/0068852 A1 | 3/2021 | Spence |
| 2021/0069467 A1 | 3/2021 | Garrison et al. |
| 2021/0093336 A1 | 4/2021 | Roue |
| 2021/0106238 A1 | 4/2021 | Strasser |
| 2021/0106792 A1 | 4/2021 | Rafiee |
| 2021/0128182 A1 | 5/2021 | Teigen et al. |
| 2021/0146094 A1 | 5/2021 | Christian et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0228844 A1 | 7/2021 | Ogle |
| 2021/0315598 A1 | 10/2021 | Buck et al. |
| 2021/0316127 A1 | 10/2021 | Buck et al. |
| 2021/0353314 A1 | 11/2021 | Porter et al. |
| 2021/0361366 A1 | 11/2021 | Murphy et al. |
| 2022/0096104 A1 | 3/2022 | Ogle |
| 2022/0151646 A1 | 5/2022 | Dholakia et al. |
| 2022/0218365 A1 | 7/2022 | Deville et al. |
| 2022/0218366 A1 | 7/2022 | Deville et al. |
| 2022/0240959 A1 | 8/2022 | Quick |
| 2022/0280753 A1 | 9/2022 | Garrison et al. |
| 2022/0331085 A1 | 10/2022 | Buck et al. |
| 2022/0331509 A1 | 10/2022 | Buck et al. |
| 2022/0346814 A1 | 11/2022 | Quick |
| 2023/0015259 A1 | 1/2023 | Buck et al. |
| 2023/0061728 A1 | 3/2023 | Davis et al. |
| 2023/0064188 A1 | 3/2023 | Davis et al. |
| 2023/0069826 A1 | 3/2023 | Keating et al. |
| 2023/0093602 A1 | 3/2023 | Higgins et al. |

FOREIGN PATENT DOCUMENTS

| | | |
|---|---|---|
| CN | 101321552 A | 12/2008 |
| CN | 101340849 A | 1/2009 |
| CN | 101795631 A | 8/2010 |
| CN | 201596219 U | 10/2010 |
| CN | 102159146 | 8/2011 |
| CN | 102205161 | 10/2011 |
| CN | 102319097 A | 1/2012 |
| CN | 102573701 A | 7/2012 |
| CN | 102844071 A | 12/2012 |
| CN | 102847220 A | 1/2013 |
| CN | 203263993 U | 11/2013 |
| CN | 103648574 A | 3/2014 |
| CN | 103764214 A | 4/2014 |
| CN | 204158457 U | 2/2015 |
| CN | 104548316 A | 4/2015 |
| CN | 104622538 A | 5/2015 |
| CN | 104884117 | 9/2015 |
| CN | 104918578 | 9/2015 |
| CN | 105120776 A | 12/2015 |
| CN | 105208945 | 12/2015 |
| CN | 105208951 A | 12/2015 |
| CN | 204909516 U | 12/2015 |
| CN | 107405159 A | 11/2017 |
| DE | 10 2010 053111 | 6/2012 |
| DE | 10 2012 112732 | 6/2014 |
| EP | 0 330 843 | 12/1993 |
| EP | 0 309 471 | 8/1996 |
| EP | 1 349 486 | 3/2008 |
| EP | 2 069 528 | 3/2013 |
| EP | 2 937 108 | 10/2015 |
| EP | 2 928 360 | 1/2017 |
| EP | 3 539 486 | 9/2019 |
| JP | 2002-535049 | 10/2002 |
| JP | 2006-087643 | 4/2006 |
| JP | 2006-102222 | 4/2006 |
| JP | 2013-504388 | 2/2013 |
| WO | WO 95/009659 | 4/1995 |
| WO | WO 00/000100 | 1/2000 |
| WO | WO 2004/008974 | 1/2004 |
| WO | WO 2006/101170 | 9/2006 |
| WO | WO 2009/054968 | 4/2009 |
| WO | WO 09/125575 | 10/2009 |
| WO | WO 09/132218 | 10/2009 |
| WO | WO 2012/052159 | 4/2012 |
| WO | WO 2014/151209 | 9/2014 |
| WO | WO 2016/001712 | 1/2016 |
| WO | WO 2017/025775 | 2/2017 |
| WO | WO 18/121363 | 7/2018 |
| WO | WO 18/169032 | 9/2018 |
| WO | WO 2019/178165 | 9/2019 |
| WO | WO 2019/222518 | 11/2019 |
| WO | WO 2019/246583 | 12/2019 |
| WO | WO 2021/064955 | 4/2021 |
| WO | WO 2021/090821 | 5/2021 |
| WO | WO 2021/105658 | 6/2021 |

OTHER PUBLICATIONS

U.S. Appl. No. 16/863,723, filed Apr. 30, 2020, Thromboresistant Coatings for Aneurysm Treatment Devices.

(56) References Cited

OTHER PUBLICATIONS

U.S. Appl. No. 15/442,393 (U.S. Pat. No. 10,183,145), filed Feb. 24, 2017, Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841 (U.S. Pat. No. 10,661,053), filed Feb. 27, 2017, Method of Pulsatile Neurovascular Aspiration With Telescoping Catheter.
U.S. Appl. No. 15/443,838 (U.S. Pat. No. 10,179,224), filed Feb. 27, 2017, Enhanced Flexibility Neurovascular Catheter With Tensile Support.
U.S. Appl. No. 15/443,877 (U.S. Pat. No. 10,183,146), filed Feb. 27, 2017, Method of Making an Enhanced Flexibility Neurovascular Catheter.
U.S. Appl. No. 15/443,948 (U.S. Pat. No. 10,441,745), filed Feb. 27, 2017, Neurovascular Catheter With Enlargeable Distal End.
U.S. Appl. No. 16/542,657, filed Aug. 16, 2019, Method of Making an Enhanced Flexibility Neurovascular Catheter.
U.S. Appl. No. 15/444,038 (U.S. Pat. No. 10,183,147), filed Feb. 27, 2017, Neurovascular Catheter Extension Segment.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263, filed May 1, 2019, Neurovascular Catheter Having Atraumatic Angled Tip.
U.S. Appl. No. 16/570,084, filed Sep. 13, 2019, Enhanced Flexibility Neurovascular Catheter With Tensile Support.
U.S. Appl. No. 16/683,718 (U.S. Pat. No. 10,653,434), filed Nov. 14, 2019, Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 16/589,563, filed Oct. 1, 2019, Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832, filed Oct. 14, 2020, Systems and Methods for Multivariate Stroke Detection.
U.S. Appl. No. 16/728,469, filed Dec. 27, 2019, Neurovascular Access With Dynamic Assistance.
U.S. Appl. No. 17/125,723, filed Dec. 17, 2020, Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743, filed Dec. 17, 2020, Systems for Accessing a Central Pulmonary Artery.
U.S. Appl. No. 17/125,742, filed Dec. 17, 2020, Methods and Systems for Accessing and Retrieving Thrombo-Emboli.
Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/802,317, filed Feb. 26, 2020, Catheter With Seamless Flexibility Transistions.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/357,490, filed Jun. 24, 2021, Catheter System for Treating Thromboembolic Disease.
U.S. Appl. No. 17/357,558, filed Jun. 24, 2021, Aspiration System With Accelerated Response.
U.S. Appl. No. 17/357,643, filed Jun. 24, 2021, Hemostasis Valve.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/343,004, filed Jun. 9, 2021, Catheter With Enhanced Tensile Strength.
U.S. Appl. No. 15/443,874, filed Feb. 27, 2017, Telescoping Neurovascular Catheter With Enlargeable Distal Opening.
U.S. Appl. No. 16/398,626, filed Apr. 30, 2019, Devices and Methods for Removing Obstructive Material From an Intravascular Site.
U.S. Appl. No. 16/863,723, Apr. 30, 2020, Thromboresistant Coatings for Aneurysm Treatment Devices.
U.S. Appl. No. 17/410,162, filed Aug. 24, 2021, Neurovascular Catheter Having Angled Tip.
U.S. Appl. No. 17/407,852, filed Aug. 20, 2021, Systems and Methods for Multivariate Stroke Detection.
U.S. Appl. No. 17/398,244, filed Aug. 10, 2021, Catheter With a Preset Curve.
Guidezilla Guide Extension Catheter, Boston Scientific 510k Submission, Feb. 20, 2017.
Merit Medical Systems Acquired Distal Access's SPINR Platform, Jul. 15, 2015, Digital Access, LLC; Merit Medical Systems, 5 pages.
Simon et al., *Exploring the efficacy of cyclic vs. static aspiration in a cerebral thrombectomy model: an initial proof of concept study*, J. NeuroInvent Surg 2014, 6 pp. 677-683.
Simon et al., *Hydrodynamic comparison of the Penumbra system and commonly available syringes in forced—suction thrombectomy*, J. NeuroInvent Surg 2014, 6, pp. 205-211.
Spiotta et al., Evolution of thrombectomy approaches and devices for acute stroke: a technical review, J. Neuro Intervent Surg 2015, 7, pp. 2-7.
U.S. Appl. No. 17/125,742, filed Methods and Systems for Accessing and Retrieving Thrombo-Emboli.
U.S. Appl. No. 16/704,330, filed Dec. 5, 2019, Neurovascular Aspiration Catheter With Elliptical Aspiration Port.
U.S. Appl. No. 17/125,743, filed Dec. 17, 2020, Systems for Accessign a Central Pulmonary Artery.

* cited by examiner

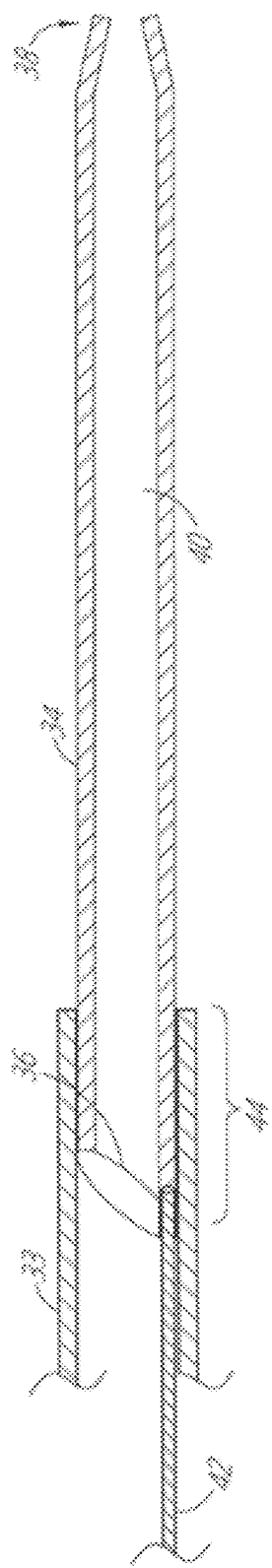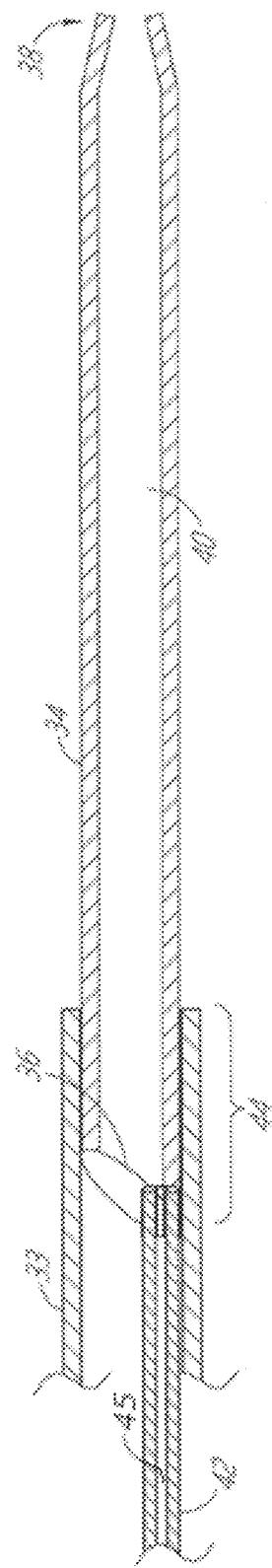

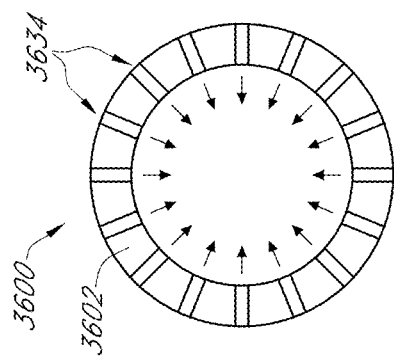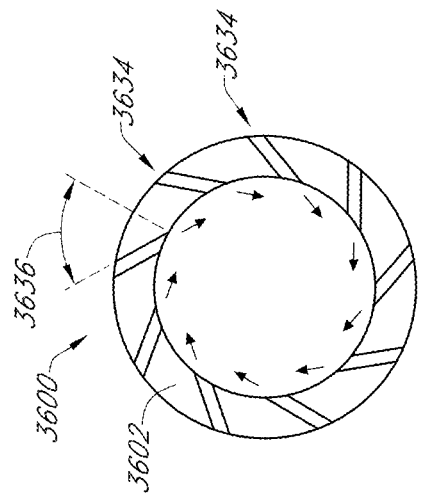
FIG. 13Di     FIG. 13Dii

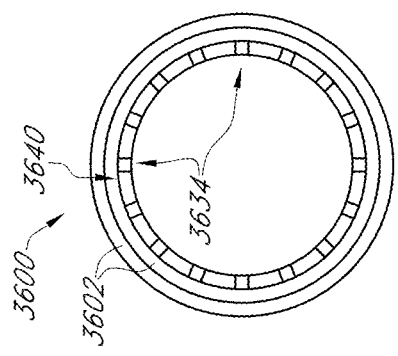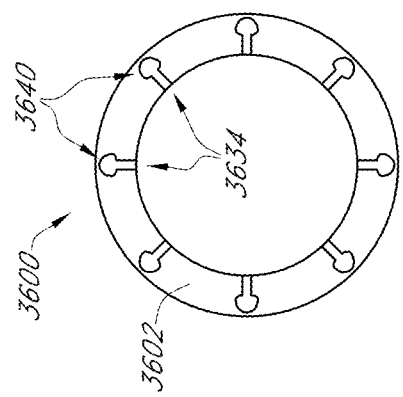
FIG. 13Diii  FIG. 13Div

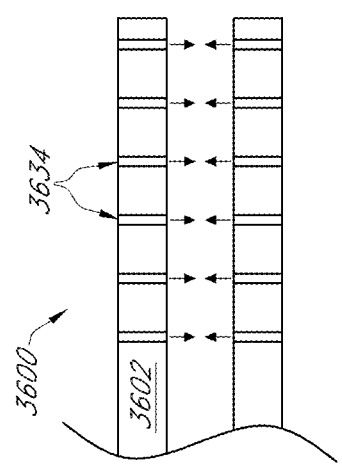
FIG. 13Hi
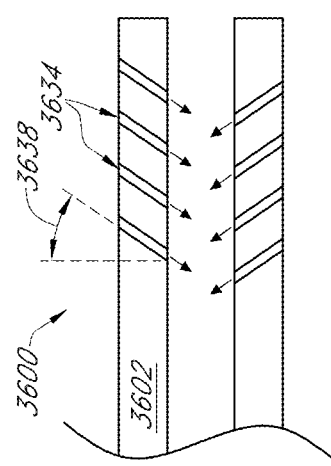
FIG. 13Hii

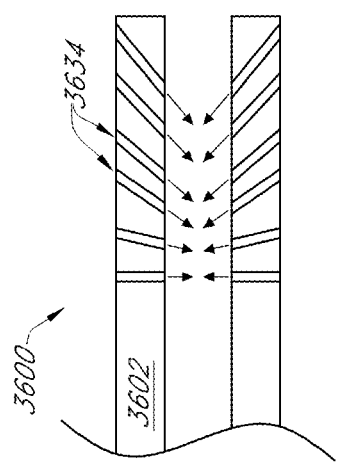
FIG. 13Hiii
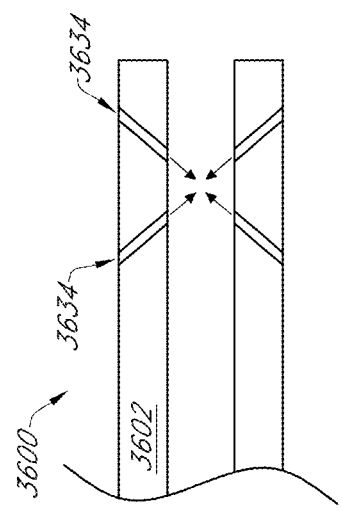
FIG. 13Hiv

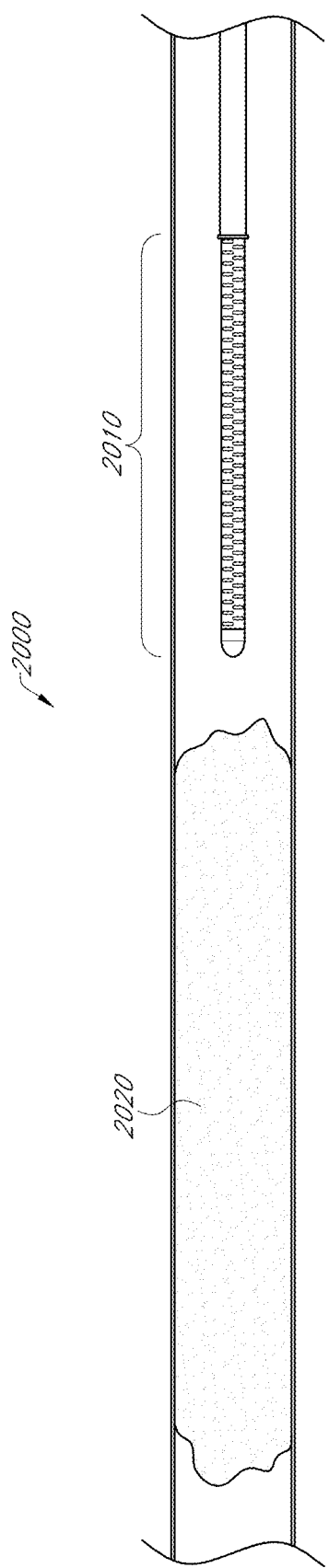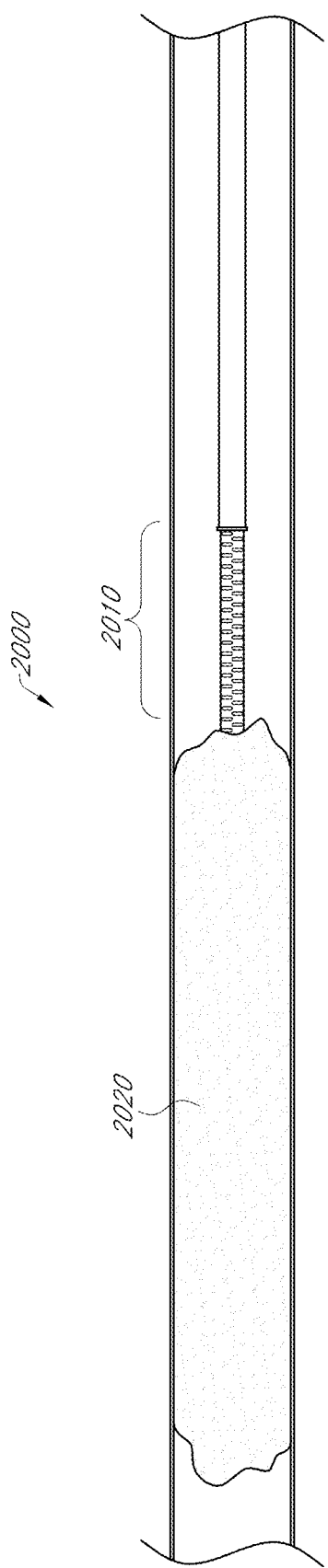
FIG. 20A
FIG. 20B

| Standard Catheter ID (in.) | Segment Length for Equivalent Aspiration Area (mm) |
|---|---|
| 0.035 | 1.0 |
| 0.040 | 1.3 |
| 0.055 | 2.5 |
| 0.071 | 4.2 |
| 0.088 | 6.5 |

FIG. 24

ENHANCED FLEXIBILITY NEUROVASCULAR CATHETER

CROSS-REFERENCE TO RELATED APPLICATIONS

This application claims the priority benefit of U.S. Provisional Patent Application Ser. No. 62/826,203, filed Mar. 29, 2019, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

BACKGROUND

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons or stents have been used to create a patent lumen through the clot when clot removal or dissolution was not possible.

Notwithstanding the foregoing, there remains a need for new devices and methods for treating vasculature occlusions in the body, including acute ischemic stroke and occlusive cerebrovascular disease.

SUMMARY

Disclosed herein is a neurovascular catheter having a proximal end, a distal end, and a sidewall. The sidewall forms a lumen extending from the proximal end to the distal end. A plurality of holes is disposed in the sidewall which measurably alter a bending stiffness within a region of the catheter having the plurality of holes.

At least some of the plurality of holes may be through-holes. At least some of the plurality of holes may be blind holes. At least some of the plurality of holes include a filler material. The filler material may increase the stiffness of the region having the plurality of holes. The filler material may decrease the stiffness of the region having the plurality of holes. At least some of the plurality of holes may include a filler material that at least partially dissolves in an aqueous environment. At least some of the plurality of holes may include a filler material that reacts with intravascular biomolecules. At least some of the plurality of holes may include a filler material comprising a polyether block amide, a thermoplastic polyurethane elastomer, polytetrafluoroethylene (PTFE), and/or polyethylene glycol (PEG). At least some of the plurality of holes may include a filler material that swells when subjected to an aqueous environment. At least some of the plurality of holes may include a thixotropic or rheopectic material. At least some of the plurality of holes may include a dilatant or pseudoplastic material.

The region having the plurality of holes may extend partially around the circumference of the catheter. The region may extend around the entire circumference of the catheter. The plurality of holes may be configured to prevent water from passing through the holes. The plurality of holes may form a gradient in stiffness along an axial direction over the region. The plurality of holes may form a gradient in stiffness along a circumferential direction over the region. The sidewall may have a proximal segment and an adjacent distal segment, the proximal and distal segments having different durometers. The region comprising the plurality of holes may be positioned at the transition between the two adjacent segments. The proximal segment may be stiffer than the distal segment. At least some of the plurality of holes may be positioned at a distal end of the proximal segment and configured to reduce the stiffness of the proximal segment. At least some of the plurality of holes may be positioned at a proximal end of the distal segment and configured to increase the stiffness of the distal segment. The sidewall may include a braid over a portion of the length of the catheter and a coil over an adjacent portion of the length of the catheter. The region of the catheter having the plurality of holes may be positioned at a transition between the braid and the coil. The coil may have at least two adjacent sections of different pitch and the region having the plurality of holes may be positioned at a transition between the two adjacent sections of different pitch.

At least some of the plurality of holes may form a plurality axially-spaced notches extending partially around the circumference of the catheter. The catheter may be more prone to bend toward a lateral side of the catheter having the notches. The catheter may be less prone to bend toward a lateral side of the catheter comprising the notches. The catheter may have a braid confined to only a portion of the circumference of the catheter along at least a portion of a length of the catheter.

At least a portion of an outer surface of the sidewall may have a textured surface configured to reduce friction between the sidewall and a surrounding blood vessel. The catheter may include a second catheter segment axially translatable through the lumen. The second catheter segment may have a proximal end, a distal end, and an inner sidewall forming an inner lumen extending from the proximal end to the distal end of the second catheter segment. A second plurality of holes may be disposed in the inner sidewall which measurably alter a bending stiffness within a region of the second catheter segment having the second plurality of holes. Axial translation of the second catheter segment relative to the catheter lumen may modulate the bulk mechanical properties of the neurovascular catheter along at least a portion of a region where the catheter and second catheter segment overlap.

In another aspect of the invention, disclosed herein is a neurovascular catheter having a proximal end, a distal end, and a sidewall. The sidewall forms a central lumen extending from the proximal end to the distal end. A plurality of holes is disposed in the sidewall near the distal end of the of the catheter which allow fluid to flow into the central lumen.

At least some of the plurality of holes may extend from an inner diameter of the sidewall to an outer diameter in the sidewall. At least some of the plurality of holes may extend from an inner diameter of the sidewall to an internal lumen disposed within the sidewall. The internal lumen may be configured to place the at least some of the plurality of holes in fluid communication with a fluid source outside of a body of a patient. The internal lumen may be concentric with the central lumen. The neurovascular catheter may further include a compliant sleeve configured to be introduced concentrically around an outer diameter of the sidewall. The compliant sleeve may be configured to deliver fluid form a fluid source outside of a body of the patient to at least some of the plurality of holes. At least some of the plurality of holes may be angled in a circumferential direction. At least some of the plurality of holes may be angled in a longitudinal direction. At least some of the plurality of holes may be configured to create a vortex flow within the lumen of the catheter.

In another aspect of the invention, disclosed herein is a reperfusion catheter having an elongate tubular body extending from a proximal end to a distal end and defining a lumen; and an at least partially porous tubular body. The at least partially porous tubular body includes a proximal portion coupled to the distal end of the elongate tubular body; a distal tip; and a sidewall extending between a proximal end of the at least partially porous tubular body and the distal tip. The sidewall includes an active region defining a plurality of apertures fluidly coupled to the lumen of the elongate tubular body. In some embodiments, a percentage of an area of the plurality of apertures to a total surface area of the active region is within a range from about 15% to about 20%. In some embodiments, the reperfusion catheter is configured to draw a vacuum through the plurality of apertures to engage embolic material in an intravascular site of a patient.

In some embodiments, the reperfusion catheter includes an elongate shaft extending through the lumen of the elongate tubular body, such that the proximal end of the at least partially porous tubular body is coupled to a distal end of the elongate shaft. In some embodiments, the proximal end of at least partially porous tubular body is coupled to the distal end of the elongate tubular body. In some embodiments, an outer diameter of the at least partially porous tubular body is greater than an outer diameter of the elongate tubular body.

In some embodiments, the distal tip of the at least partially porous tubular body defines an opening configured to receive a guidewire therethrough. In some embodiments, the distal tip of the at least partially porous tubular body includes a silicone valve configured to receive a guidewire therethrough. In some embodiments, an axial length of the active region is between about 5 millimeters (mm) and about 15 mm. In some embodiments, an outer diameter of the active region is within a range from about 0.020 inches to 0.025 inches. In some embodiments, the distal tip of the at least partially porous tubular body comprises an atraumatic tip.

In some embodiments, the reperfusion catheter includes means to adjust a length of the active region. In some embodiments, such means include a sleeve extending around at least a portion of a perimeter of the active region, such that the sleeve is slidably engaged with the active region to adjustably control a number of exposed apertures of the plurality of apertures.

In another aspect of the invention, disclosed herein is a medical device including: a first elongate tubular body having a proximal end, a distal end, and defining a first lumen; and a second elongate tubular body configured to extend through the first lumen. In some embodiments, the second elongate tubular body has a proximal end, a distal end, a second lumen defined therethrough, and an active region defining a plurality of apertures fluidly coupled to the second lumen. In some embodiments, a percentage of an area of the plurality of apertures to a total surface area of the active region is within a range from about 15% to about 20%. In some embodiments, the second catheter is configured to draw a first vacuum through the plurality of apertures to engage embolic material in an intravascular site of a patient. In some embodiments, the first catheter is configured to draw a second vacuum through the distal end of the first catheter to remove the embolic material from the intravascular site.

In some embodiments, the medical device further includes an elongate shaft extending through the second lumen; and an at least partially porous tubular body extending from a distal end of the elongate shaft, such that the at least partially porous tubular body comprises the active region. In some embodiments, the at least partially porous tubular body includes or is formed of an active region. In some embodiments, an outer diameter of the at least partially porous tubular body is greater than an outer diameter of the second elongate tubular body. In some embodiments, the distal end of the second elongate tubular body defines an opening configured to receive a guidewire therethrough or a silicone valve configured to receive a guidewire therethrough.

In some embodiments, the second catheter includes a sleeve extending around at least a portion of a perimeter of the active region, such that the sleeve is slidable engaged with the active region to adjustably control a number of exposed apertures of the plurality of apertures.

In another aspect of the invention, disclosed herein is a method of removing embolic material from an intravascular site of a patient. In some embodiments, the method includes navigating, through vasculature of the patient to the intravascular site, a first elongate tubular body having a proximal end, a distal end, and defining a first lumen; distally advancing a second elongate tubular body through the first lumen into at least a portion of an embolic material at the intravascular site; drawing a first vacuum through a plurality of apertures to engage the embolic material; and proximally withdrawing the second elongate tubular body into the first lumen of the first elongate tubular body to retract the embolic material into the first lumen.

In some embodiments, the second elongate tubular body includes a proximal end, a distal end, and defines a second lumen; and an active region defining a plurality of apertures fluidly coupled to the second lumen. In some embodiments, a percentage of an area of the plurality of apertures to a total surface area of the active region is within a range from about 15% to about 20%.

In some embodiments, withdrawing the second elongate body into the first lumen includes: distally advancing the first elongate body toward the embolic material; and drawing a second vacuum through the first lumen and proximally withdrawing the second elongate body into the first lumen to retract the embolic material into the first lumen.

In some embodiments, the second elongate body includes a radiopaque marker proximally adjacent the active region, such that distally advancing the second elongate body includes distally advancing the second elongate body into at least a portion of the embolic material to position the radiopaque marker adjacent a proximal face of the embolic material.

In some embodiments, navigating the first and second elongate bodies includes: navigating an elongate shaft to the intravascular site; and navigating, over the elongate shaft, the first and second elongate bodies to the intravascular site.

In some embodiments, the second elongate body includes a sleeve extending around at least a portion of a perimeter of the active region, such that the method further includes adjusting an axial position of the sleeve to control a number of exposed apertures of the plurality of apertures.

In another aspect of the invention, disclosed herein is a method of making a flexible distal zone on a neurovascular catheter, having an elongate tubular body with a distal end. The method includes: dip coating a removable mandrel to form a tubular inner liner on the mandrel; softening at least a portion of the tubular inner liner on the mandrel; applying a helical coil to the outside of the inner liner; positioning a plurality of tubular segments over the helical coil, the plurality of segments having durometers that decrease in a distal direction; heating the tubular segments to form the flexible distal zone on the neurovascular catheter; and removing the mandrel.

In some embodiments, the softened portion of the tubular inner liner comprises a distal about 15 mm to about 20 mm of the tubular inner liner.

In some embodiments, softening comprises applying tension axially to the at least a portion of the tubular inner liner to stretch the at least a portion of the tubular inner liner. In some embodiments, the method further includes achieving a thickness of the softened portion of the tubular inner liner of about 0.00025 inches to 0.00075 inches.

In some embodiments, the method further includes aligning one or more polymer chains of the stretched portion of the tubular inner liner relative to one another in a similar or substantially similar direction as the applied tension.

In some embodiments, softening comprises disposing a plurality of holes in the at least a portion of the inner liner.

For example, the plurality of holes is one or more of: through holes, blind holes, dimples, notches, flow holes, and a combination thereof.

In some embodiments, the method further includes coating the tubular inner liner with a tie layer. In some embodiments, the tie layer comprises polyurethane. In some embodiments, the tie layer has a wall thickness of no more than about 0.005 inches. In some embodiments, the tie layer extends along at least the most distal 20 cm of the neurovascular catheter.

In some embodiments, the method further includes positioning at least one axially extending tensile strength enhancing filament over the tie layer. In some embodiments, the method further includes overlapping the softened portion of the tubular inner liner with the at least one axially extending filament. In some embodiments, the at least one axially extending filament includes an anchoring section, such that the method further includes anchoring the at least one axially extending filament in a section of the catheter that includes the helical coil. In some embodiments, the filament extends along at least about the most distal 15 cm of the length of the catheter. In some embodiments, the filament extends along at least about the most distal 20 cm of the length of the catheter. In some embodiments, the filament comprises multiple fibers.

In some embodiments, the plurality of tubular segments form a proximal section having a proximal end and a distal end and a durometer equal to or greater than 65D at all points along a length from the proximal end to the distal end of the proximal section, a distal section having a proximal end and a distal end and a durometer equal to or less than 35D at all points along a length extending from the proximal end to the distal end of the distal section, and a transition section extending from the distal end of the proximal section to the proximal end of the distal section, the transition section comprising at least two tubular segments and having a durometer less than 65D and greater than 35D at all points along a length extending from the distal end of the proximal section to the proximal end of the distal section, the transition section being shorter in length than the proximal section and shorter in length than the distal section. In some embodiments, the transition section comprises at least three tubular segments. In some embodiments, the distal section is at least about twice as long as the transition section.

In some embodiments, removing the mandrel step includes axially elongating the mandrel.

In some embodiments, the method further includes positioning at least seven segments on the helical coil. In some embodiments, the method further includes positioning at least nine segments on the helical coil.

In some embodiments, the tubular inner liner comprises PTFE.

In some embodiments, the coil comprises a shape memory material. In some embodiments, the coil comprises Nitinol. In some embodiments, the Nitinol comprises an Austenite state at body temperature.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIGS. 3A-3B are cross-sectional elevational views of a distal end of catheter 10, with the distal section 34 fully extended.

FIG. 13E illustrates a cross section bisecting the longitudinal axis. FIG. 13F illustrates a side cross-section of the sleeve in an unbiased configuration. FIG. 13G illustrates fluid flow through delivered through the sleeve placing the sleeve in an expanded configuration.

FIGS. 20A-20F schematically depict various aspects of a method of using a three-dimensional aspiration device.

FIG. 24 depicts a table of various catheter inner diameter dimensions (in inches) as compared to an exemplary segment length of an active aspiration region needed to achieve an equivalent aspiration area (in mm).

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Figure 1:
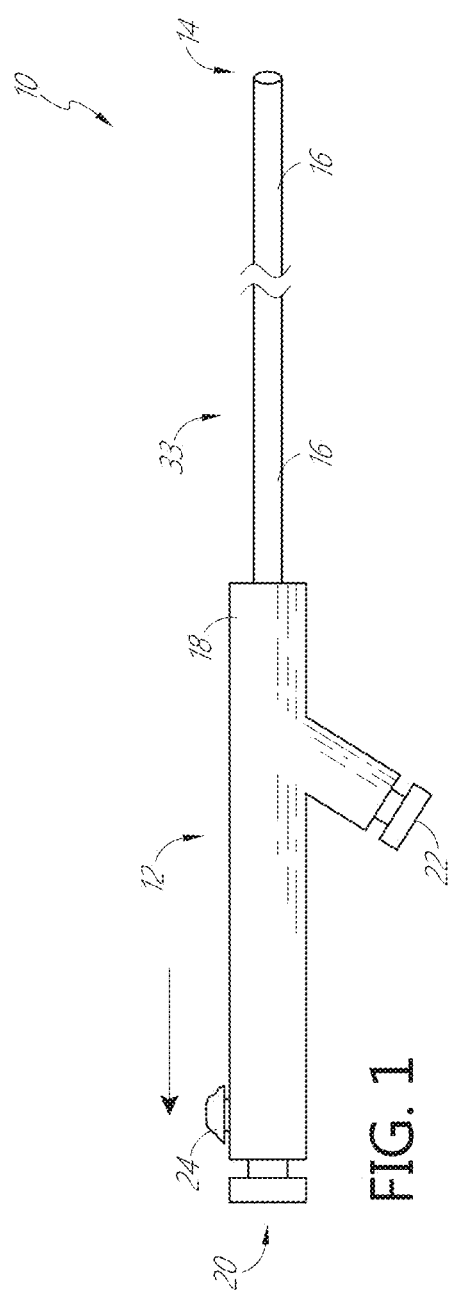
FIG. 1 is a side elevational schematic view of an intracranial aspiration catheter in accordance with the present invention, with a distal segment in a proximally retracted configuration.

Referring to FIG. 1, there is disclosed a catheter 10 in accordance with one aspect of the present invention. Although primarily described in the context of an axially extendable distal segment aspiration catheter with a single central lumen, catheters of the present invention can readily be modified to incorporate additional structures, such as permanent or removable column strength enhancing mandrels, two or more lumens such as to permit drug, contrast, or irrigant infusion or to supply inflation media to an inflatable balloon carried by the catheter, or combinations of these features, as will be readily apparent to one of skill in the art in view of the disclosure herein. In addition, the present invention will be described primarily in the context of removing obstructive material from remote vasculature in the brain but has applicability as an access catheter for delivery and removal of any of a variety of diagnostics or therapeutic devices with or without aspiration.

The catheters disclosed herein may readily be adapted for use throughout the body wherever it may be desirable to distally advance a low profile distal catheter segment from a larger diameter proximal segment. For example, axially extendable catheter shafts in accordance with the present invention may be dimensioned for use throughout the coronary and peripheral vasculature, the gastrointestinal tract, the urethra, ureters, Fallopian tubes and other lumens and potential lumens, as well. The telescoping structure of the present invention may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

Figure 2:
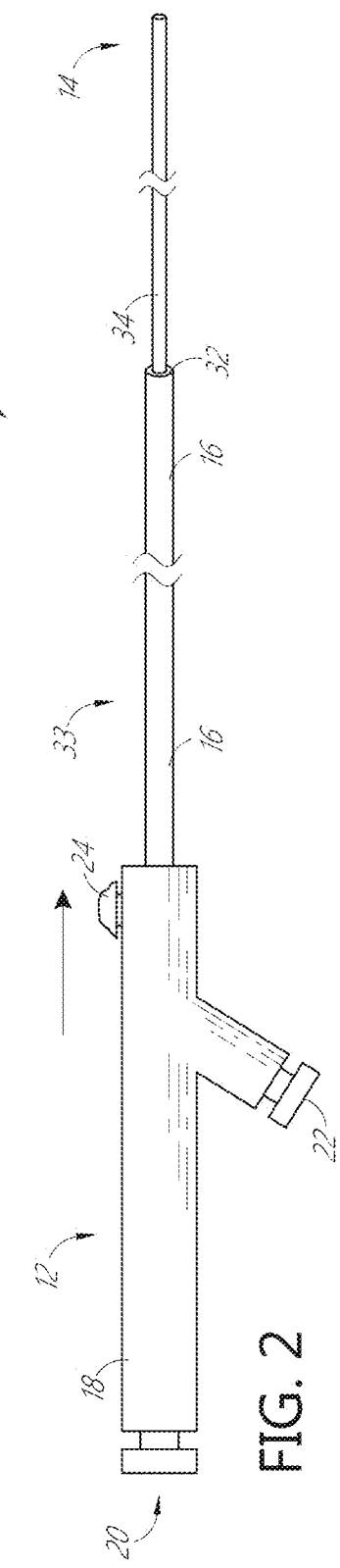
FIG. 2 is a side elevational view as in FIG. 1, with the distal segment in a distally extended configuration.

In the illustrated embodiment, the tubular body 16 is divided into at least a fixed proximal section 33 and an axially extendable and retractable distal section 34 separated at a transition 32. FIG. 2 is a side elevational view of the catheter 10 shown in FIG. 1, with the distal segment in a distally extended configuration.

Referring to FIGS. 3A and 3B, there is illustrated a cross-sectional view of the distal segment 34 shown extended distally from the proximal segment 33 in accordance with the present invention. Distal segment 34 extends between a proximal end 36 and a distal end 38 and defines at least one elongate central lumen 40 extending axially therethrough. Distal end 38 may be provided with one or more movable side walls or jaws 39, which move laterally in the direction of an opposing side wall or jaw 41 under the influence of aspiration, to enable the distal end 38 to bite or break thrombus or other material into smaller particles, to facilitate aspiration through lumen 40. Both walls 39 and 41 may be movable towards and away from each other to break up thrombus as is discussed further below. For certain applications, the proximal section 33 may also or alternatively be provided with one or two opposing jaws, also responsive to vacuum or mechanical actuation to break up thrombus.

The inner diameter of the distal section 34 may be between about 0.030 inches and about 0.112 inches, between about 0.040 inches and about 0.102 inches, between about 0.045 inches and about 0.097 inches, between about 0.050 inches and about 0.092 inches, between about 0.055 inches and about 0.087 inches, between about 0.060 inches and about 0.082 inches, between about 0.062 inches and about 0.080 inches, between about 0.064 inches and about 0.078 inches, between about 0.066 inches and about 0.076 inches, between about 0.068 inches and about 0.074 inches, or between about 0.070 inches and about 0.072 inches.

The inner diameter and the outer diameter of the distal section 34 may be constant or substantially constant along its longitudinal length. The inner diameter may be at least about 0.06 inches, 0.065 inches, 0.07 inches, 0.075 inches, 0.08 inches, or more than 0.08 inches. The outer diameter may be at least about 0.07 inches, 0.075 inches, 0.08 inches, 0.085 inches, 0.09 inches, 0.095 inches, 0.1 inches, or more than 0.1 inches. The total thickness of the sidewall extending between the inner and outer diameter may be at least about 0.005 inches, 0.010 inches, 0.015 inches, 0.02 inches, 0.025 inches, or more than 0.025 inches. For example, the distal section 34 may have an inner diameter of about 0.071 inches and an outer diameter of about 0.083 inches. Alternatively, the distal section 34 may be tapered near its distal end. A larger lumen (internal diameter) may increase the applied aspiration force through the distal end of the distal section 34. A smaller outer diameter may provide better catheter trackability and/or may better enable the catheter to reach more distal anatomy (e.g. neuroanatomy), as the tapered distal end may be better accommodated in smaller blood vessels. The inner and outer diameters of the distal section 34 may be correlated in order to maintain a sufficient sidewall thickness that provides sufficient structural integrity to the catheter. The distal section 34 may be tapered at less than or equal to about 5 cm, about 10 cm, about 15 cm, about 20 cm, about 23 cm, about 25 cm, about 30 cm, about 31 cm, about 35 cm, about 40 cm, about 45 cm, about 50 cm, about 60 cm, or about 70 cm from its distal end. In some embodiments, the taper may be positioned between about 25 cm and about 35 cm from the distal end of the distal section 34. In some embodiments, the taper may be positioned between about 15 cm and about 25 cm from the distal end of the distal section 34.

The inner diameter of the distal section 34 may be tapered or decreased in the distal direction near the distal end to an internal diameter that is less than or equal to about 95%, about 90%, about 85%, about 80%, about 75%, about 70%, about 65%, about 60%, about 55%, or about 50% of the adjacent, untapered internal diameter. In some embodiments, the internal diameter of the tapered distal section 34 may be between about 50% and about 70% of the adjacent, untapered internal diameter. For example, the untapered internal diameter at the proximal end of the distal section 34 may be about 0.071 inches and the tapered internal diameter at the distal end of the distal section 34 may be about 0.035 inches, 0.045 inches, or 0.055 inches. The inner diameter of the distal section 34 may be tapered or increased near the distal end by greater than or equal to about 102%, 104%, 106%, 108%, or more of the internal diameter just proximal to a transition into the taper. The tapered inner diameter of the distal section 34 may be less than or equal to about 0.11 inches, about 0.1 inches, about 0.090 inches, about 0.080 inches, about 0.070 inches, about 0.065 inches, about 0.060 inches, about 0.055 inches, about 0.050 inches, about 0.045 inches, about 0.040 inches, about 0.035 inches, about 0.030 inches, about 0.025 inches, about 0.020 inches, about 0.015 inches, or about 0.010 inches. The taper in the outer diameter of the tapered portion of the distal section 34 may be matched to maintain a constant thickness of the sidewall. Alternatively, the sidewall may be thinner along the tapered portion. For instance, the sidewall may be no greater than 95%, 90%, 85%, 80%, 75%, 70%, or less than 70% of the thickness of the sidewall along the proximal portion of the distal section 34. In some embodiments, the length of the distal tapered portion of the distal section 34 may be between about 25 cm and about 35 cm, between about 25 cm and about 30 cm, between about 30 cm and 35 cm, or approximately 30 cm.

In some embodiments, the proximal segment 33 may have an inner diameter of at least about 0.07 inches, 0.075 inches, 0.08 inches, 0.085 inches, 0.09 inches, 0.1 inches, 0.105 inches, or more than 0.105 inches. The proximal segment 33 may have an outer diameter of at least about 0.08 inches, 0.085 inches, 0.09 inches, 0.095 inches, 0.01 inches, 0.105 inches, 0.11 inches, 0.0115 inches, 0.012 inches, or more than 0.012 inches. For example, the inner diameter may be approximately 0.088 inches and the outer diameter may be approximately 0.106 inches. The sidewall of the proximal segment 33 may have a thickness of at least about 0.005 inches, 0.01 inches, 0.015 inches, 0.02 inches, 0.025 inches, or more than 0.25 inches. In some embodiments, the proximal segment 33 has a constant inner and/or outer diameter along its length. In some embodiments, the proximal segment 33 may slightly taper or decrease in diameter along the distal direction. For example, in some embodiments, the outer diameter of the proximal segment 33 may be about 0.106 inches at the distal end and about 0.108 inches at the proximal end.

The length of the proximal segment 33 may be at least about 90 cm, 95 cm, 100 cm, 105 cm, 110 cm, 115 cm, 120 cm, 125 cm, 130 cm, 135 cm, or more than 135 cm. For example, in one embodiment the length is approximately 106 cm. In another embodiment, the length is approximately 117 cm. In some neurovascular applications, the distal end of the proximal segment 33 may extend at least to the Horizontal Petrous segment of the vasculature.

In some embodiments, the length of the distal section 34 may be between about 13 cm and about 53 cm, between about 18 cm and about 48 cm, between about 23 cm and about 43 cm, between about 28 cm and about 38 cm, between about 20 cm and 30 cm, or between about 25 cm and 30 cm. The length of the distal section 34 may be less than or equal to about 20 cm, about 25 cm, about 30 cm, about 33 cm, about 35 cm, about 40 cm, about 41 cm, about 45 cm, about 50 cm, about 55 cm, about 60 cm, about 70 cm, or about 80 cm. The length of the distal section 34 may depend on the degree of tapering of the internal diameter of the distal section 34.

The proximal end 36 of distal section 34 is provided with a proximally extending pull wire 42. Pull wire 42 extends proximally throughout the length of the tubular body 16, to control 24 which may be carried by manifold 18. Axial movement of control 24 produces a corresponding axial movement of distal section 34 with respect to proximal section 33 as has been discussed. Alternatively, the proximal end of pull wire 42 may exit through a port on manifold 18, such that it may be manually grasped and pulled or pushed by the clinician to extend or retract the distal section 34. The length of the pull wire 42 may be between about 700 mm and about 1556 mm, between about 800 mm and about 1456 mm, between about 850 mm and about 1406 mm, between about 900 mm and about 1356 mm, between about 950 mm and about 1306 mm, between about 1000 mm and about 1256 mm, between about 1020 mm and about 1236 mm, between about 1040 mm and about 1216 mm, between about 1060 mm and about 1196 mm, between about 1080 mm and about 1176 mm, between about 1100 mm and about 1156 mm, between about 1110 mm and about 1146 mm, or between about 1120 mm and about 1136 mm. In some preferred embodiments, the length of the pull wire 42 may be between approximately 110-120 cm.

Upon distal advance of pull wire 42 to its limit of travel, an overlap 44 remains between the proximal end 36 of distal section 34 and the proximal section 33. This overlap 44 is configured to provide a seal to enable efficient transmission of vacuum from proximal section 33 to distal section 34. In some embodiments, the length of the pull wire 42 may be limited to ensure that there is a minimal overlap 44 between the proximal segment 33 and the distal segment 34 when the pull wire 42 is fully inserted into the proximal segment 33 or attached manifold in a distal direction. In some embodiments, the length of the proximal segment 33 may be sufficiently long for neurovascular applications such that when the proximal segment is positioned in a relatively proximal position (e.g., the horizontal petrous segment), the neuroanatomy effectively limits the distance by which the distal segment 34 may be extended, ensuring a sufficient overlap 44. For example, the distal segment 34 may not be able to extend further than the M2 segment of the middle cerebral artery (MCA) given its dimensions. Overlap 44 may be provided with any of a variety of additional features to facilitate a seal, such as a gasket, coating or tightly toleranced sliding fit, as described elsewhere herein. In some embodiments, the proximal end of the distal segment 34 may be slightly expanded to create a seal. For instance, the outer diameter of the proximal end of the distal segment 34 and the inner diameter of the proximal segment 33 may both be about 0.088 inches. Preferably the clearance between the OD of the distal section 34 and ID of the proximal section 33, at least in the vicinity of transition 32, will be no more than about 0.005 inches and preferably no more than about 0.003 inches to provide an effective seal in a blood environment. A larger clearance may be more feasible in embodiments comprising a sealing feature as described elsewhere herein.

Following positioning of the distal end of proximal section 33 within the vasculature, such as within the cervical carotid artery, the control 24 is manipulated to distally advance distal section 34 deeper into the vasculature. For this purpose, the pull wire 42 will be provided with sufficient column strength to enable distal advance of the distal tip 38 as will be discussed below.

The pull wire 42 and distal section 34 may be integrated into a catheter as illustrated in FIGS. 1 and 2. Alternatively, distal section 34 and pull wire 42 may be configured as a stand-alone catheter extension device as is discussed in greater detail below. The catheter extension device may be introduced into the proximal end of proximal section 33 after placement of proximal section 33 and advanced distally there through as illustrated in FIG. 3A, to telescopically extend the reach of the aspiration system.

Referring to FIG. 3B, the pull wire 42 may comprise a tubular wall having an axially extending central lumen 45. The central lumen 45 permits introduction of media such as lubricants, drugs, contrast agents or others into the distal section 34. In addition, the central lumen 45 extending through pull wire 42 permits introduction of an agitator as is discussed in greater detail below. As shown in FIG. 3B, the central lumen 45 may open into the lumen 40. The distal opening of the central lumen 45 may be positioned at a point along the length of the distal section 34 such that the central lumen 45 terminates where the lumen 40 begins (the distal opening of central lumen 45 may be longitudinally aligned with the proximal opening of lumen 40). The proximal opening of lumen 40 may be angled or slanted as shown in FIG. 3B. In some embodiments, the opening of lumen 40 may be flat. The distal opening of central lumen 45 may be flat as shown in FIG. 3B. In some embodiments, the opening may be angled or slanted, similar to the opening of lumen 40 in FIG. 3B.

In some embodiments, the central lumen 45 may terminate proximal to the opening of the lumen 40. In some embodiments, the central lumen 45 may terminate distal to the opening of the lumen 40 and/or the proximal end of the distal section 34 (e.g., at a point within the lumen 40). For example, the central lumen 45 may terminate at the distal end of the distal section or just short of the distal end (e.g., no more than approximately 1 cm from the distal end). In some implementations, the portion of the pull wire 42, with or without a central lumen 45, which extends beyond the proximal end of the distal section 34 (e.g., into lumen 40) may decrease in stiffness (durometer) in a distal direction. The pull wire 42 may be relatively stiff along the portion proximal to the proximal end of the distal section 34 in order to provide sufficient pushability of the extension catheter. The stiffness of the portion of the pull wire 42 distal of the proximal end of the distal section 34 may substantially match or be less than the stiffness of the distal section 34 along the length of the distal section 34. The portion of the pull wire 42 distal of the proximal end of the distal section 34 may have a uniform stiffness less than the stiffness of the portion proximal of the proximal end of the distal section 34 or it may have a gradated or gradually decreasing stiffness in the distal direction, decreasing from the stiffness of the portion proximal of the proximal end of the distal section 34. For example, the pull wire 42 may comprise metal along the portion proximal to the proximal end of the distal section 34 and may comprise a polymer, softer than the metal, along the portion distal to the proximal end of the distal section 34. The portion distal to the proximal end, in some embodiments, may be extruded with decreasing stiffness in the distal direction.

Any of the catheter shaft or sections of the catheter shaft or telescoping extensions in accordance with the present invention, such as inner device 3402 or outer device 3404, may comprise a multi-layer construct having a high degree of flexibility and sufficient pushability to reach deep into the cerebral vasculature, such as at least as deep as the petrous, cavernous, or cerebral segment of the internal carotid artery (ICA).

Figure 4:
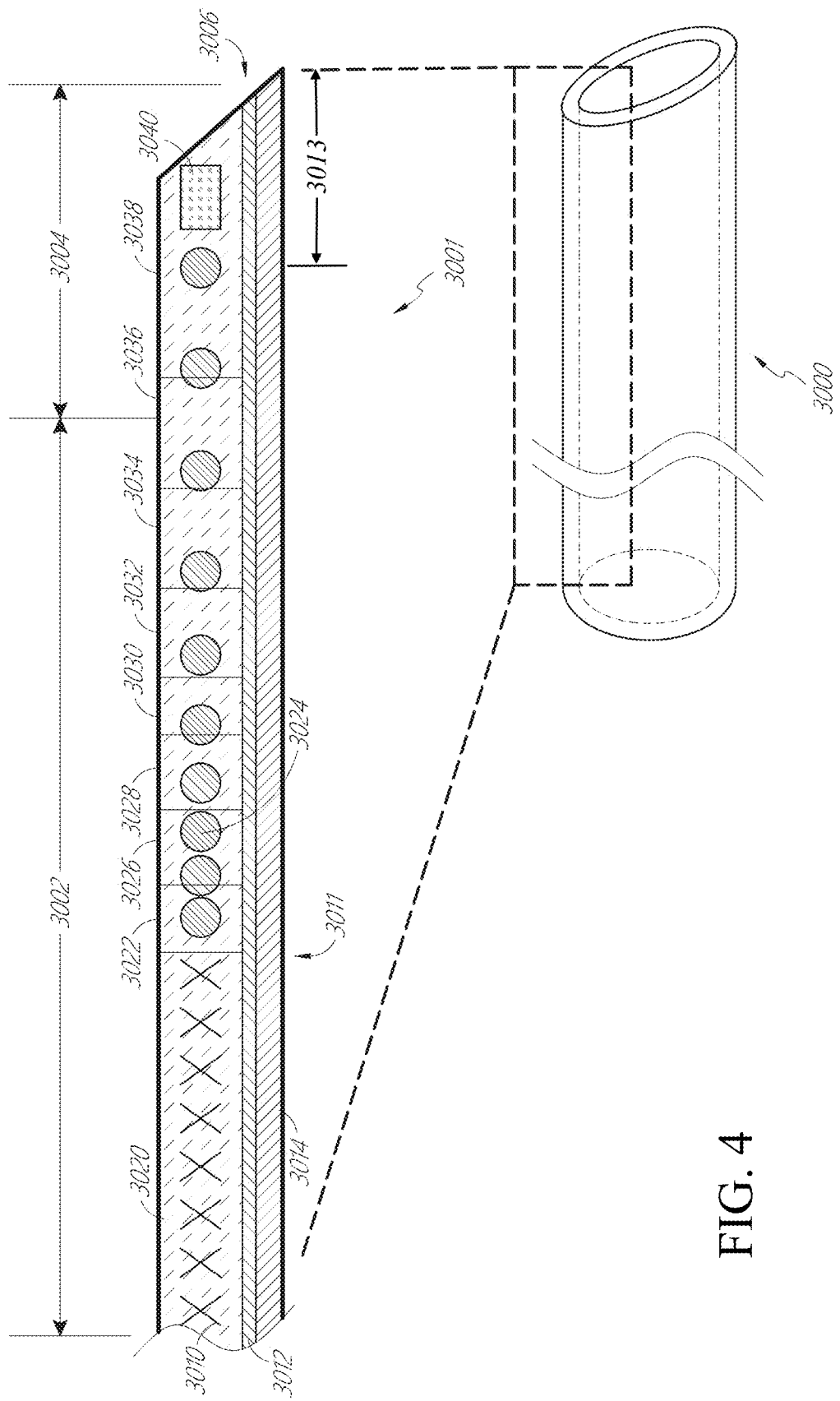
FIG. 4 illustrates a cross-sectional elevational view of a catheter wall according to an embodiment.

In one example, referring to FIG. 4, a catheter 3000, which may be the same or similar to device 3400, may have an effective length from the manifold to distal tip from about 70 cm to about 150 cm, from about 80 cm to about 140 cm, from about 90 cm to about 130 cm, from about 100 cm to about 120 cm, or from about 105 cm to about 115 cm. The outer diameter of the catheter 3000 may be from about 0.07 inches to about 0.15 inches, from about 0.08 inches to about 0.14 inches, from about 0.09 inches to about 0.13 inches, from about 0.1 inches to about 0.12 inches, or from about 0.105 inches to about 0.115 inches, and may be lower in a distal segment than in a proximal segment. The inner diameter 3108 of the catheter 3000 in a single central lumen embodiment may be greater than or equal to about 0.11 inches, greater than or equal to about 0.1 inches, greater than or equal to about 0.09 inches, greater than or equal to about 0.088 inches, greater than or equal to about 0.08 inches, greater than or equal to about 0.07 inches, greater than or equal to about 0.06 inches, or greater than or equal to about 0.05 inches. The inner diameter 3108 of the catheter 3000 in a single central lumen embodiment may be less than or equal to about 0.11 inches, less than or equal to about 0.1 inches, less than or equal to about 0.09 inches, less than or equal to about 0.088 inches, less than or equal to about 0.08 inches, less than or equal to about 0.07 inches, less than or equal to about 0.06 inches, or less than or equal to about 0.05 inches. Referring to FIG. 4, an inner liner 3014 may be formed by dip coating a mandrel (not shown) to provide a thin walled tubular inside layer of the catheter body 3000. The dip coating may be produced by coating a wire such as a silver coated copper wire in PTFE, expanded-PTFE (e-PTFE), thermoplastic polyurethane (e.g., inherently hydrophilic, lubricious inner diameter property, low durometer; Tecoflex™), Fluorinated Ethylene Propylene (FEP), Polyvinylidene Fluoride (PVDF), or like material. The mandrel may thereafter be axially elongated to reduce its diameter and thereafter removed to leave the tubular inner liner. The outside surface of the tubular inner liner 3014 may thereafter be coated with a soft tie layer 3012 such as polyurethane (e.g., Tecoflex™), to produce a layer having a thickness of no more than about 0.005 inches, and in some implementations approximately 0.001 inches. The tie layer 3012 will generally extend along at least about the most distal 10 cm or 20 cm of the catheter shaft 3000 generally less than about 50 cm and may in one implementation extend approximately the distal 30 cm of the catheter shaft 3000, 3100.

In other embodiments, at least a portion of or a section 3013 of the inner liner 3014 may be stretched or softened, as shown in FIG. 4, to soften at least that section of the catheter and/or to enhance flexibility of at least that section of the catheter. As used herein, softened may include one or more of: stretching the inner liner, applying one or more holes (e.g., any embodiments of holes described elsewhere herein) to the inner liner, applying heat to the inner liner, chemically treating the inner liner, altering manufacturing parameters of the inner liner, etc. Further, although a distal section 3013 of the inner liner 3014 is shown as being the stretched or softened section, it shall be appreciated that any section of the inner liner 3014 may be stretched or softened. For example, a more proximal section, middle section, a section that is aligned with a braided section, a section that is aligned with a coiled section, etc. may be stretched or softened. For example, in one embodiment, the inner liner 3014 is softened or stretched from a first length (e.g., after dip coating and axially elongating on the mandrel as described above) to a second length (e.g., tension applied axially during manufacturing as described elsewhere herein). For example, a range of stretch of at least a portion of the inner liner may be about 20% to about 150% elongation; about 20% to about 75% elongation; about 100% to about 150% elongation; about 50% to about 90% elongation; about 60% to about 80% elongation; about 70% to about 80% elongation; about 50% to about 100% elongation; 20% to about 90% elongation; etc. For example, the softened or stretched portion 3013 of the inner liner 3014 may have a thickness of about 0.0001 inches to about 0.001 inches; about 0.00005 inches to about 0.0005 inches; about 0.00025 inches to about 0.00075 inches; about 0.0004 inches to about 0.0006 inches, about 0.0003 inches to about 0.0007 inches; about 0.0004 inches to about 0.0008 inches, etc. In some embodiments, a stretched or softened section 3013 of the inner liner 3014 may start at a distal end of the catheter and extend proximally at least about 1 mm, at least about 3 mm, at least about 5 mm, at least about 10 mm, at least about 15 mm, at least about 20 mm, at least about 25 mm, etc. In some embodiments, a stretched or softened section 3013 of the inner liner 3014 may start at a distal end of the catheter and extend proximally at least about 0.5 mm to about 3 mm; at least about 1 mm to about 3 mm; at least about 1 mm to about 5 mm; at least about 3 mm to about 5 mm; at least about 1 mm to about 10 mm; at least about 3 mm to about 10 mm; at least about 10 mm to about 15 mm; at least about 15 mm to about 20 mm; at least about 20 mm to about 25 mm; etc. In some embodiments, a distal about 1 mm to about 10 mm; about 0.5 mm to about 10 mm; about 0.5 mm to about 5 mm; about 1 mm to about 5 mm; about 1 mm to about 3 mm; about 10 mm to about 25 mm; about 15 mm to about 20 mm; about 14 mm to about 21 mm; about 13 mm to about 22 mm; about 12 mm to about 23 mm; about 11 mm to about 24 mm; etc. of the inner liner may be stretched or softened. In some embodiments, at least one axially extending filament, as described elsewhere herein, may extend the length of the stretched or elongated section 3013 of the inner liner 3014.

To achieve an inner liner 3014 that is at least partially stretched or softened or that includes a softened or stretched section 3013, tension may be applied axially to the inner liner 3014 to stretch at least a portion or a section 3013 of the inner liner 3014 during manufacturing. For example, the polymer chains of the inner liner 3014 may be aligned in the direction of the tension being applied resulting in higher tensile resistance in the same direction. Stretching at least a portion or a section 3013 of the inner liner 3014 may increase a uniformity of the inner liner 3014, for example polymer chains of the material (e.g., PTFE) may become better aligned with respect to adjacent polymer chains as a result of the stretching. Additionally, or alternatively, stretching at least a portion or a section 3013 of the inner liner 3014 may increase a flexibility of a resulting catheter.

In some embodiments, the inner liner 3014 is stretched before coils are applied to the catheter body.

Figure 13A:
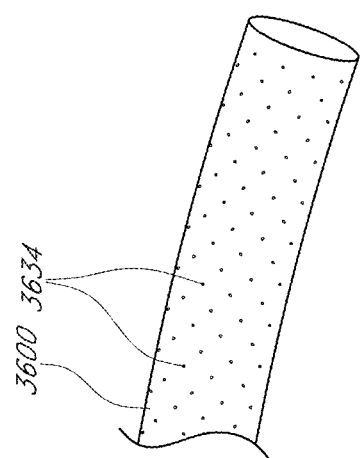
FIG. 13A depicts an example of a distal end of a catheter comprising flow holes.
Figure 13B:
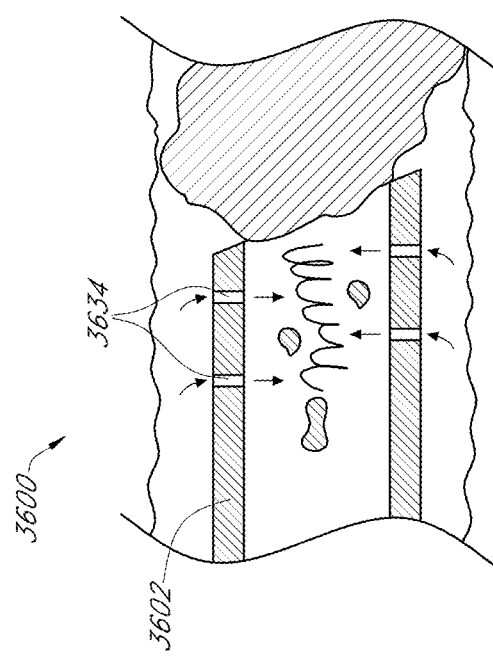
FIG. 13B schematically depicts an example of a distal end of a catheter comprising through flow holes.
Figure 13C:
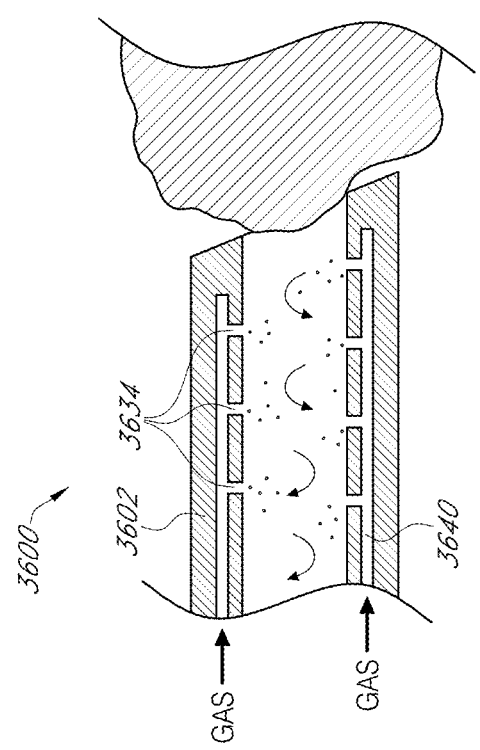
FIG. 13C schematically depicts an example of a distal end of a catheter comprising blind flow holes in fluid communication with an internal lumen.
Figure 13D:
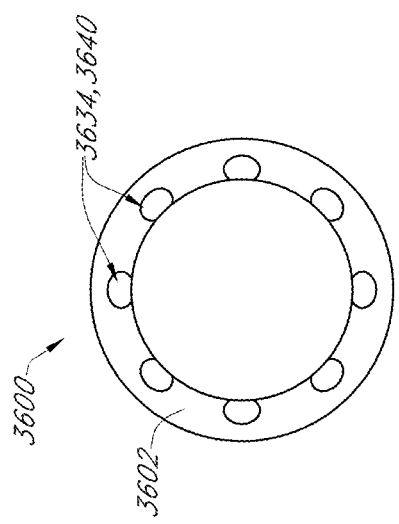
FIGS. 13Di-13Dv schematically illustrate examples of cross-sections of catheters comprising various arrangements and orientations of flow holes.
Figure 13E:
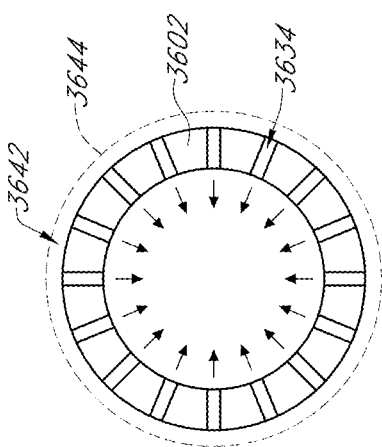
FIG. 13E-13G schematically illustrate various views of a fluid supply lumen formed by a compliant sleeve positioned over the catheter.
Figure 13F:
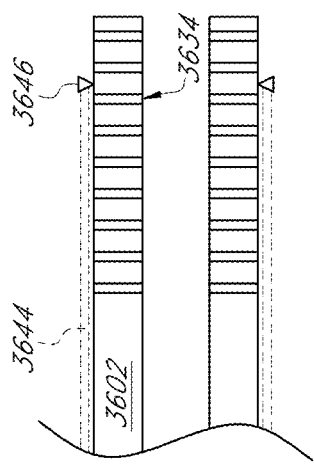
Figure 13G:
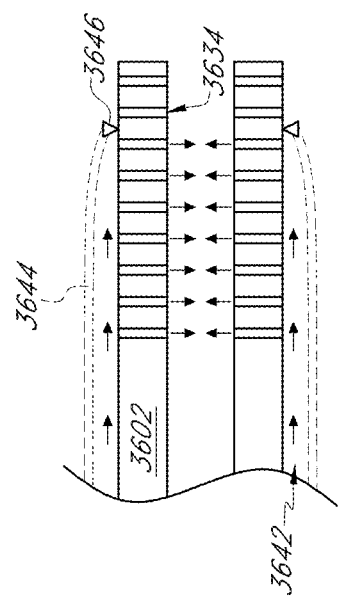
Figure 13H:
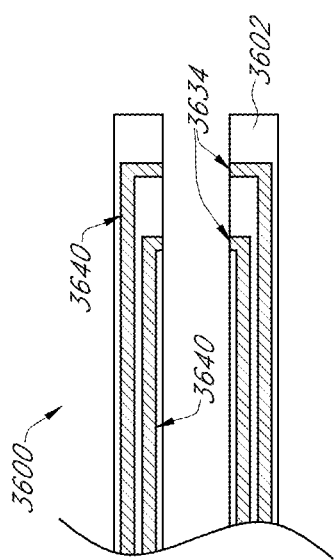
FIGS. 13Hi-13Hv schematically illustrate examples of side cross-sections of catheters comprising various arrangements and orientations of flow holes.
Figure 13I:
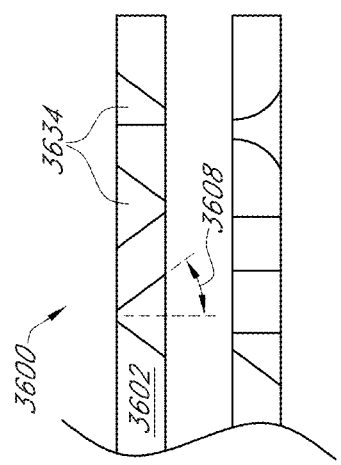
FIG. 13I schematically depicts a side cross-section of a distal end of a catheter comprising various examples of the shapes and orientations of flow holes.
Figure 14:
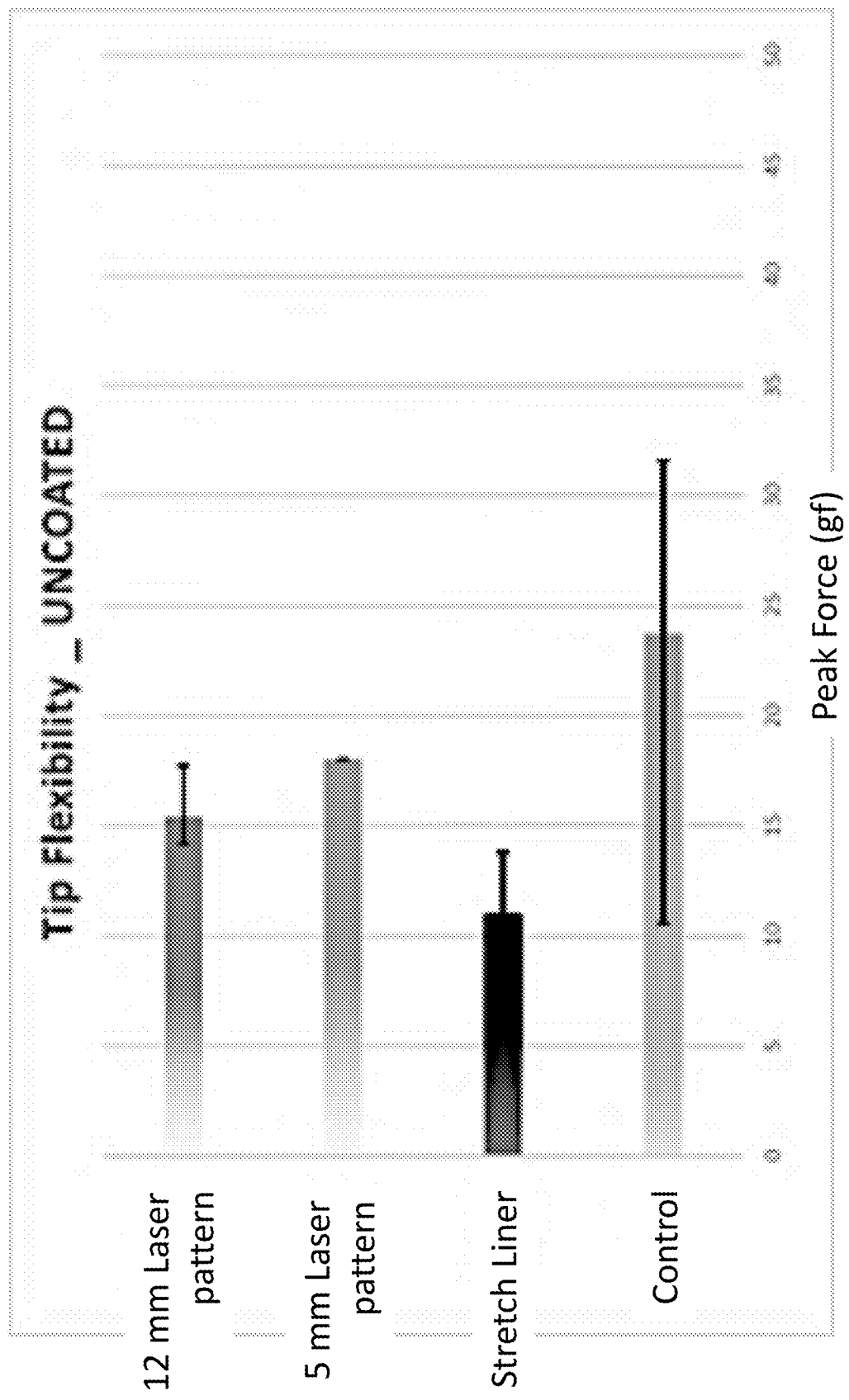
FIG. 14 depicts a graph of tip flexibility of catheters in accordance with the present invention compared with conventional catheters.

As shown in FIG. 14, a cantilever bend test was performed to measure flexibility of various catheters. The control catheter took significant force to flex the catheter shaft and there was high variability between test runs, as shown by the large error bar. In contrast, a catheter including an inner liner having a stretched portion or section (15-20 mm of distal end of inner liner was stretched or softened) had improved flexibility, requiring less force to deflect the catheter shaft. Further, catheters including a softened distal end with either a 5 mm laser pattern or a 12 mm laser pattern (interrupted or segmented pattern) also had improved flexibility and performed reliably as compared to the control. Various patterns of holes, dimples, through holes, blind holes, flow holes, notches, etc. will be described in greater detail with respect to FIGS. 12A-13I.

A braid such as a 75 ppi stainless steel braid 3010 may thereafter be wrapped around the inner liner 3014 through a proximal zone up to a distal transition 3011. From the distal transition 3011 to the distal end of the catheter 3000, a coil 3024 comprising a shape memory material such as a Nitinol alloy may thereafter be wrapped around the inner liner 3014. In one implementation, the Nitinol coil has a transition temperature below body temperature so that the Nitinol resides in the austinite (springy) state at body temperature. Adjacent loops or filars of the coil 3024 may be closely tightly wound in a proximal zone with a distal section having looser spacing between adjacent loops. In an embodiment having a coil section 3024 with an axial length of at least between about 20% and 30% of the overall catheter length, (e.g., 28 cm coil length in a 110 cm catheter shaft 3000), at least the distal 1 or 2 or 3 or 4 cm of the coil will have a spacing that is at least about 130%, and in some implementations at least about 150% or more than the spacing in the proximal coil section. In a 110 cm catheter shaft 3000 having a Nitinol coil the spacing in the proximal coil may be about 0.004 inches and in the distal section may be at least about 0.006 inches or 0.007 inches or more. In embodiments comprising an extension catheter, the distal extendable section of the catheter may be constructed according to the foregoing. The length of the coil 3024 may be proportioned to the length of the extendable catheter segment or the total (e.g., extended) length of the catheter 3000. The coil 3024 may extend from a distal end of the extendable segment over at least about 50%, 60%, 70%, 80%, or 90% of the length of the extendable segment. In some embodiments, the catheter 3000 or the extendable segment may not comprise a braid and the coil 3024 may extend to the proximal end of the extendable segment (100% of the length).

The distal end of the coil 3024 can be spaced proximally from the distal end of the inner liner 3014, for example, to provide room for an annular radiopaque marker 3040. The coil 3024 may be set back proximally from the distal end, in some embodiments, by approximately no more than 1 cm, 2 cm, or 3 cm. In one embodiment, the distal end of the catheter 3000 is provided with a beveled distal surface 3006 residing on a plane having an angle of at least about 10° or 20° and in one embodiment about 30° with respect to a longitudinal axis of the catheter 3000. The radiopaque marker 3040 may reside in a plane that is transverse to the longitudinal axis. Alternatively, at least the distally facing edge of the annular radiopaque marker 3040 may be an ellipse, residing on a plane which is inclined with respect to the longitudinal axis to complement the bevel angle of the distal surface 3006.

After applying the proximal braid 3010, the distal coil 3024, and the RO marker 3040, an outer Jacket 3020 may be applied such as a shrink wrap tube to enclose the catheter body 3000. The outer shrink-wrapped sleeve 3020 may comprise any of a variety of materials, such as polyethylene, polyurethane, polyether block amide (e.g., PEBAX™), nylon or others known in the art. Sufficient heat is applied to cause the polymer to flow into and embed the proximal braid and distal coil.

In one implementation, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 3000 and provide a smooth continuous outer tubular body. The foregoing construction may extend along at least the most distal 10 cm, and preferably at least about the most distal 20 cm, 25 cm, 30 cm, 35 cm, 40 cm, or more than 40 cm of the catheter body 3000. The entire length of the outer shrink wrap jacket 3020 may be formed from tubular segments and the length of the distal tubular segments (e.g., 3022, 3026, 3028, 3030, 3032, 3034, 3036, 3038) may be shorter than the one or more tubular segments forming the proximal portion of the outer shrink wrap jacket 3020 in order to provide steeper transitions in flexibility toward the distal end of the catheter 3000.

The durometer of the outer wall segments may decrease in a distal direction. For example, proximal segments such as 3022 and 3026, may have a durometer of at least about 60D or 70D, with gradual decrease in durometer of successive segments in a distal direction to a durometer of no more than about 35D or 25D or lower. A 25 cm section may have at least about 3 or 5 or 7 or more segments and the catheter 3000 overall may have at least about 6 or 8 or 10 or more distinct flexibility zones. The distal 1 or 2 or 4 or more segments 3036, 3038, may have a smaller OD following shrinking than the more proximal segments 3022-3034 to produce a step down in OD for the finished catheter body 3000. The length of the lower OD section 3004 may be within the range of from about 3 cm to about 15 cm and in some embodiments is within the range of from about 5 cm to about 10 cm such as about 7 or 8 cm, and may be accomplished by providing the distal segments 3036, 3038 with a lower wall thickness.

Figure 5A:
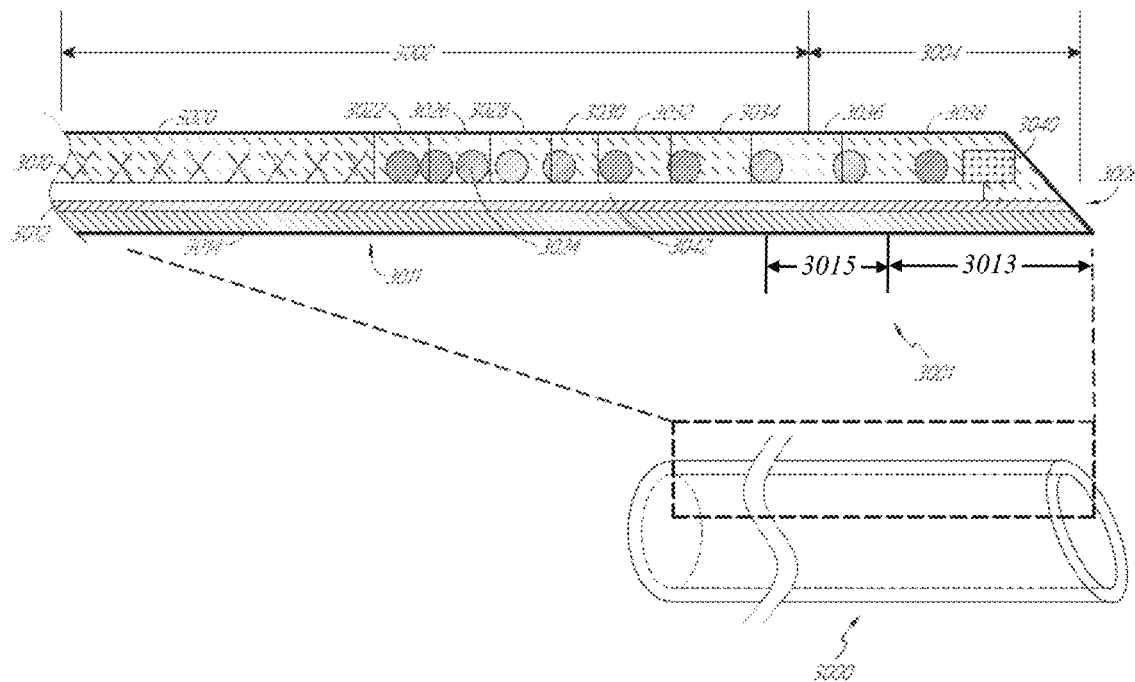
FIG. 5A illustrates a cross-sectional elevational view of a catheter wall according to another embodiment, showing one or more axially extending filaments.
Figure 5B:
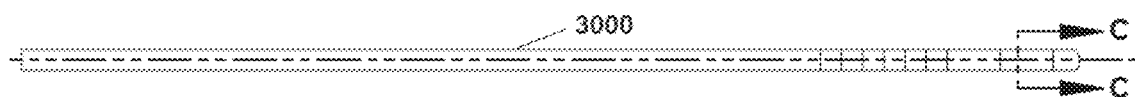
FIG. 5B describes a side elevational view of the catheter of FIG. 5A
Figure 5C:
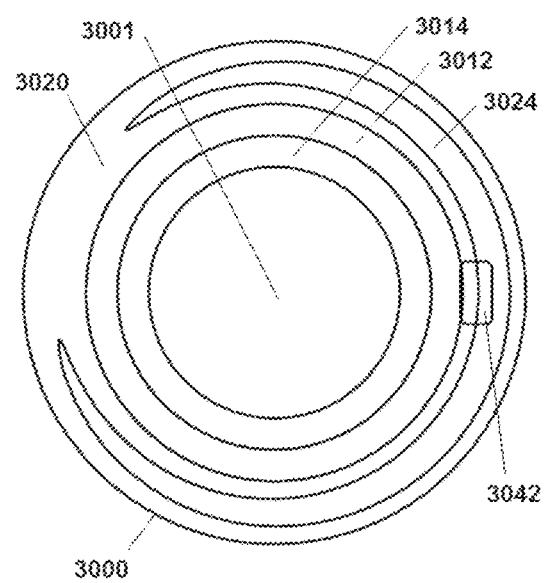
FIG. 5C illustrates a cross-sectional view taken along the line C-C of FIG. 5B, showing one or more axially extending filaments.

Referring to FIGS. 5A-5C, the catheter may further comprise a tension support for increasing the tension resistance in the distal zone. The tension support may comprise a filament and, more specifically, may comprise one or more axially extending filaments 3042. The one or more axially extending filaments 3042 may be axially placed inside the catheter wall near the distal end of the catheter. The one or more axially extending filaments 3042 serve as a tension support and resist elongation of the catheter wall under tension (e.g., when the catheter is being proximally retracted through tortuous vasculature). At least one of the one or more axially extending filaments 3042 may proximally extend along the length of the catheter wall from near the distal end of the catheter to less than about 5 cm from the distal end of the catheter, less than about 10 cm from the distal end of the catheter, less than about 15 cm from the distal end of the catheter, less than about 20 cm from the distal end of the catheter, less than about 25 cm from the distal end of the catheter, less than about 30 cm from the distal end of the catheter, less than about 35 cm from the distal end of the catheter, less than about 40 cm from the distal end of the catheter, or less than about 50 cm from the distal end of the catheter. In some embodiments, at least one of the one or more axially extending filaments 3042 may extend at least a length of the softened or stretched section 3013 of the inner liner 3014 and/or overlap the portion or section 3013 of the inner liner 3014 that is stretched or softened. The one or more axially extending filaments 3042 may have a length greater than or equal to about 50 cm, greater than or equal to about 40 cm, greater than or equal to about 35 cm, greater than or equal to about 30 cm, greater than or equal to about 25 cm, greater than or equal to about 20 cm, greater than or equal to about 15 cm, greater than or equal to about 10 cm, greater than or equal to about 5 cm, greater than or equal to about 45 mm, greater than or equal to about 40 mm, greater than or equal to about 35 mm, greater than or equal to about 30 mm, greater than or equal to about 25 mm, greater than or equal to about 20 mm, greater than or equal to about 15 mm, greater than or equal to about 10 mm, or greater than or equal to about 5 mm. At least one of the one or more axially extending filaments 3042 may have a length less than or equal to about 50 cm, less than or equal to about 40 cm, less than or equal to about 35 cm, less than or equal to about 30 cm, less than or equal to about 25 cm, less than or equal to about 20 cm, less than or equal to about 15 cm, less than or equal to about 10 cm, or less than or equal to about 5 cm, less than or equal to about 45 mm, less than or equal to about 40 mm, less than or equal to about 35 mm, less than or equal to about 30 mm, less than or equal to about 25 mm, less than or equal to about 20 mm, less than or equal to about 15 mm, less than or equal to about 10 mm, or less than or equal to about 5 mm. At least one of the one or more axially extending filaments 3042 may extend at least about the most distal 50 cm of the length of the catheter, at least about the most distal 40 cm of the length of the catheter, at least about the most distal 35 cm of the length of the catheter, at least about the most distal 30 cm of the length of the catheter, at least about the most distal 25 cm of the length of the catheter, at least about the most distal 20 cm of the length of the catheter, at least about the most distal 15 cm of the length of the catheter, at least about the most distal 10 cm of the length of the catheter, at least about the most distal 5 cm of the length of the catheter, at least about the most distal 45 mm of the length of the catheter, at least about the most distal 40 mm of the length of the catheter, at least about the most distal 35 mm of the length of the catheter, at least about the most distal 30 mm of the length of the catheter, at least about the most distal 25 mm of the length of the catheter, at least about the most distal 20 mm of the length of the catheter, at least about the most distal 15 mm of the length of the catheter, at least about the most distal 10 mm of the length of the catheter, or at least about the most distal 5 mm of the length of the catheter.

In some embodiments, at least one of the one or more axially extending filaments 3042 may include an anchoring section 3015, as shown in FIG. 5A, to sufficiently anchor the at least one axially extending filament 3042 into a stiffer or stronger section of the catheter (e.g., a coiled or braided section of the catheter). For example, the anchoring section 3015 of the at least one of the one or more axially extending filaments 3042 may extend a length of about 1 mm to about 15 mm; about 1 mm to about 10 mm; about 1 mm to about 5 mm; about 3 mm to about 5 mm; about 5 mm to about 10 mm; about 3 mm to about 10 mm; about 10 mm to about 20 mm; about 20 mm to about 30 mm; about 30 mm to about 40 mm; about 40 mm to about 50 mm; about 5 cm to about 10 cm; about 10 cm to about 20 cm; about 20 cm to about 30 cm; about 30 cm to about 40 cm; etc. As such, a total length of the at least one axially extending filament 3042 may be about or substantially equal to a length of the softened or stretched portion 3013 of the inner liner 3014 plus a length of the anchoring section 3015 of the at least one axially extending filament 3042. The anchoring section 3015 may anchor at least one of the axially extending filaments in a section of the catheter that includes a helical coil or a braid, for example.

In some embodiments, at least one or the one or more axially extending filaments 3042 extends about or substantially a length of a coil section 3024 of the catheter. For example, at least one axially extending filament 3042 may extend at least about the most distal 50 cm of the length of the catheter, at least about the most distal 45 cm of the length of the catheter, at least about the most distal 40 cm of the length of the catheter, at least about the most distal 35 cm of the length of the catheter, at least about the most distal 30 cm of the length of the catheter, at least about the most distal 25 cm of the length of the catheter, at least about the most distal 20 cm of the length of the catheter, or at least about the most distal 15 cm of the length of the catheter. Further for example, at least one axially extending filament 3042 may extend from the distal end proximally about 5 cm to about 15 cm; about 10 cm to about 20 cm; about 15 cm to about 25 cm; about 20 cm to about 30 cm; about 25 cm to about 35 cm; about 30 cm to about 40 cm; about 35 cm to about 45 cm; or about 40 cm to about 50 cm. The one or more axially extending filaments 3042 may be placed near or radially outside the tie layer 3012 or the inner liner 3014. The one or more axially extending filaments 3042 may be placed near or radially inside the braid 3010 and/or the coil 3024. The one or more axially extending filaments 3042 may be carried between the inner liner 3014 and the helical coil 3024.

When more than one axially extending filaments 3042 are placed in the catheter wall, the axially extending filaments 3042 may be placed in a radially symmetrical manner. For example, the angle between the two axially extending filaments 3042 with respect to the radial center of the catheter may be about 180 degree. Alternatively, depending on desired clinical performances (e.g., flexibility, trackability), the axially extending filaments 3042 may be placed in a radially asymmetrical manner. The angle between any two axially extending filaments 3042 with respect to the radial center of the catheter may be less than about 180 degree, less than or equal to about 165 degree, less than or equal to about 150 degree, less than or equal to about 135 degree, less than or equal to about 120 degree, less than or equal to about 105 degree, less than or equal to about 90 degree, less than or equal to about 75 degree, less than or equal to about 60 degree, less than or equal to about 45 degree, less than or equal to about 30 degree, less than or equal to about 15 degree, less than or equal to about 10 degree, or less than or equal to about 5 degree.

The one or more axially extending filaments 3042 may be made of materials such as Kevlar, Polyester, Meta-Para-Aramide, or any combinations thereof. At least one of the one or more axially extending filaments 3042 may comprise a single fiber or a multi-fiber bundle, and the fiber or bundle may have a round or rectangular cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more axially extending filaments 3042, as measured in the radial direction, may be no more than about 1%, 2%, 3%, 4%, 5%, 6%, 7%, 8%, 9%, 10%, 11%, 12%, 13%, 14%, 15%, 20%, 25%, or 30% of that of the catheter 3000. The cross-sectional dimension of the one or more axially extending filaments 3042, as measured in the radial direction, may be no more than about 0.001 inches, about 0.002 inches, about 0.003 inches, about 0.004 inches, about 0.005 inches, about 0.006 inches, about 0.007 inches, about 0.008 inches, about 0.009 inches, about 0.010 inches, about 0.015 inches, about 0.020 inches, about 0.025 inches, or about 0.030 inches.

The one or more axially extending filaments 3042 may increase the tensile strength of the distal zone of the catheter to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 6A:
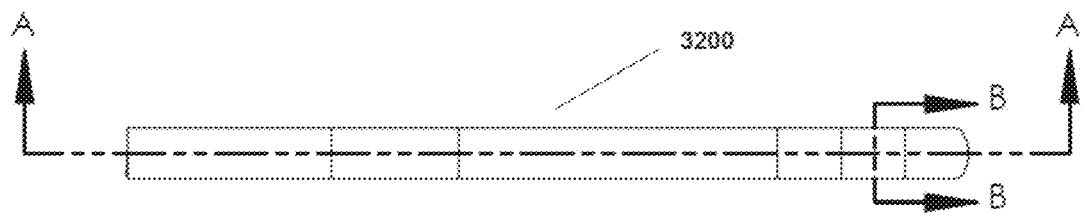
FIG. 6A illustrates a side elevational view of a progressively enhanced flexibility catheter according to an embodiment.
Figure 6B:
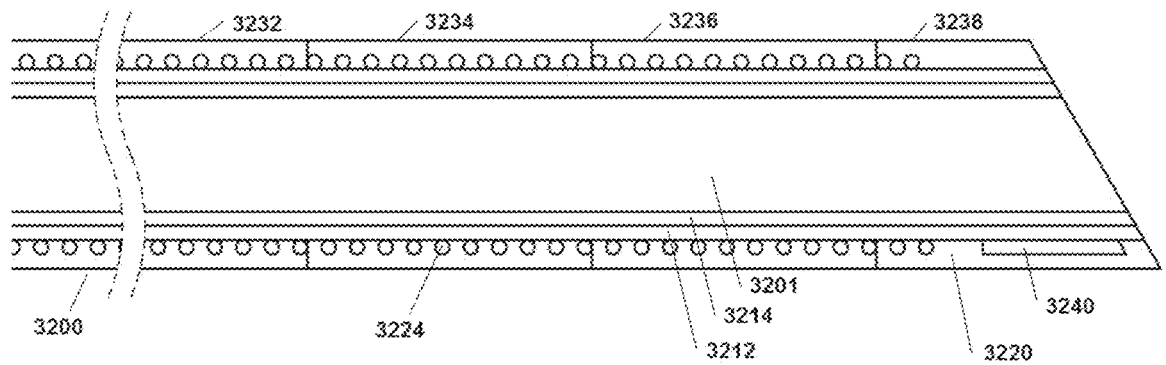
FIG. 6B is a proximal end view of the enhanced flexibility catheter of FIG. 6A.
Figure 6C:
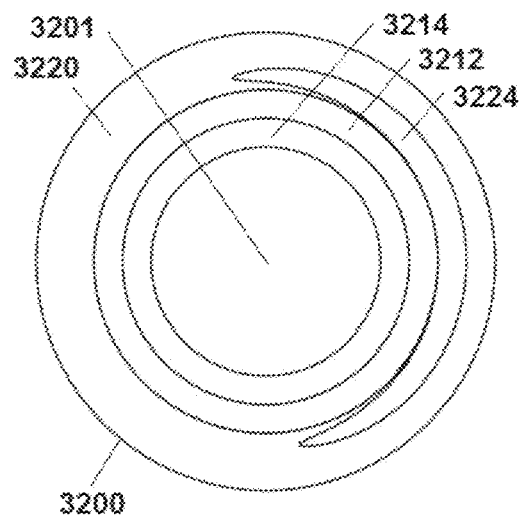
FIG. 6C illustrates a cross-sectional view taken along the line B-B of FIG. 6A.

Referring to FIGS. 6A-6C, depending on whether the catheter 3000 is able to navigate sufficiently distally to reach the target site, an intraluminal catheter 3200 such as a telescopic extension segment having a proximally extending control wire as has been described elsewhere herein (e.g., distal segment 34 in FIGS. 3A and 3B) may be inserted through the catheter 3000 from the proximal end of the catheter 3000. The intraluminal catheter 3200 is inserted such that the distal end of the intraluminal catheter 3200 reaches further distally beyond the distal end of the catheter 3000. The outer diameter of the intraluminal catheter 3200 is smaller than the inner diameter of the catheter 3000. This way, the intraluminal catheter 3200 can slide inside the lumen of the catheter 3000.

The intraluminal catheter 3200 incorporates characteristics of the side wall construction of the catheter 3000 described herein. The axial length of the tubular extension segment may be less than about 50% and typically less than about 25% of the length of the catheter 3000. The axial length of the tubular extension segment will generally be at least about 10 cm or 15 cm or 20 cm or 25 cm or more but generally no more than about 70 cm or 50 cm or 30 cm.

Figure 7A:
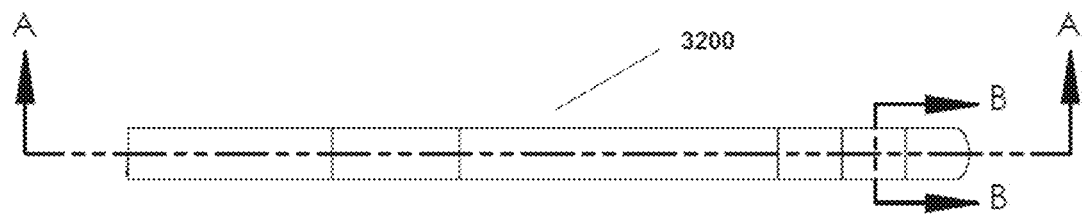
FIG. 7A depicts a side elevational view of a catheter according to another embodiment.
Figure 7B:
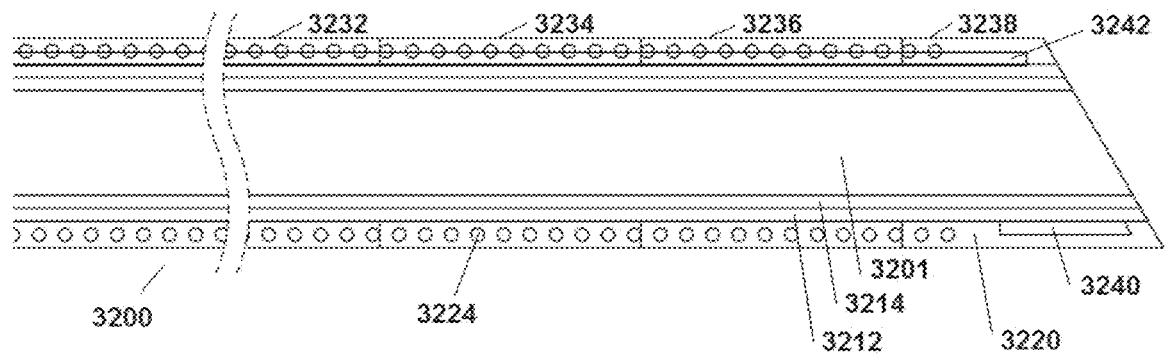
FIG. 7B describes a cross-sectional elevational view taken along the line A-A of FIG. 7A, showing one or more axially extending filaments.
Figure 7C:
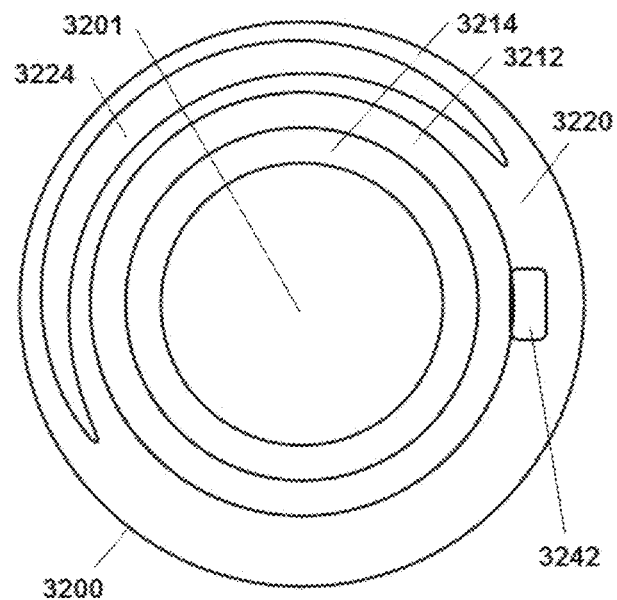
FIG. 7C illustrates a cross-sectional view taken along the line B-B of FIG. 7A, showing one or more axially extending filaments.

Referring to FIGS. 7A-7C, the intraluminal catheter 3200 may have one or more axially extending filaments 3242. The one or more axially extending filaments 3242 incorporate characteristics of the one or more axially extending filaments 3042 of the catheter 3000, except the cross-sectional dimension as measured in the radial direction of the one or more axially extending filaments 3242 of the intraluminal catheter 3200 may be less than the corresponding dimension of the filament 3042 in the catheter 3000.

Figures 8A, 8B:
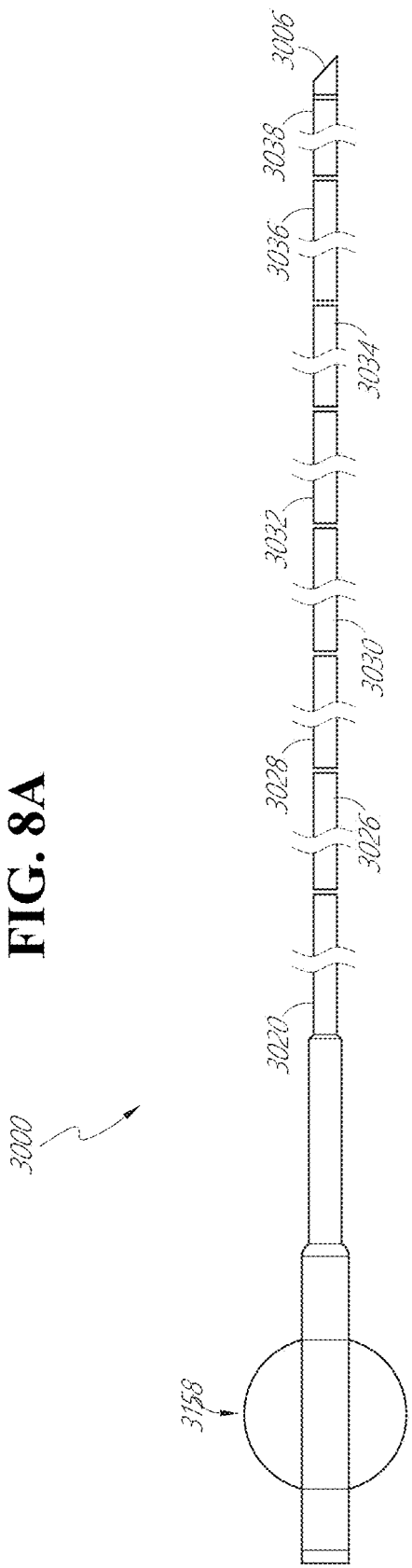
FIG. 8A illustrates a side elevational view of a progressively enhanced flexibility catheter according to an embodiment.
FIG. 8B is a proximal end view of the enhanced flexibility catheter of FIG. 8A.

Referring to FIGS. 8A-8B, there is illustrated one example of an outer jacket segment stacking pattern for a progressive flexibility catheter of the type discussed in connection with FIG. 4. A distal segment 3038 may have a length within the range of about 1-3 cm, and a durometer of less than about 35D or 30D. An adjacent proximal segment 3036 may have a length within the range of about 4-6 cm, and a durometer of less than about 35D or 30D. An adjacent proximal segment 3034 may have a length within the range of about 4-6 cm, and a durometer of about 35D or less. An adjacent proximal segment 3032 may have a length within the range of about 1-3 cm, and a durometer within the range of from about 35D to about 45D (e.g., 40D). An adjacent proximal segment 3030 may have a length within the range of about 1-3 cm, and a durometer within the range of from about 50D to about 60D (e.g., about 55D). An adjacent proximal segment 3028 may have a length within the range of about 1-3 cm, and a durometer within the range of from about 35D to about 50D to about 60D (e.g., about 55D). An adjacent proximal segment 3026 may have a length within the range of about 1-3 cm, and a durometer of at least about 60D and typically less than about 75D. More proximal segments may have a durometer of at least about 65D or 70D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10D, preferably at least about 20D and in some implementations at least about 30D or 40D or more.

In another embodiment, the most distal portion of the catheter 3000 may comprise a durometer of less than approximately 35D (e.g., 25D) to form a highly flexible distal portion of the catheter and have a length between approximately 25 cm and approximately 35 cm. In other embodiments, the length may be between approximately 15 cm and approximately 25 cm. The distal portion may comprise one or more tubular segments of the same durometer (e.g., segment 3038) or of different durometers. In some embodiments, one or more of the distal most segments may comprise a polyether-based thermoplastic polyurethane (e.g., Tecothane®). More proximal segments may comprise a polyether block amide (e.g., PEBAX®). A series of proximally adjacent tubular segments to the distal portion may form a transition region between a proximal stiffer portion of the catheter 3000 and the distal highly flexible portion of the catheter. The series of tubular segments forming the transition region may have the same or substantially similar lengths, such as approximately 1 cm. The relatively short length of the series of tubular segments may provide a steep drop in durometer over the transition region. For example, the transition region may have a proximal tubular segment 3036 (proximally adjacent the distal portion) having a durometer of approximately 35D. An adjacent proximal segment 3034 may have a durometer of approximately 55D. An adjacent proximal segment 3032 may have a durometer of approximately 63D. An adjacent proximal segment 3030 may have a durometer of approximately 72D. One or more of the segments within the transition region may comprise a length between about 1 and 4 cm. For example, the transition region may comprise a proximal segment 3036 approximately 4 cm and 35D, an adjacent segment 3034 approximately 3 cm and 37D, an adjacent segment 3032 approximately 1 cm and 47D, an adjacent segment 3030 approximately 1 cm and 55D, an adjacent segment 3028 approximately 1 cm and 63D, and an adjacent segment 3026 approximately 1 cm and 72D. In some embodiments, the length of the distal portion of the catheter 3000, including the highly flexible distal portion and the transition region, may be between about 25-30 cm, between about 30-35 cm, between about 35 to 40 cm, or between about 40-45 cm. More proximal segments may comprise a durometer or durometers greater than approximately 72D and may extend to the proximal end of the catheter or extension catheter segment. For instance, an extension catheter segment may comprise a proximal portion greater than approximately 72D between about 1 cm and about 3 cm. In some embodiments, the proximal portion may be about 2 cm long. In some embodiments, the most distal segments (e.g., 3038-3030) or at least the transition region may comprise PEBAX® and more proximal segments may comprise a generally stiffer material, such as Vestamid®.

The inner diameter of the catheter 3000 or catheter extension segment may be between approximately 0.06 and 0.08 inches, between approximately 0.065 and 0.075 inches, or between 0.068 and 0.073 inches. In some embodiments, the inner diameter is approximately 0.071 inches. In some embodiments, the distal most portion may taper to a decreased inner diameter as described elsewhere herein. The taper may occur approximately between the distal highly flexible portion and the transition region (e.g., over the most proximal portion of the distal highly flexible portion). The taper may be relatively gradual (e.g., occurring over approximately 10 or more cm) or may be relatively steep (e.g., occurring over less than approximately 5 cm). The inner diameter may taper to an inner diameter between about 0.03 and 0.06 inches. For example, the inner diameter may be about 0.035 inches, about 0.045 inches, or about 0.055 inches at the distal end of the catheter 3000. In some embodiments, the inner diameter may remain constant, at least over the catheter extension segment. In some embodiments, the coil 3024 may extend from a distal end of the catheter 3000 along the highly flexible distal portion ending at the distal end of the transition region. In other embodiments, the coil 3024 may extend from a distal end of the catheter to the proximal end of the transition region, to a point along the transition region, or proximally beyond the transition region. In other embodiments, the coil 3024 may extend the entire length of the catheter 3000 or catheter extension segment as described elsewhere herein. The braid 3010, when present, may extend from the proximal end of the coil 3024 to the proximal end of the catheter 3000 or catheter extension segment.

Figure 9:
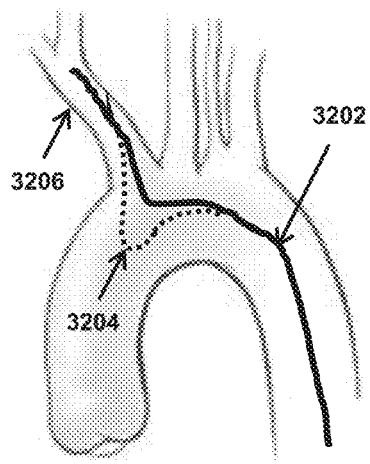
FIG. 9 illustrates back-up support of the catheter in accordance with the present invention.

Performance metrics of a catheter include back-up support, trackability, pushability, and kink resistance. Back-up support means ability of the catheter to remain in position within anatomy and provide a stable platform through which endoluminal devices may advance. Referring to FIG. 9, when the devices are pushed through the catheter 3202, if there is not enough back-up support in the catheter 3202, the distal portion 3204 of the catheter 3202 may prolapse, pull out, or back out of a vessel 3206 that branches out of a main blood vessel (e.g., brachiocephalic artery 82, common carotid artery 80, or subclavian artery 84). Back-up support for the catheter 3202 may be improved by providing a proximal region with high durometer or modulus and a distal region with low durometer or modulus. Durometer or modulus of the proximal region of the catheter 3202 may be improved by braid reinforcement. The region of the catheter at which durometer or modulus is strengthened may be placed near branching points at which the aortic arch 1114, 1214 branches into brachiocephalic artery 82, common carotid artery 80, or subclavian artery 84 or near other anatomical structures (i.e., branching points) at which a main vessel branches into one or more smaller vessels, providing an opportunity for a catheter with poor back-up support to prolapse. For example, the region of the catheter at which durometer or modulus is strengthened may be placed within about 0.5 cm, about 1 cm, about 2 cm, about 3 cm, about 4 cm, about 5 cm, or about 6 cm from a branching point at which a main vessel branches into one or more smaller vessels.

Trackability means ability of the catheter to track further distally than other catheters (e.g., to M1). For example, a catheter that can reach a cerebral segment of the internal carotid artery (ICA) has better trackability than a catheter that can reach a cavernous or petrous segment of the ICA. Trackability of the catheter may be improved by using a catheter wall with low durometer or modulus or by adding a coating (e.g., a hydrophilic coating) on at least a portion of the catheter wall. In one embodiment, the hydrophilic coating may be placed along the distal most region of the catheter. The hydrophilic coating on the catheter may extend to about 1 cm, about 5 cm, about 10 cm, about 15 cm, or about 20 cm from the distal end of the catheter. The region with lower durometer or modulus may locate at the distal most region of the catheter. The region with lower durometer or modulus may extend to about 1 cm, about 5 cm, about 10 cm, about 15 cm, or about 20 cm from the distal end of the catheter.

Pushability means rigidity of the catheter sufficient to push through anatomy without "buckling". Pushability of the catheter may be improved by increasing its durometer or modulus. Pushability of the catheter may also be improved by providing a proximal region with high durometer or modulus and a distal region with low durometer or modulus. A transition region of the catheter in which durometer or modulus changes along its longitudinal length (e.g., decreasing durometer or modulus from the proximal end to the distal end) may begin at about 50%, 60%, 70%, 75%, 80%, or more of the length of the catheter from its proximal end.

Kink resistance means resistance of the catheter to kinking. In addition, if the catheter does kink, kink resistance of the catheter helps it return to its original shape. Kink resistance is important in the distal segment of the catheter, which is more prone to kinking than the proximal segment. Kink resistance of the catheter may be improved by adding one or more NiTi coils (or a coil at least portion of which is Nitinol) to the catheter wall.

Figure 10:
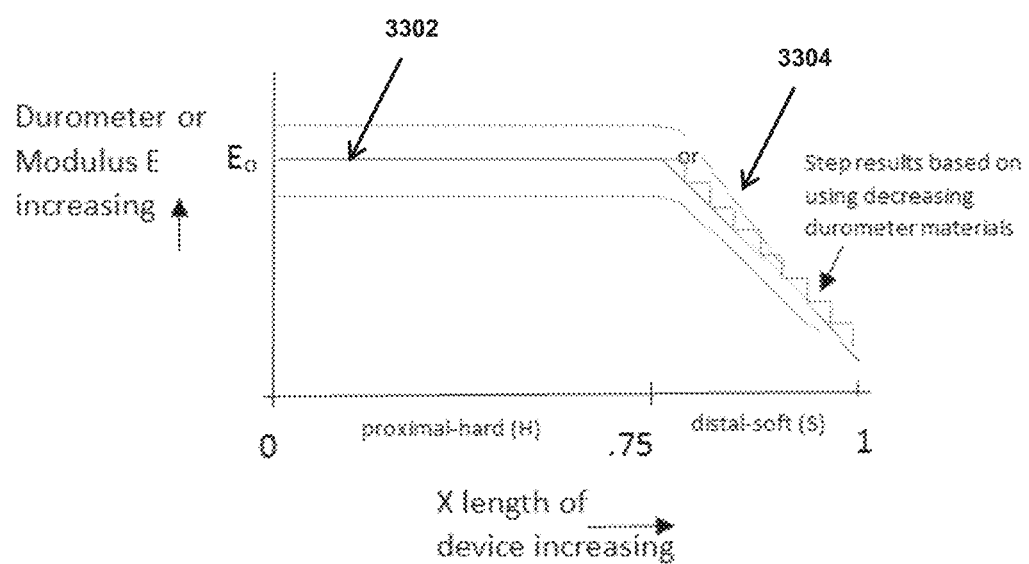
FIG. 10 depicts a graph of modulus or durometer of the catheter along the length of the catheter, from the proximal end to the distal end.

FIG. 10 describes a graph of durometer or modulus of a catheter in accordance with the present invention along the length of the catheter, from the proximal end (x=0) to the distal end (x=1). The catheter according to an embodiment may have a decreasing durometer or modulus (E) approaching its distal end. The proximal end of the catheter has higher durometer or modulus than that of the distal end of the catheter. High durometer or modulus near the proximal end provides superior back-up support of the catheter. Durometer or modulus of the catheter is substantially constant along its length near the proximal end 3302 of the catheter. Then, durometer or modulus of the catheter decreases near the distal end 3304 of the catheter. Durometer or modulus of the catheter may begin to decrease (i.e., transition region) at about 50%, 70%, 75%, 80%, or 90% of the length of the catheter from its proximal end. The catheter may have successively decreasing durometer or modulus near its distal end by using materials with less durometer or modulus or having a thinner catheter wall near the distal end. Decreased durometer or modulus near the distal end provides superior trackability of the catheter.

Catheters according to the present invention have a flexural load that is substantially constant along the longitudinal length near the proximal end and a rapidly decreasing flexural load near the distal end. In a catheter having a length of about 125 cm, the catheters may have a flexural load greater than or equal to about 1.0 lbF, about 1.5 lbF, about 2.0 lbF, about 2.5 lbF, about 3.0 lbF, or about 3.5 lbF at about 85 cm from the proximal end. The catheters may have a flexural load less than or equal to about 2.5 lbF, about 2.0 lbF, about 1.5 lbF, about 1.0 lbF, or about 0.5 lbF at about 95 cm from the proximal end. The catheters may have a flexural load less than or equal to about 1.5 lbF, about 1.0 lbF, about 0.75 lbF, about 0.5 lbF, about 0.25 lbF, or about 0.1 lbF at about 105 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 115 cm from the proximal end. For catheters having different lengths, the foregoing dimensions can be scaled from the distal end of the catheter as a percentage of catheter length.

In certain implementations constructed in accordance with FIG. 4, the flexural load is less than about 3.0 or 3.25 lbF at 65 cm from the proximal end and greater than about 2.25 or 2.5 lbF on average from 65 cm to 85 cm from the proximal end. Flexural load drops to no more than about 1.0 and preferably no more than about 0.5 lbF at about 95 cm from the proximal end. This provides enhanced backup support in the aorta while maintaining enhanced trackability into the distal vasculature.

In other embodiments, the catheters may have a flexural load greater than or equal to about 1.0 lbF, about 1.5 lbF, about 2.0 lbF, about 2.5 lbF, about 3.0 lbF, or about 3.5 lbF at about 60 cm from the proximal end. The catheters may have a flexural load less than or equal to about 2.0 lbF, about 1.5 lbF, about 1.0 lbF, or about 0.5 lbF at about 70 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 80 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 90 cm from the proximal end.

The catheters may have a transition region, in which its flexural load changes by greater than or equal to about 1.0 lbF, about 1.5 lbF, about 2.0 lbF, about 2.5 lbF, about 3.0 lbF, or about 3.5 lbF. The longitudinal length of the transition region may be less than or equal to about 20 cm, about 15 cm, about 10 cm, about 5 cm, about 3 cm, or about 1 cm.

Figure 11:
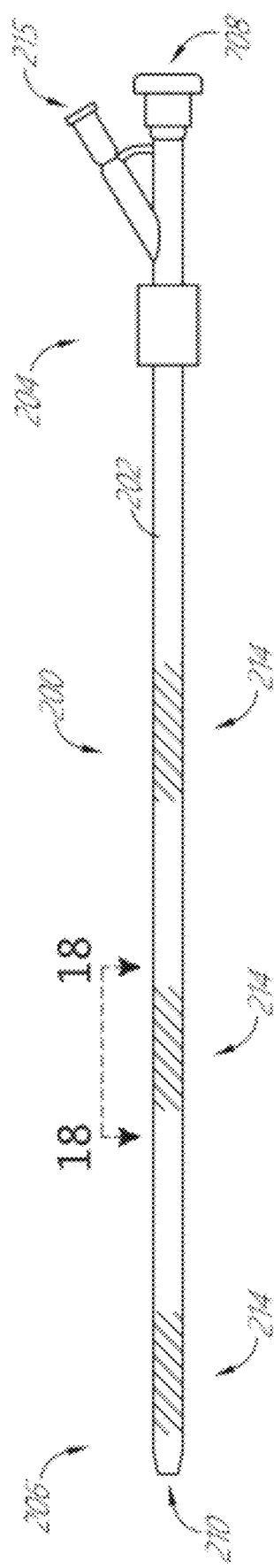
FIG. 11 is a side elevational schematic view of a transformable catheter in accordance with the present invention.

Referring to FIG. 11, there is illustrated a transformable access sheath 200. The access sheath 200 comprises an elongate flexible tubular body 202 extending between a proximal end 204 and a distal end 206. A proximal access port 208 is in communication with a distal port 210 on the distal end 206 by way of a central lumen 212.

At least one transition zone 214 is provided on the tubular body 202. Transition zone 214 is controllably transformable between a relatively stiff configuration and a relatively flexible configuration. The access sheath 200 may be distally advanced through tortuous anatomy with at least one transition zone 214 in a relatively stiff configuration as desired such as to provide column strength or to facilitate the introduction of instruments therethrough. The transition zone 214 may be controllably transformed to a relatively flexible configuration as desired, such as to navigate tight bends in the vasculature.

In the illustrated embodiment, three transition zones 214 are shown. However, one or two or three or four or more transition zones may be utilized, depending upon the desired clinical performance. The transition zone 214 may be from about 1 cm to about 20 or 30 cm or more in length. In certain embodiments, the transition zones will be within the range of from about 2 cm to about 10 cm in length. The length and location of the transition zones may depend upon the target anatomy for the access catheter and can be located accordingly.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

Intravenous catheters may comprise regions of different flexibility in order to modulate the bending flexibility, tensile stiffness, trackability, pushability, and/or other structural properties of the catheter. Various embodiments for modifying catheters to comprise localized regions of variable mechanical properties are disclosed herein. Creating localized regions of variable mechanical properties in a catheter may improve the safety, performance, reliability, and/or ease of placing the catheter in the desired location in the vasculature, particularly for neurovascular applications.

Figure 12A:
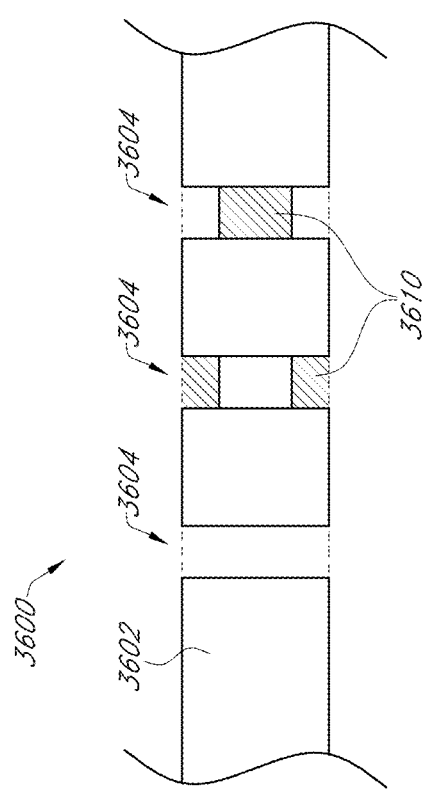
FIG. 12A schematically illustrates a portion of a sidewall comprising through-holes for modulating the mechanical properties of the catheter.
Figure 12B:
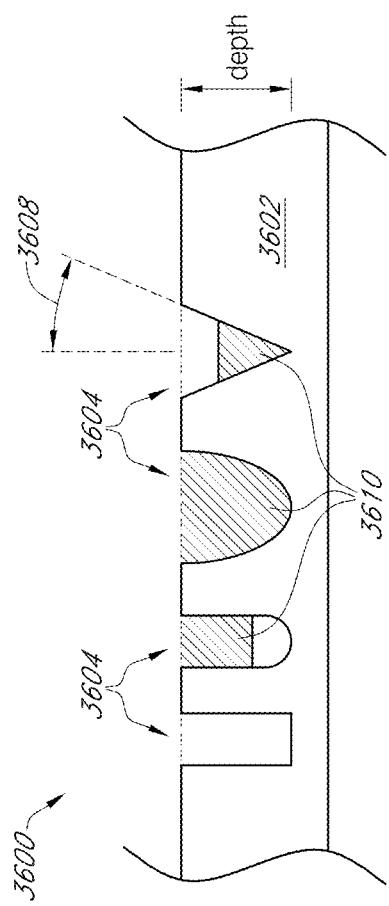
FIG. 12B schematically illustrates a portion of a sidewall comprising blind holes for modulating the mechanical properties of the catheter.
Figure 12C:
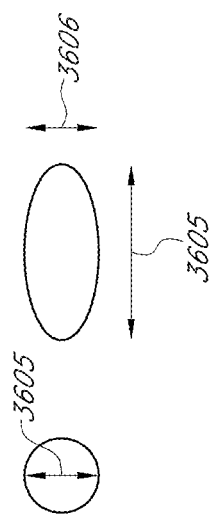
FIG. 12C schematically illustrates example shapes of two holes disposed on the sidewall of a catheter.

In some embodiments, the bending stiffness and/or tensile stiffness is locally reduced, in other words the region is softened, over a region of the catheter 3600 by incorporating a plurality of holes 3604 disposed within a sidewall 3602 of the catheter. Catheter 3600 may be the same or may comprise any of the same or similar features as other catheters (e.g., catheter 10, catheter 3000) described elsewhere herein. FIGS. 12A-12B schematically illustrates cross-sections of a portion of the sidewall 3602 of catheter 3600. The holes 3604 may extend entirely through the sidewall (i.e., through-holes), as depicted in FIG. 12A, or may extend from a surface of the sidewall partially into but not entirely through the sidewall (i.e., blind holes), as depicted in FIG. 12B. For instance, the holes 3604 may extend a depth of at least 5-10%, 10-20%, 20-50%, 50-90%, or 90-100% of the thickness of the catheter sidewall 3602. The blind holes 3604 may extend from an outer diameter of the catheter or an inner diameter of the catheter, or some blind holes 3605 may extend from each side. In some embodiments, the catheter 3600 may comprise both through-holes 3605 and blind holes 3604. The holes 3604 may comprise circular, ellipsoidal, oblong, rectangular, square, polygonal, triangular, and/or irregular shaped openings (e.g., cross-sections). FIG. 12C schematically depicts two example shapes of the hole 3604 openings. As schematically, depicted in FIG. 12C, the holes 3604 may comprise diameters (or largest dimension 3605 across the opening) of approximately 1-5 μm, 5-10 μm, 10-15 μm, 15-30 μm, less than 1 μm, or more than 30 μm. The holes 3604 may comprise a dimension 3606 transverse (i.e. perpendicular) to the largest dimension 3605 which forms an aspect ratio of the two dimensions 3606:3605. In some embodiments, the transverse dimension 3606 may be the smallest dimension across the opening. The aspect ratio of 3606:3605 may be between 1:1 and 1:1.5, between 1:1.5 and 1:1.75; between 1:1.75 and 1:2; between 1:2 and 1:3; between 1:3 and 1:5: between 1:5 and 1:10, or more than 1:10. The shape and/or aspect ratio of the hole 3604 may be chosen to selectively deform the catheter in one or more directions under applied stress (e.g., bending, torsion, and/or radial stress) to allow for distinct ex vivo and in vivo behavior. The holes 3604 may be sized to prevent cells (e.g., blood cells) and potentially fluid from passing into or through the holes 3604. The small size of the holes 3604 combined with intermolecular forces (e.g., steric hindrance, hydrophobic interactions, surface tension, etc.) between the fluid and/or blood components and the catheter may prevent or inhibit the passage of the fluid and/or blood components, even under negative pressure applied through the internal lumen of the catheter 3600.

The holes 3604 may each comprise an axis extending through a center of the opening along a depth of the hole. The axes may be substantially aligned along a purely radial direction of the catheter 3600 or may be at least partially off-radius (e.g., comprising a circumferential component and/or a proximal-distal axial component in addition to a radial component). In some embodiments, the holes 3604 may comprise a substantially uniform cross section. For example, a hole 3604 having a circular opening may be substantially cylindrical in shape (e.g., left hole 3604 in FIG. 12B). Blind holes 3604 may have substantially flat closed ends opposite the openings (left hole 3604 in FIG. 12B) or may comprise rounded or partially rounded closed ends (e.g., middle left hole 3604 in FIG. 12B). Through-holes 3604 may comprise symmetric openings on the inner and outer diameter of the catheter (e.g., hole 3604 in FIG. 12A). In some embodiments, the cross section of a hole 3604 may not be substantially uniform. For example, the cross-section may increase or decrease across a depth of the hole (e.g., taper). For instance, a hole may comprise a substantially conical shape (e.g., right hole in FIG. 12B). The change in dimension may be continuous or stepped. The taper along the depth of the hole 3604 or at least along a portion of the hole 3604, such as adjacent the opening, may be measured by an angle 3608 relative to the central axis, as shown in FIG. 12B. The taper angle 3608 may be between 0-15 degrees, between 15-30 degrees, between 30-45 degrees, between 45-60 degrees, or greater than 60 degrees. The change in dimension may be gradual (e.g., constant) or may be sharp. In some embodiments, the cross-section of a hole 3604 may change shape along the depth of the hole. For example, a through-hole 3604 may comprise a circular opening on one side and an elliptical opening on the opposite side. The plurality of holes 3604 may comprise the same dimensions and/or alignments or may comprise different dimensions and/or alignments.

The holes 3604 may be formed in the catheter 3600 in any suitable manner. The holes 3604 may be perforations. In some embodiments, the perforations may be made by mechanical means, such as puncturing or drilling, or by a laser (e.g., laser drilling) after the catheter 3600 has been fabricated. In some embodiments, the holes 3604 may be formed during fabrication (e.g., during extrusion) of the catheter 3600. The holes 3604 may be molded into the catheter 3600. In embodiments in which the sidewall 3602 of the catheter 3600 comprises multiple layers (e.g., an inner liner, a main body, and/or an outer jacket), such as described elsewhere herein, the holes 3604 may be formed through all layers and/or through only some of the layers (e.g., to form a blind hole 3604). For example, any of the described embodiments (e.g., FIGS. 12A-13I) may be formed in a portion of or a section of any one or more of: an inner liner, a main body, an outer jacket, or a combination thereof to soften the catheter, at least at that region or section, and/or enhance flexibility of the catheter. Further, any combination of applying holes to a catheter section and/or elongating or stretching an inner liner of the catheter may be used to enhance flexibility of the catheter, at least at that section. For example, one or more of the following may be used to enhance flexibility and/or soften the catheter: stretching at least a portion of the inner liner, adding holes to at least a portion of the inner liner, outer lamination, or a combination thereof.

In some embodiments, as shown in FIGS. 12A-12B, the holes 3604 may be filled with one or more additive fillers 3610. The filler 3610 may modify (e.g., increase) the local stiffness of the catheter 3600 at and locally around the hole 3604. The filler 3610 may entirely fill the volume of the hole 3604 (e.g., middle right hole in FIG. 12B) or may partially fill the volume of the hole (e.g., right hole 3604 in FIG. 12B). In embodiments, where a blind hole 3604 is partially filled, the filler 3610 may be disposed within a volume substantially proximate the opening of the hole 3604 (e.g., middle left hole 3604 in FIG. 12B), the filler 3610 may be disposed within a volume substantially proximate the closed end of the hole 3604 (e.g., right hole 3604 in FIG. 12B), or the filler 3610 may be disposed within a volume intermediate the opening and the closed end. In embodiments where a through-hole 3604 is partially filled, the filler 3610 may be disposed within a volume or volumes substantially proximate the openings of the hole or may be disposed within one or more volumes intermediate the openings (e.g. right hole 3604 in FIG. 12A). In either blind or through-holes 3604, the filler 3610 may be disposed near both the openings/closed ends, leaving a void volume between (e.g., middle hole 3604 in FIG. 12A). Any combination of the disposition of the fillers 3610 may be employed.

The addition of a filler 3610 may increase the stiffness (e.g., bulk modulus) relative to the hole comprising a void space (no filler). The filler 3610 may comprise a material that has a stiffness greater than the material forming the body of the catheter 3600 (e.g., the sidewall 3602 through which the hole is formed), substantially the same as the material forming the body of the catheter 3600, or less than the material forming the body of the catheter 3600. Thus, the filled hole 3604 may effectively increase or decrease the local stiffness of the catheter 3600. In some embodiments, the filler 3610 may comprise a thermoplastic elastomer, such as a polyether block amide (e.g., Pebax®) or other polymers comprising polyethers and polyamides. The incorporation of polyethers may generally decrease the flexibility of the filler 3610. The incorporation of polyamides may generally increase the stiffness of the filler 3610. The filler 3610 may comprise a thermoplastic polyurethane elastomer, such as a polyether-based thermoplastic polyurethane (e.g., Tecothane®). Examples of suitable high durometer Pebax® materials which may be used to increase the stiffness of the catheter may include, but are not limited to, Pebax® 4533, 55533, and 6333. Examples of suitable Tecothane® materials which may be used to increase the stiffness of the catheter may include, but are not limited to, Tecothane® 1075D, 2055D, and 2065D. The fillers 3610 may comprise the same or different types of materials (e.g., polyether block amides) as the sidewall 3602 of the catheter 3610. For instance, the catheter may comprise Pebax® 4533, 533, or 6333; Tecoflex® EG-60D, EG-65D, EG-72D, EG-80A; or any other suitable medical grade thermoplastic. The fillers 3610 disclosed herein may be combined with any of the other disclosed fillers or any other suitable filler. In some embodiments, the filler 3610 may be formed from an outer layer, coating, or jacket (e.g., PTFE, Pebax®, Tecothane®, etc.) which is heated to cause the jacket material to flow, at least partially, into the hole 3604.

The filler 3610 may comprise a gel (e.g., a hydrogel), a colloid, an emulsion, and/or a coacervation. In some embodiments, the filler 3610 may comprise a viscoelastic material. The viscoelastic material may comprise strain-sensitive properties (e.g., thixotropic or rheopectic). The filler 3610 may comprise strain-rate sensitive properties. The viscoelastic material may comprise a strain-thickening material (dilatant), such as polyethylene glycol, and/or a strain-thinning material (pseudoplastic), such as blood.

The filler 3610 may comprise bioactive and/or chemically active additives. For example, the filler 3610 may comprise additives which are pH-sensitive, sensitive to hydrolysis or otherwise reactive to water, reactive to blood plasma or soluble blood factors, reactive to blood cells (e.g., red blood cells), biologically degradable, soluble, and/or otherwise reactive to the physiological vascular environment, including intravascular molecules, such that the physical properties of the catheter may change, reversibly or irreversibly, when the catheter 3600 is inserted into the blood stream. The physical effects on the catheter 3600 may comprise an increase or decrease in the bending or tensile stiffness/flexibility of the catheter 3600. For instance, an additive may dissolve when subjected to the aqueous vascular environment. As the additive dissolves, the filler 3610 may become less dense and the stiffness near the hole 3604 comprising the filler 3610 may decrease. In some embodiments, the filler 3610 may comprise additives which are cross-linked and/or undergo a condensation reaction, which may increase the stiffness around the hole 3604 comprising the filler 3610. In some embodiments, the filler 3610 may comprise a poloxamer, or another polymer with surfactant properties. The poloxamer may form a hydrogel in the presence of water which may increase the stiffness of the catheter 3600.

The catheter 3600 may be differentially processed along various lengths and/or regions to produce lengths or regions comprising different physical properties, such as tensile and/or bending stiffness. For example, the catheter 3600 may be thermally and/or photonically treated to alter the chemical structure of the sidewall 3602. The treatment may affect one or more layers of the material the actual sidewall 3602 is fabricated from and/or it may affect fillers 3610 occupying holes 3604 within the sidewall 3602 of the catheter 3600. The treatment may break, cross-link, and/or reorient polymer chains or initiate and/or catalyze another chemical reaction, including those described elsewhere herein. In some embodiments, the catheter 3600 may be processed externally to the body. In some embodiments, the catheter 3600 may be processed in vivo. For instance, a radiation that penetrates the body (e.g., a prescribed wavelength) may be applied from outside the body to a portion of the catheter 3600 positioned within a certain region of the body. In some embodiments, the treatment may be applied by a laser (e.g., a short-pulse laser). The laser or other light source may apply light of a certain wavelength (e.g., UVA, UVB, etc.) as appropriate for the desired reaction. The processing may be performed, before, during, and/or after various steps of the catheter fabrication (e.g., forming holes 3604).

Figure 12D:
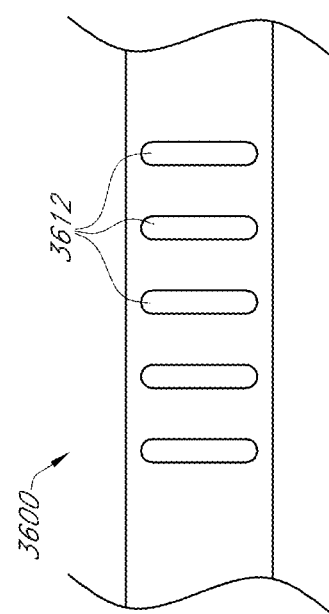
FIG. 12D schematically depicts a side view of a portion of a catheter comprising notches for modulating the bending of the catheter.
Figure 12E:
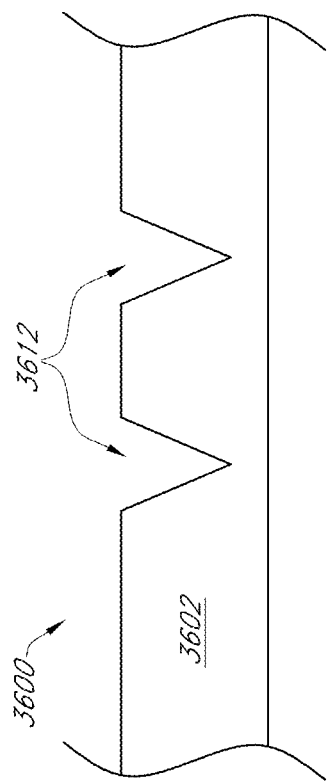
FIG. 12E schematically depicts a cross-section of a portion of a catheter comprising a plurality of axially-spaced notches.
Figure 12F:
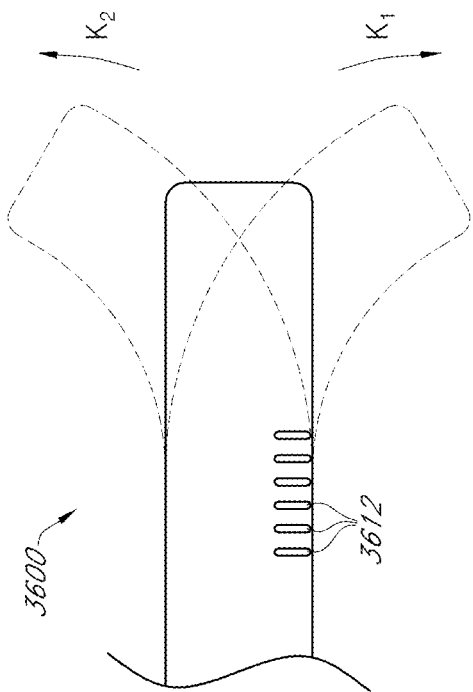
FIG. 12F schematically illustrates the bending of a distal end of a catheter comprising a plurality of notches disposed on one lateral side of the catheter.

In some embodiments, a hole 3604 may be configured as a notch 3612. FIGS. 12D-12F schematically illustrate examples of notches 3612 in the sidewall 3602 of the catheter 3600. FIG. 12D schematically depicts a side view of a portion of the catheter 3600 comprising notches 3612. Notches 3612 may comprise generally elongate shapes (large aspect ratios). Notches 3612 may extend generally circumferentially around at least a portion of the circumference of the catheter 3600. Notches 3612 may be formed as through-holes 3604 or as blind holes 3604. FIG. 12E schematically depicts a cross-section of a portion of the sidewall 3602 comprising a plurality of notches 3612. In some embodiments, notches 3612 formed as blind holes 3604 may comprise triangular cross-sections relative to a circumferential axis, as shown in FIG. 12E. The triangular cross-section may promote bending of the catheter 3600 along a side of the catheter 3600 comprising the notches 3612. FIG. 12F schematically illustrates the bending of a distal end of a catheter 3600 comprising notches 3612 on one side of the catheter 3600. As shown in FIG. 12F, the catheter may be able to bend in any direction, such as toward the notches 3612 and/or away from the notches 3612. The notches 3612 may create a flexural modulus k1 or bending modulus of elasticity for bending the catheter 3600 in a direction toward the side of the catheter 3600 comprising the notches 3612, which is lower than a flexural modulus k2 for bending the catheter 3600 in a direction substantially away from or opposite the side of the catheter 3600 comprising the notches 3612. In some embodiments, the notches 3612 may comprise a filler 3610 that increases the flexural modulus. In some embodiments, the catheter 3600 may comprise notches 3612 on various sides of the catheter 3600 that create the same or different flexural moduli. The groups of notches 3612 may be axially offset or axially aligned. As the catheter 3600 is tracked through tortuous vasculature, regions of the catheter 3600 comprising notches 3612 may respond to compressive loads (e.g., from the resistance to further distal translation of the catheter 3600) by preferentially buckling or compressing relative to an un-notched side of the catheter sidewall 3602. Fabricating catheters 3600 with radial asymmetry in mechanical properties may improve the navigability of the catheter 3600 through portions of vasculature.

Figure 12G:
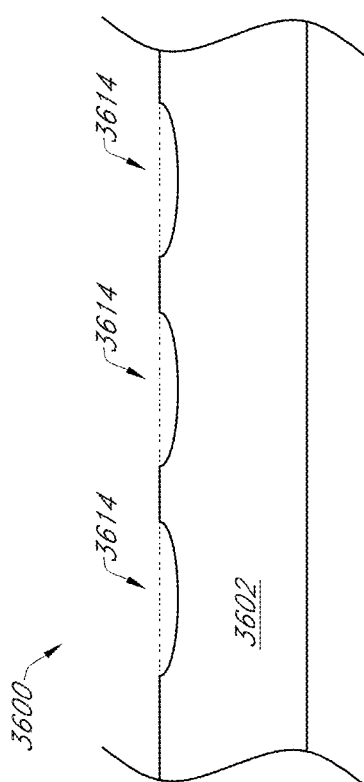
FIG. 12G schematically illustrates a cross-section of a portion of the sidewall of a catheter comprising a textured surface formed from dimples in the surface.

In some embodiments, the catheter 3600 may comprise a textured outer surface. The textured outer surface may be configured to reduce friction between the catheter and the blood vessel wall. The textured outer surface may result in improved pushability and/or trackability of the catheter. In some embodiments, the textured outer surface may comprise dimples 3614 disposed on the outer surface of the catheter 3600. FIG. 12G schematically depicts a cross-section of a portion of the sidewall 3602 of the catheter 3600 comprising a plurality of dimples 3614. A dimple 3614 may comprise an indentation or depression relative to the outer diameter of the catheter 3600, forming a localized portion of the catheter 3600 having a reduced diameter. Dimples 3614 may comprise a circular, ellipsoidal, oblong, rectangular, square, polygonal, triangular, and/or irregular shaped profile on the outer surface of the catheter. Dimples 3614 may comprise diameters (or largest dimension across the opening) of approximately 1-5 μm, 5-10 μm, 10-15 μm, 15-20 μm, 20-50 μm, 50-100 μm, less than 1 μm, or more than 100 μm. Dimples 3614 may comprise a radial depth into the sidewall of approximately 1-5 μm, 5-10 μm, 10-15 μm, 15-20 μm, 20-50 μm, 50-100 μm, less than 1 μm, or more than 100 μm. Dimples 3614 may comprise a radial depth into the sidewall of approximately 0.1-1%, 1-5%, 5-10%, 10-15%, 15-20%, 20-25%, less than 0.1%, or more than 25% of the thickness of the catheter sidewall 3602. The dimples 3614 may form a smooth continuous surface with the outer diameter of the catheter 3600. The dimples 3614 may be configured as a concavity having a generally rounded surface.

Figure 12I:
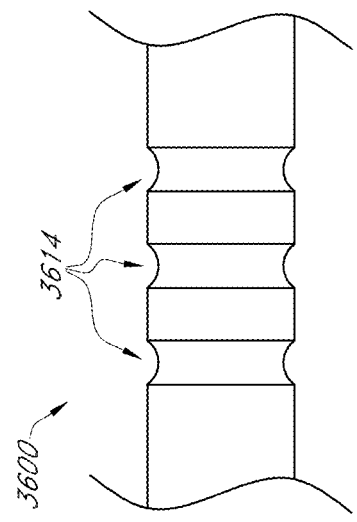
FIG. 12I schematically illustrates a side view of a portion of a catheter comprising axially-spaced ring-shaped dimples.
Figure 12H:
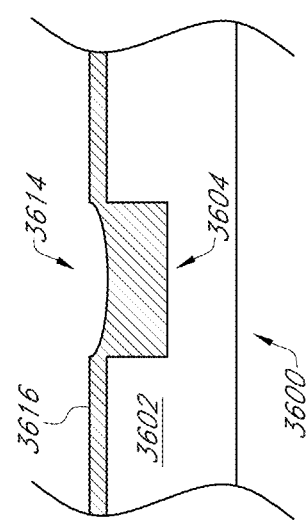
FIG. 12H schematically illustrates an example of a dimple formed by melting a jacket material into a hole formed in the sidewall.

In some embodiments, a dimple 3614 may be formed from a hole 3604 (e.g., a through hole or a blind hole). The catheter 3600 may be formed with a plurality of holes 3604 as described elsewhere herein. The catheter 3600 may then be coated or covered with a thin outer layer (e.g., a jacket layer). The jacket may be heated. Heating may adhere the outer jacket to the main body of the catheter sidewall 3602. The jacket may be melted into the holes 3604 such that the outer diameter of the jacket recedes over the holes relative to the un-perforated portion of the catheter. FIG. 12H schematically depicts an example of a dimple 3614 formed by melting a jacket material 3616 over a hole 3604. In some implementations, holes 3604 may be selectively filled to form a combination of dimples 3614 and holes 3604 from the holes 3604. The dimples 3614 may insubstantially or negligibly change the local bending or tensile stiffness of the catheter 3600. In embodiments comprising dimples 3614 and holes 3604, the dimples 3614 may generally comprise larger depths and/or larger cross-sectional areas than the holes 3604.

In some embodiments, dimples 3614 may be formed by selectively applying heating to portions of the catheter 3600 to induce localized radial shrinkage of the catheter sidewall. In some embodiments, the dimple 3614 may comprise a ring shape that extends around the entire circumference or a portion of the circumference of the catheter 3600, as schematically depicted in FIG. 12I.

Figure 12J:
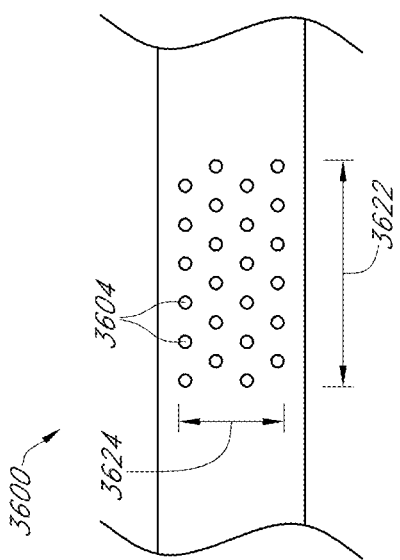
FIG. 12J schematically depicts an example of a localized region of a catheter which comprises holes.
Figure 12K:
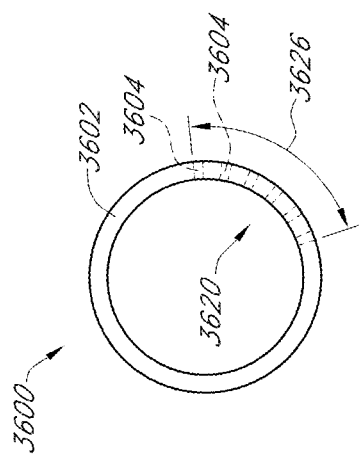
FIG. 12K schematically depicts an axial cross-section of a catheter comprising a localized region of holes over a radial sector comprising a portion of the catheter's circumference.

The plurality of holes 3604 or other sidewall features (e.g., notches 3612, dimples 3614) described herein may be disposed within one or more localized regions 3620 of the catheter sidewall 3602. FIG. 12J schematically depicts a localized region 3620 of holes 3604. The number and density of holes 3604 or other sidewall features within the localized region 3620 may modulate one or more physical properties of the catheter 3600 such as tensile or bending stiffness. As shown in FIG. 12J, the features may be disposed within a localized region 3620 having an axial length 3622 and transverse width 3624. In some embodiments, the length 3622 may be between approximately 1-5 cm, 5-10 cm, 10-15 cm, 15-20 cm, 20-25 cm, 25-30 cm, 30-50 cm, less than 1 cm, or more than 50 cm. The features may be uniformly/regularly spaced from each other, as illustrated in FIG. 12J, such as in a grid or alternating row pattern, or they may be non-uniformly/irregularly spaced. The features may be spaced approximately 1-5 µm, 5-10 µm, 10-20 µm, 20-50 µm, 50-100 µm, 100-500 µm, 500-1000 µm, less than 1 µm, or more than 1000 µm apart from each other (e.g., from center-to-center or from edge-to-edge). The cumulative cross-sectional area of the holes 3604 or other features may comprise between 5-10%, 10-20%, 20-50%, 50-80%, 80-90%, less than 5%, or more than 90% of the surface area of the localized region 3620 (of the inner or outer diameter of the catheter 3600). Within each localized region 3620, the catheter 3600 may comprise at least 50, 100, 200, 300, 500, 1000, 2000, 5000, or 10,000 holes 3604 or other features. In some embodiments, the localized region 3620 may comprise less than 50 holes 3604 or other features. The catheter 3600 may comprise 1, 2, 3, 4, 5, 6, 7, 8, 9, 10, or more than 10 localized regions of holes 3604 or other features. FIG. 12K schematically depicts an axial cross-section of the catheter 3600 comprising a localized region 3602 of holes 3604. As shown in FIG. 12K, the features may be disposed across a circumferential width or radial sector of the catheter sidewall 3602 measured by the angle 3626. The features may be disposed within a sector comprising an angle 3626 of approximately less than 5 degrees, 5-30 degrees, 30-45 degrees, 45-60 degrees, 60-90 degrees, 90-120 degrees, 120-135 degrees, 135-180 degrees, 180-270 degrees, or 270-360 degrees. In some embodiments, the localized region 3620 of features may comprise a substantially rectangular projection or profile on the outer surface of the catheter 3600, as depicted in FIG. 12J. In some embodiments, the localized region 3620 of features may comprise a non-rectangular projection. For instance, the width 26247 may vary across the length 2622 of the region, such as forming a diamond or triangular projection. In some embodiments, the localized region 3620 may comprise a substantially constant width 3624, but the circumferential positioning of the region 3620 may vary along the length 3622 of the region 3620. For instance, the localized region 3620 may spiral around the circumference over the length 3622 of the region.

The one or more localized regions 3620 of holes 3620 or other sidewall features may be disposed at the proximal end, the distal end, or along an intermediate portion of the catheter 3600. In some embodiments, the dimensions or properties of the holes 3604 or other sidewall features may be varied within a localized region 3620 of features according to the relative positioning of the feature within the localized region 3620 and/or the positioning of the localized region 3620 with respect to the overall length of the catheter 3600. For example, within a region of holes 3604 designed to decrease the localized stiffness of the catheter 3600 (e.g., void/unfilled holes), the holes 3604 may be relatively smaller near the proximal and distal ends of the localized region than near a centralized portion of the localized region to create a smoother gradient in flexibility over the localized region 3620. Similarly, in embodiments where the localized region is confined to a radial sector comprising a partial portion of the catheter 3600 circumference, the holes 3604 may be relatively smaller along the circumferential edges than along a central portion. Conversely, in embodiments in which the holes 3604 are designed to increase the stiffness (e.g., holes filled with a relatively stiff filler 3610), the holes 3604 may be relatively smaller in a central portion of the localized region 3602. In some embodiments, the additive composition of a filler 3610 may be similarly transitioned over the localized region 3620 to create a smoother (e.g., more gradual) transition in physical properties. The transitions may be continuous or somewhat stepped or discrete.

In some embodiments, the catheter sidewall 3602 may comprise stepped durometers, such as from discrete segments of a tubular outer jacket, as described elsewhere herein, comprising different durometers. For instance, a number of segments may be aligned such that the durometer of the sidewall 3602 decreases along a proximal-to-distal direction. In some embodiments, localized regions 3620 of holes 3604 or other sidewall features may be positioned near or over transition regions between adjacent sidewall sections of different durometer. The localized regions of holes may advantageously smooth the transition in stiffness over the two adjacent segments of sidewall. Smoother transitions in mechanical properties may reduce the stress exerted at the localized regions. Smooth transitions may make the catheter 3600 generally safer for use and/or may make the catheter 3600 easier to navigate and place in the vasculature. For example, holes 3604 that decrease the stiffness of the catheter 3600 may be disposed near the distal end of the stiffer (e.g., proximal) segment and/or holes that increase the stiffness of the catheter may be disposed near the proximal end of the adjacent less stiff (e.g., distal) segment. The stiffness may be modulated by the dimensions and/or the filler 3610 material of the hole 3604, as described elsewhere herein.

The catheter 3600 may comprise one or more structural reinforcements disposed within the sidewall, such as a braid and/or coil, as described elsewhere herein. The one or more reinforcement members may be disposed along the entire length of the catheter 3600 or along only axial portions of the catheter 3600. The catheter 3600 may be relatively stiffer where the reinforcement member is present and relatively more flexible where the reinforcement member is absent. In some embodiments, the reinforcement member may be disposed only within certain radial sections comprising only a portion of the catheter's circumference, at least along a partial length of the catheter. Similar to the notches 3612 described elsewhere herein, selective circumferential positioning of the reinforcement member may be used to influence bending along those lengths of the catheter. The catheter may be prone to bend toward a side of the sidewall 3602 in which the reinforcement member is absent. In some embodiments, holes 3604 or other sidewall features may be disposed in portions of the sidewall 3602 where the reinforcement member is absent. In some embodiments, holes 3604 or other sidewall features may be disposed in portions of the sidewall 3602 comprising the reinforcement member. Holes 3604 may be formed through the reinforcement member or through spaces within the reinforcement member (e.g., between windings of the coil). In some embodiments, holes 3604 may be formed in one or more layers that surround or embed the reinforcement member. In some implementations, the holes 3604 are formed in one or more of the various layers which are then assembled with the reinforcement member. Holes 3604 may be present in layer inside the reinforcement layer, outside the reinforcement layer, or both. In some implementations, holes 3604 or other features may be formed after assembling the sidewall 3602 of the catheter 3600, but may extend no further than the reinforcement layer (e.g., blind holes may extend from an outer diameter of the sidewall 3602 up to the reinforcement layer). In some embodiments, localized regions 3620 of holes 3604 or other features may be used to smooth the transition in stiffness between sections of the catheter sidewall 3602 comprising different structural reinforcement members (e.g., between a proximal braid and a distal coil) and/or sections comprising different structural properties as a result of the reinforcement member (e.g., where the pitch of the coil increases such that the catheter becomes more flexible). Similarly, one or more layers (e.g., an outer jacket) may extend only along a portion of the length of the catheter 3600. Holes 3604 or other sidewall features may be positioned through portions comprising only some of the layers and/or portions comprising all of the layers of the sidewall 3602. Holes 3604 or other features may extend through all of the layers or only some of the layers of the sidewall 3602 at any given location.

In some embodiments, the catheter 3600 may be an aggregate catheter comprising two or more catheters (e.g., 2, 3, 4, or 5 catheters) or catheter sections (e.g., an extendable catheter as described elsewhere herein) that are axially translatable relative to one another. Some mechanical properties, such as the bending stiffness and tensile stiffness, at any point along the length of the catheter 3600 may be a composite of the properties of the constituent catheters overlapping each other (e.g., coaxially) at that length. The constituent catheters may each have variable mechanical properties along their lengths or constant mechanical properties along their lengths. The mechanical properties of the constituent properties may be the same or different. A user may be able to modulate the mechanical properties of the aggregate catheter 3600 by axially aligning two or more constituent catheters to axially overlap according to produce variable mechanical properties. In some implementations, the holes 3604 or other features disclosed herein may be used to modify the mechanical properties of localized regions. In some embodiments, the holes 3604 or other features may modify the overall mechanical properties of the catheter 3600. The localized region 3620 may be large enough to substantially modify the bulk properties of the catheter 3600 or the holes 3604 or other features may be applied to the entire length of the catheter 3600. The various features described herein may be combined within a localized region 3620 of the catheter 3600 and/or a number of localized regions 3620 having different features and/or properties may be combined to modulate the overall effect on the catheter 3600.

In some embodiments, a plurality of flow holes 3634 configured to inject or introduce fluid into the internal lumen of the catheter 3600 may be disposed in the sidewall 3602, such as at the distal end of the catheter 3600. FIG. 13A depicts an example of a distal end of a catheter 3600 comprising a plurality of flow holes 3634. The fluid flow (e.g., gas or liquid) injected or introduced into the lumen may exert additional forces (e.g., shear forces) on a clot positioned within, or at least partially within, the catheter 3600, such as a clot that is stuck within aspiration lumen (a clog). The flow holes 3634 may comprise any of the shapes, dimensions, and/or features of the holes 3604 disclosed elsewhere herein. The size of the flow holes 3634 and the intermolecular forces (e.g., steric hindrance, hydrophobic interactions, surface tension, etc.) between the fluid and the sidewall 3602 of the catheter 3600 may be configured to allow fluid flow through the flow holes 3634. In some implementations, fluid flow may depend on the level of negative pressure applied through the internal lumen of the catheter 3600. For instance, liquid fluid may only flow through the flow holes 3604 upon an operative suction pressure of the aspiration catheter 3600. The size and/or the intermolecular forces may be configured to prevent or inhibit the passage of blood components (e.g., large molecules) and/or cells (e.g., blood cells) from passing through the flow holes 3634, even under negative pressure applied through the internal lumen of the catheter 3600. The number and size of the flow holes 3634 may be configured to moderate the amount of suction force applied through the plurality of flow holes 3634 such that an excessive amount of suction force is not diverted from the distal opening of the catheter 3600 which would interfere with the capture and aspiration of blood clots. In some embodiments, fluid may be injected under positive pressure through the flow holes 3634, as described elsewhere herein, which may prevent or mitigate the loss of suction at the distal opening of the catheter 3600.

The spacing and arrangement of the flow holes 3634 may be the same or similar to other holes 3604 described elsewhere herein. In some embodiments, the flow holes 3634 may measurably alter (e.g., decrease) the local stiffness of the catheter 3600 as described elsewhere herein. In some embodiments, the flow holes 3634 may be spaced and/or sized such that they do not significantly alter the physical properties of the catheter 3600 or such that the difference in physical properties is negligible. In some implementations, the decrease in stiffness resulting from the flow holes 3634 may be counterbalanced by measures which increase the local stiffness, such as holes 3604 configured to increase stiffness (e.g., holes 3604 filled with a stiffer material than the sidewall 3602).

The plurality of flow holes 3634 may be through-holes or blind holes open to the internal aspiration lumen. FIG. 13B schematically depicts a cross-section of a distal end of a catheter 3600 comprising through flow holes 3634. Through flow holes 3634 may allow suction of extraluminal fluid into the internal aspiration lumen of the catheter 3600. FIG. 13C schematically depicts a cross-section of blind flow holes 3634. Blind flow holes 3634 may be in fluid communication with one or more internal lumens 3640 disposed within the sidewall 3602 which extend proximally outside of the body. The one or more internal lumens 3640 may be in fluid communication at their proximal ends with the ambient environment or a gas (e.g., air, oxygen, nitrogen, etc.) or liquid (e.g., saline) fluid source, which, optionally, may be pressurized (e.g., via a syringe or pump). In some embodiments, applied pressure may be at least about 25, 50, 75, 100, 125, 150, 275, 200, 250, 300, 400, 500, or more than 500 mmHg. The fluid velocity may depend, at least in part, on the size of the flow hole 3634. In some implementations, pressurized fluid may be provided through the flow holes 3634 intermittently and/or on-demand (e.g., by actuation of a control at the proximal end). In some implementations, pressurized fluid may be provided continuously or at least contemporaneously with aspiration. In some implementations, pressurized fluid may be pulsed, for example at a regular frequency, at least during a longer period in which it is applied. For example, the fluid flow may be pulsed at frequencies greater than or equal to 0.1 Hz, 0.25 Hz, 0.5 Hz, 0.75 Hz, 1 Hz, 2 Hz, 3 Hz, 4 Hz, 5 Hz, 10 Hz, or more than 10 Hz. In some embodiments, the duration of a pulse of fluid flow may be at least about 0.1, 0.2, 0.3, 0.4, 0.5, 0.6, 0.7, 0.8, 0.9, 1, 2, 3, 4, 5, 10, or more than 10 seconds. In some embodiments, through flow holes 3634 may also be in fluid communication with one or more internal lumens 3640 such that fluid may be introduced from the extraluminal environment and from the proximal fluid sources in communication with the internal lumens 3640. In some embodiments, the catheter 3600 comprises combinations of through flow holes and blind flow holes 3634.

FIGS. 13Di-13Dv schematically illustrate various examples of cross-sections bisecting the longitudinal axis of the catheter 3600 comprising a plurality of flow holes 3634. FIG. 13Di depicts a plurality of fluid flow through holes 3634 arranged around the circumference of the catheter 3600. The flow holes 3634 are aligned along a radial direction of the catheter 3600 within the represented plane. In some embodiments, the flow holes 3634 may be arranged in an off-radial direction as shown in FIG. 13Dii. The flow holes 3634, or at least a portion (e.g., the portion opening into the catheter lumen) may form an angle 3636 in a circumferential direction with respect to the normal of the inner diameter of the sidewall 3602 (the radial direction). The angle 3636 may be at least about 10, 20, 30, 40, 45, 50, 60, 65, 70, or 75 degrees. The orientation of the flow hole 3634 may affect the direction of the fluid flow into the lumen of the catheter 3600, as schematically illustrated in FIGS. 13Di and 13Dii. The direction of the fluid flow may be indicative of the direction of the force vector imparted by the fluid flow. For instance, the forces resulting from the fluid flow in FIG. 13Di may be generally compressive relative to a clot positioned (e.g., stuck) within the catheter lumen. The forces resulting from the fluid flow in FIG. 13Dii may be generally shear relative to a clot positioned within the catheter lumen. The net effect of the fluid flow in FIG. 13Dii may create a fluid vortex effect within the catheter lumen. The fluid flow may be laminar or turbulent. The orientation of the fluid flow channels may be selected to optimize the forces imparted on a clot for dislodging a clot within the lumen. In some implementations, the fluid forces may promote fragmentation or breaking apart the clot into smaller pieces. In some implementations, the fluid forces may promote reorientation of the clot within the lumen. In some implementations, the fluid forces may alter, permanently or transiently, the shape and/or size of the clot. Providing pressurized fluid flow may increase the magnitude of the force vector. Use of pressurize fluid may allow modulation of the direction of the net force vector from the fluid flow under aspiration. FIG. 13Diii depicts a plurality of blind flow holes 3634 in fluid connection with a single concentric or coaxial internal lumen 3640. The internal lumen 3640 may extend along the length of the catheter 3600 between an inner diameter and outer diameter of the sidewall 3602. The depth of the internal lumen 3640 may remain constant along the length of the catheter 3600 or it may vary. FIG. 13Div depicts a plurality of blind flow holes 3634 in fluid communication with a plurality of internal lumens 3640. Each flow hole 3634 may be in communication with its own internal lumen 3640. The plurality of internal lumens 3640 may be positioned around the circumference of the catheter 3600 and may extend generally linearly along the length of the catheter 3600. Use of non-concentric internal lumens 3640 may allow the lumens to be positioned closer to the outer diameter of the sidewall 3602 while preserving structural integrity and may allow minimization of the sidewall 3602 thickness. In some embodiments, the internal lumens 3640 may extend along the axial length of the catheter 3600 in a non-linear fashion. For instance, the lumens 3650 may comprise a circumferential component forming an angle relative to the radial direction similar to angle 3636. The lumens 3640 may form a spiral or helical pattern along the length of the catheter 3600. The orientation of the lumens, particularly near the flow holes 3634, may influence the direction of fluid flow from the flow holes 3634, depending on the fluid velocity (the orientation may have greater influence at higher velocities). Each internal lumen 3640 may be in fluid communication with one or more flow holes 3634 (e.g., 1, 2, 3, 4, etc.). FIG. 13Dv depicts a catheter 3600 comprising a plurality of internal lumens 3640 intersecting the inner diameter of the sidewall 3602 to form the blind flow holes 3634. In some embodiments, the internal lumens 3640 may extend along at least a portion of the length of the catheter 3600 open to the internal lumen. The internal lumens 3640 may form a textured surface. Flow through the internal lumens around a clot may help dislodge the clot. The flow holes 3634 in any of the examples disclosed herein may be spaced uniformly or non-uniformly around the circumference of the catheter 3600. Any of the configurations of flow holes 3634 and internal lumens 3640 may be combined.

In some embodiments, a fluid supply lumen 3642 may be formed by a sleeve 3644. FIG. 13E schematically depicts a cross-section bisecting the longitudinal axis of the catheter 3600 where a fluid supply lumen 3642 is formed by a sleeve 3644 over the catheter 3600. The sleeve 3644 may be relatively thin. For example, the sleeve 3644 may be thinner than the sidewall 3602. In some embodiments, the sleeve 3644 may be no greater than about 0.001, about 0.002, about 0.003, about 0.004, about 0.005, or about 0.01 inches thick. The sleeve 3644 may be relatively compliant or elastic. In some embodiments, the sleeve 3644 may comprise a biocompatible elastic polymer, such as polyurethane, a fluoropolymer, polyethylene, and/or any of the materials described herein for use in the sidewall 3602 of the catheter 3600. The sleeve 3644 may be positioned concentrically outside of the catheter 3600 to form the fluid supply lumen 3642 between the sidewall 3602 of the catheter 3600 and the sleeve 3644. The fluid supply lumen 3642 may be substantially annular. The sleeve 3644 may be coupled at its proximal end to a fluid supply source to provide the fluid flow (e.g., air, saline, etc.). The sleeve 3644 could be introduced simultaneously with the catheter 3600 or could be introduced over the catheter 3600 after the catheter 3600 has been at least partially navigated to the target location within the vasculature. The catheter 3600 may effectively serve as a guidewire for introducing the sleeve 3644. FIG. 13F schematically depicts a side cross-section of the distal end of the catheter 3600 partially covered by the sleeve 3644. The sleeve 3644 may comprise an unbiased inner diameter that substantially matches or is only slightly larger than the outer diameter of the sidewall 3602 of the catheter 3600, as shown in FIG. 13F. Providing a slight diameter gap may reduce the friction during the introduction of the sleeve 3644 over the catheter 3600. Minimizing the space between the outer diameter of the sidewall 3602 and the unbiased inner diameter of the sleeve 3644 may advantageously minimize the outer diameter of the sleeve 3644 during introduction into the vasculature and/or allow maximization of the diameter of the catheter 3600. Once the catheter 3600 and sleeve 3644 are in position, the fluid supply lumen 3652 may be supplied with pressurized fluid, for example, during aspiration. The delivery of pressurized fluid through the sleeve 3644 may expand or somewhat inflate the sleeve 3644, increasing the sleeve diameter, as illustrated in FIG. 13G. The sleeve 3644 may be positioned such that a distal end of the sleeve 3644 is positioned distally beyond most-distal flow hole 3634. In some embodiments, pressurized fluid may escape through the distal end of the sleeve 3644 as well as through the flow holes 3634. In some embodiments, the sleeve 3644 may comprise an annular flange or other sealing feature 3646 which at least partially seals the distal end of the sleeve 3644 with the outer diameter of the sidewall 3602 of the catheter 3600 to prevent or reduce the amount of fluid flow through the distal end of the sleeve 3644. The sealing feature 3646 may comprise a reduced diameter. The sealing feature 3646 may be relatively less elastic and/or compliant than the body of the sleeve 3644. The sealing feature 3646 may comprise the same and/or different materials from the body of the sleeve 3644 disclosed elsewhere herein. The sealing feature 3646 may be configured to slide along sidewall 3602 during introduction of the sleeve 3644. In some embodiments, the sleeve 3644 may be selectively positioned over the distal end, or other portion of the length, of the catheter 3600, to selectively cover a portion of the flow holes 3634 such that fluid is supplied only to the covered flow holes 3634 as shown in FIGS. 13G and 13F. Extraluminal fluid may continue to be aspirated through the uncovered flow holes 3634 during aspiration. In some embodiments, the distal end of the sleeve 3644 may comprise a distal length that effectively seals, for example via a reduced diameter, any flow holes 3634 over which the distal length is positioned. In some embodiments, various designs of sleeves 3644 may be used to selectively seal and/or deliver fluid to various configurations of flow holes 3634. In some implementations, a sleeve 3644 may be used without supplying a fluid so as to seal flow holes 3634 from the extraluminal environment and prevent or reduce fluid flow through the flow holes 3634.

FIGS. 13Hi-13Hvi schematically illustrate various examples of side cross-sections of a distal end of the catheter 3600 comprising a plurality of flow holes 3634. FIG. 13Hi depicts a plurality of flow holes 3634 aligned along the radial direction within the represented plane. FIG. 13Hii depicts a plurality of flow holes 3634 aligned in an off-radial direction within the represented plane. The flow holes 3634, or at least a portion (e.g., the portion opening into the catheter lumen) may form an angle 3638 in a longitudinal direction, in either the proximal or distal direction, with respect to the normal of the inner diameter of the sidewall 3602 (the radial direction). The angle 3638 may be at least about 10, 20, 30, 40, 45, 50, 60, 65, 70, 75, or more than 75 degrees. Any of the flow holes 3634 depicted may additionally be angled in a circumferential direction by an angle 3636, as depicted in FIG. 13Dii. In some implementations, angling the flow holes 3638 in a proximal direction, as shown in FIG. 13Hii, may help promote movement of a clot in a proximal direction down the aspiration catheter 3600. As depicted in FIG. 13Hiii, the plurality of flow holes 3604 may be aligned in different directions. In some embodiments, flow holes 3604 positioned at same length along the longitudinal axis may comprise the same angle 3638. The angle 3638 of the flow holes 3604 may change (e.g., gradually increase or gradually decrease) along the longitudinal direction. The angle 3638 gradually decreases in a proximal direction in FIG. 13Hiii. The variable angling of the flow holes 3638 may be used to create complex flow patterns and/or to target flow toward various points within the catheter lumen. In some embodiments, flow holes 3634 may be oriented in opposite directions, such as shown in FIG. 13Hiv. Use of multiple internal lumens 3640, as depicted in FIG. 13Hv and FIG. 13Div, may allow independent control of fluid flow through different subsets of flow holes 3634 (e.g., different lumens 3640 may be connected to the same or different fluid sources). For example, fluid flow can be provided through the various subsets at different times, under different pressures, and/or using different fluids. FIG. 13Div depicts longitudinally space flow holes 3640 that are in fluid communication with different internal lumens 3640. The internal lumens may be radially spaced apart as illustrated in FIG. 13Hiv or otherwise positioned suitable. In some implementations, fluid flow may be provided to a distal set of flow holes 3634 followed by a more proximal set of flow holes 3640. For example, fluid flow may be cycled along the length of the catheter from a distal-to-proximal direction, which may urge the clot in a proximal direction down the aspiration catheter 3600. In some embodiments, some flow holes 3634 may share an internal lumen 3604 with non-adjacent flow holes 3634, being interspersed by flow holes 3634 connected to a different internal lumen 3604.

FIG. 13I depicts a side cross-section of the distal end of a catheter 3600 comprising various shaped flow holes 3634. The flow holes 3634 may be shaped the same or similarly to the holes 3604 described elsewhere herein and the openings of the flow holes 3604 into the catheter lumen may form a taper angle 3608 as described elsewhere herein. In some embodiments, the taper angle 3608 may be between about 0-15 degrees, between about 15-30 degrees, between about 30-45 degrees, between 45-60 about degrees, or greater than about 60 degrees. The taper angle 3608 may be positive wherein the flow hole 3634 expands toward the opening or negative wherein the flow hole 3634 decreases toward the opening. In some embodiments, the flow hole 3634 may be asymmetric forming multiple taper angles 3634. The taper angle 3608 may affect the direction of fluid flow and/or the velocity of fluid flow.

In some of the embodiments described herein, flow holes 3634 may alternatively or interchangeably be connected to a negative pressure source (e.g., a vacuum pump) to generate suction through the flow holes exerting forces in a substantially radially outward direction. In some implementations, cycling of outward suction on at least some of the flow holes 3634 (either with ambient pressure or cycling between positive and negative applied pressure) may help loosen a clot within the lumen of the catheter 3600.

In some embodiments, a plurality of flow holes may be positioned at a distal end of the catheter 3600 as described elsewhere herein. Alternatively, or additionally, flow holes 3634 may be positioned along other portions of the catheter 3600. For example, flow holes 3634 may be positioned at places where a clot may be prone to becoming stuck within the lumen, such as within a portion of the catheter 3600 configured to make a sharp bend.

Figure 15:
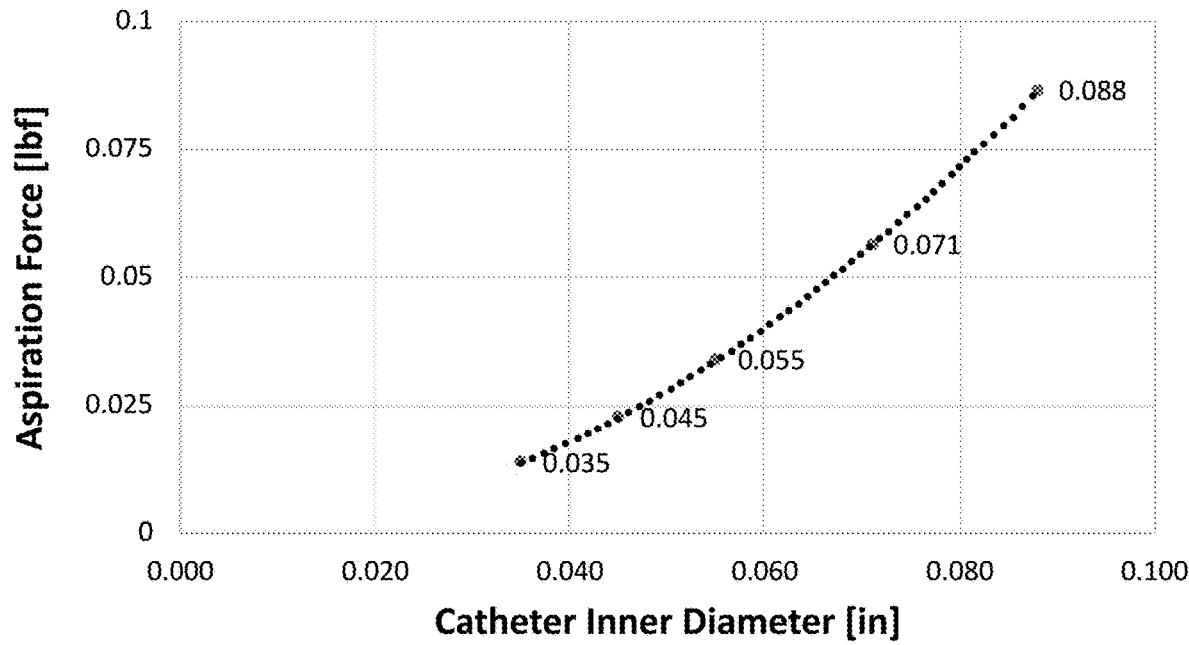
FIG. 15 depicts a graph of aspiration force for conventional catheters as a function of catheter inner diameter.
Figure 16:
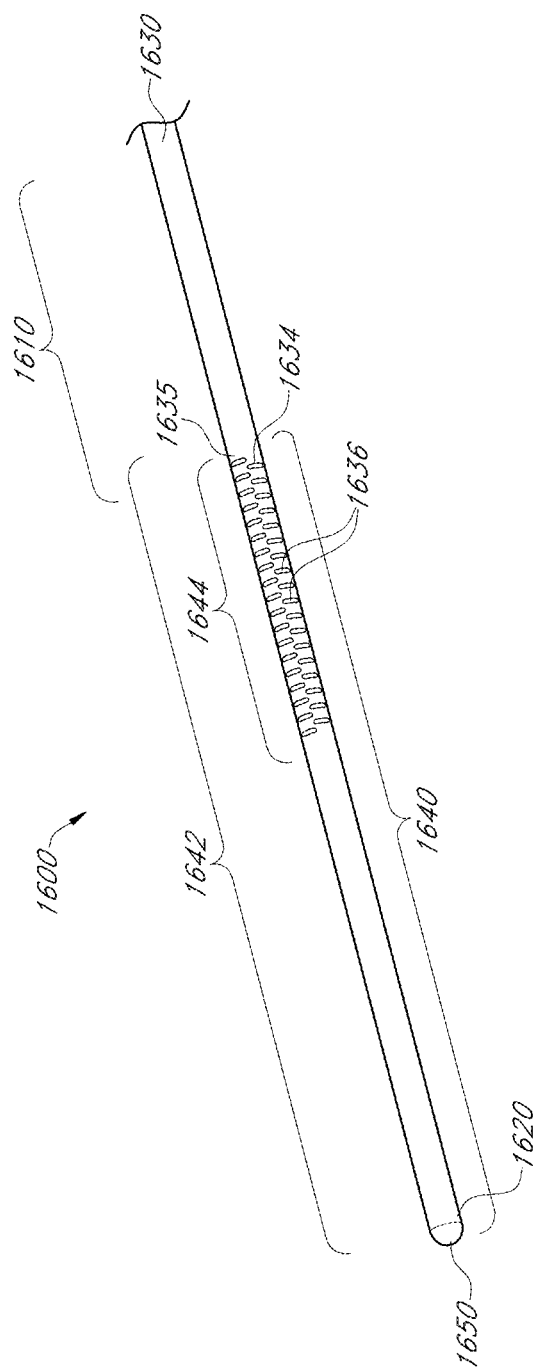
FIG. 16 schematically depicts an example of a three-dimensional aspiration device.

Any of the preceding embodiments of perforated neurovascular catheters may be used for aspiration. However, catheters typically apply vacuum across a relatively small area, dictated by the catheter's inner diameter at the distal end of the catheter. Further, the catheter's inner diameter is limited by the vessel size and the tortuosity of the anatomy. As shown in FIG. 15, aspiration force grows quadratically as catheter lumen increases. Physician bench studies have demonstrated greater success removing clots with large bore catheters than with catheters with smaller lumens. Thus, there seems to be great benefit in increasing the active area of aspiration.

As shown in FIGS. 16-19, a three-dimensional aspiration device or a device for increasing an active area of aspiration 1600 includes an elongate tubular body 1610 having a proximal end 1630, a distal end 1635, and defining a lumen therethrough; and an at least partially porous tubular body 1640. Device 1600 functions to create a three-dimensional aspiration area as opposed to a two-dimensional aspiration area (i.e., cross-sectional area of luminal opening of a catheter distal end). Device 1600 further functions to enable the vacuum to be delivered to a greater area of clot burden; to grip the clot; to act as an anchor or grappling hook to navigate up a larger bore catheter without damaging the vessel wall; and/or to desiccate (i.e., remove moisture) the clot thereby allowing it to become easier to ingest by a larger bore catheter.

The at least partially porous tubular body 1640 includes a proximal portion 1634 coupled to the distal end 1635 of elongate tubular body 1630, a distal tip 1620, and a sidewall 1642 extending between a proximal end 1634 of the at least partially porous tubular body 1640 and the distal tip 1620. The sidewall 1642 comprises an active region 1644 defining a plurality of apertures 1636 fluidly coupled to the lumen of the elongate tubular body 1610. A percentage of an area of the plurality of apertures 1636 to a total open surface area of the active region 1644 is within a range from about 15% to about 20%. The total open surface area of the active region 1644 may range from about or substantially 10% to about 50%; about 15% to about 20%; about 12% to about 23%; about 15% to about 25%; about 17% to about 19%; about 15% to about 30%; about 5% to about 50%; etc. In some embodiments, vacuum suction is applied through the lumen defined by the elongate tubular body 1610 and through the plurality of apertures 1636 to engage embolic material in an intravascular site of a patient.

The elongate tubular body 1610 may comprise or be formed of one or more of: stainless steel, Nitinol, or like materials.

An axial length of the active aspiration region 1644 may be from about or substantially 0.5 mm to about 15 mm; about 1 mm to about 10 mm; about 1 mm to about 1.3 mm; about 1 mm to about 2.5 mm; about 1 mm to about 4.2 mm; about 1 mm to about 4.5 mm; about 1 mm to about 6.5 mm; about 1.3 mm to about 6.5 mm; about 2.5 to about 6.5 mm; about 4.2 mm to about 6.5 mm; about 6.5 mm to about 10 mm; about 10 mm to about 15 mm; about 1.3 mm to about 10 mm; about 1.5 mm to about 10 mm; about 2.5 mm to about 10 mm; about 4.2 mm to about 10 mm; about 4.5 mm to about 10 mm; about 1.3 mm to about 4.2 mm; about 1.5 mm to about 4.2 mm; about 1.5 mm to about 4.5 mm; about 5 mm to about 15 mm; etc. The active aspiration region 1644 may be about 0 mm to about 50 mm; about 0 mm to about 25 mm; about 0 mm to about 10 mm; about 0.5 mm to about 15 mm; about 1 mm to about 10 mm; about 1 mm to about 1.3 mm; about 1 mm to about 2.5 mm; about 1 mm to about 4.2 mm; about 1 mm to about 4.5 mm; about 1 to about 6.5 mm; about 1.3 mm to about 6.5 mm; about 2.5 to about 6.5 mm; about 4.2 mm to about 6.5 mm; about 6.5 mm to about 10 mm; about 10 mm to about 15 mm; about 1.3 mm to about 10 mm; about 1.5 mm to about 10 mm; about 2.5 mm to about 10 mm; about 4.2 mm to about 10 mm; about 4.5 mm to about 10 mm; about 1.3 mm to about 4.2 mm; about 1.5 mm to about 4.2 mm; about 1.5 mm to about 4.5 mm from a distal end 1620 of the at least partially porous tubular body 1640. The plurality of apertures 1636 of the active aspiration region 1644 may comprise a laser cut pattern of through holes. Any of the embodiments of through holes, dimples, flow holes, notches, etc. described elsewhere herein are contemplated for the active aspiration region 1644. In one non-limiting example, the plurality of apertures 1636 is in an interrupted spiral pattern. An outer diameter of a 3D aspiration device 1600 may be about 0.014 inches to about 0.038 inches; about 0.015 inches to about 0.030 inches; about 0.020 inches to about 0.025 inches; about 0.020 inches to about 0.030 inches, etc. An inner diameter of a 3D aspiration device 1600 may be about 0.012 inches to about 0.036 inches; about 0.013 inches to about 0.028 inches; about 0.018 inches to about 0.023 inches; about 0.018 inches to about 0.028 inches, etc. These dimensions (outer and inner diameter) enable a low clot crossing profile of the three-dimensional aspiration device.

The distal end 1620 of the at least partially porous tubular body 1640 may define a distal aperture. Additionally, or alternatively, the distal end 1620 includes a valve 1650 positioned thereon, for example to allow a guidewire to pass through the lumen of the elongate tubular body 1610 and thus through a lumen of the active aspiration region 1644 and out the distal end 1620 while limiting or preventing blood from entering the distal end 1620 during navigation or aspiration. The valve 1650 may include a silicone valve, a duckbill valve, or another other valve known to one of skill in the art. Inclusion of a valve 1650 on the distal end 1620 may also make the distal end 1620 more atraumatic, to reduce or prevent vessel damage during advancement or retraction in the vessel. In some embodiments, a proximal end 1634 of the at least partially porous tubular body 1640 includes a radiopaque marker band to enable visualization of the active aspiration region 1644 relative to a clot, anatomy, or other interventional devices.

Figure 17:
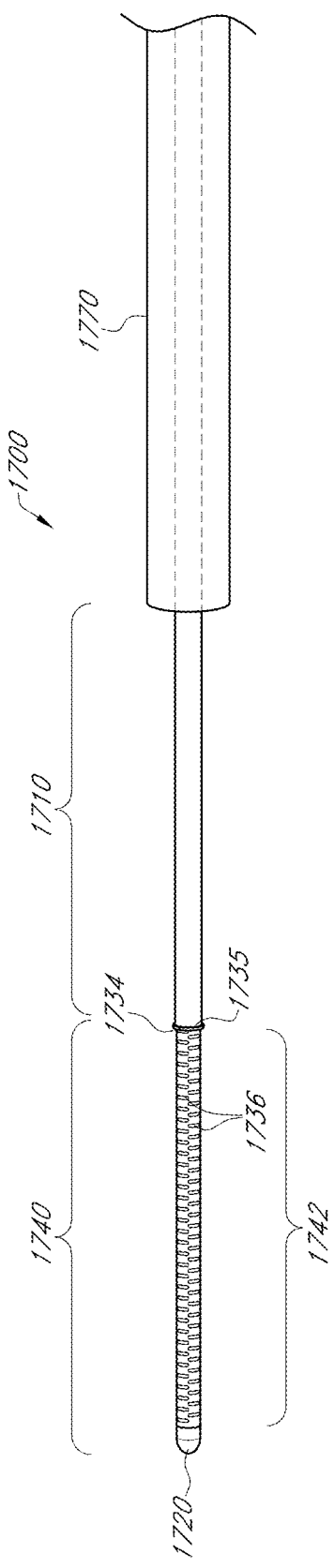
FIG. 17 schematically depicts another example of a three-dimensional aspiration device.

In some embodiments, as shown in FIG. 17, an elongate shaft 1710 extends through the lumen of the elongate tubular body 1770, such that the proximal end 1734 of the at least partially porous tubular body 1740 is coupled to a distal end 1735 of the elongate shaft 1710. The at least partially porous tubular body 1740 includes a proximal end 1734 and distal end 1720 with a sidewall 1742 extending therebetween. In this embodiment, an entirety of or substantially an entirety of the sidewall 1742 comprises the active aspiration region defining a plurality of apertures 1736. A proximal end 1734 of the at least partially porous tubular body 1740 is coupled to a distal end 1735 of elongate tubular body 1710. The elongate tubular body 1710 may be coupled to the at least partially porous tubular body 1740 via glue, adhesive, soldering, welding, brazing, mechanical linkage (e.g., keyed or complementary surfaces), solvent bonding, or any other method known to one of skill in the art. The sidewall 1742 and/or active aspiration region may include or be formed of one or more of: stainless steel, Nitinol, or like material. The three-dimensional aspiration device 1700 may be passed through a microcatheter or other catheter 1770 to reach a site of a clot or thrombus.

Figure 18:
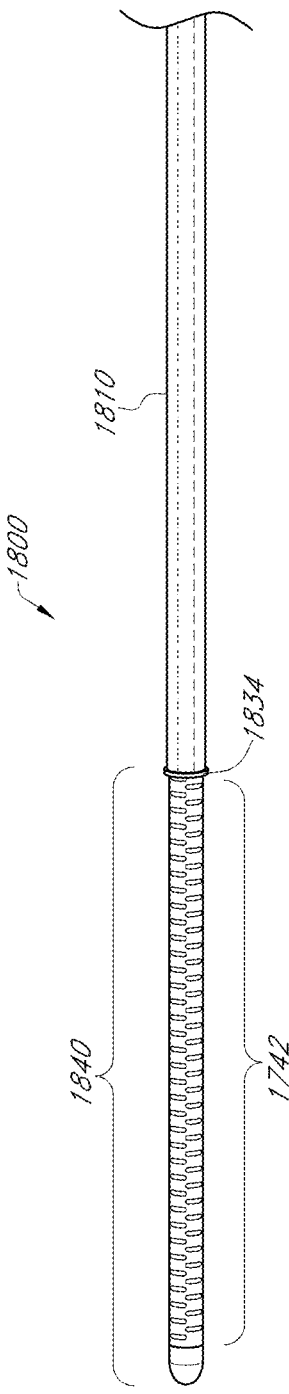
FIG. 18 schematically depicts another example of a three-dimensional aspiration device.

In some embodiments, as shown in FIG. 18, a three-dimensional aspiration device 1800 includes an elongate tubular body 1810 comprising a microcatheter that is coupled to a proximal end 1834 of an at least partially porous tubular body 1840, having sidewall 1842 including an active aspiration region, for navigation to a site of a clot or thrombus. The at least partially porous tubular body 1840 may be coupled to elongate tubular body (i.e., microcatheter) 1810 via glue, adhesive, soldering, welding, brazing, mechanical linkage (e.g., keyed or complementary surfaces), solvent bonding, or any other method known to one of skill in the art.

Figure 19A:
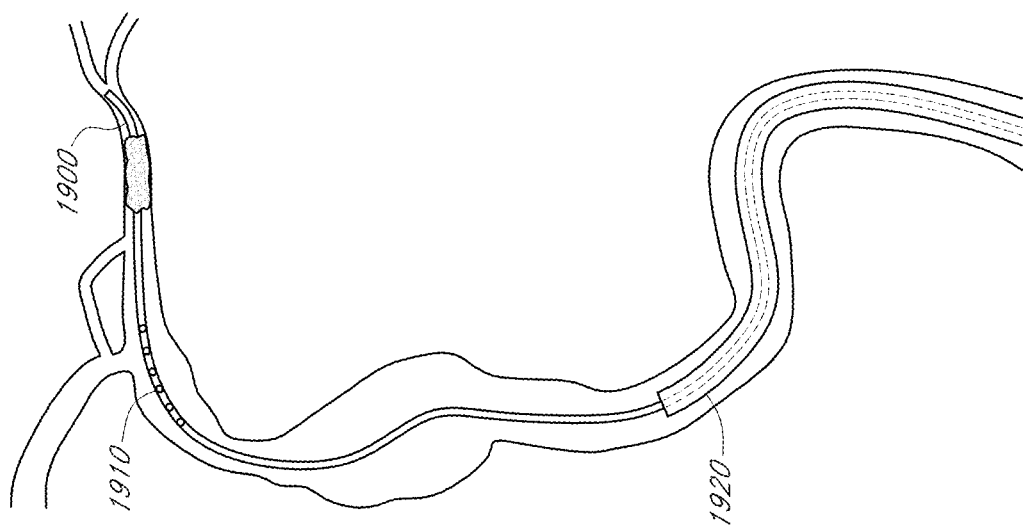
FIGS. 19A-19G schematically depict various aspects of a method of using a three-dimensional aspiration device.
Figure 19B:
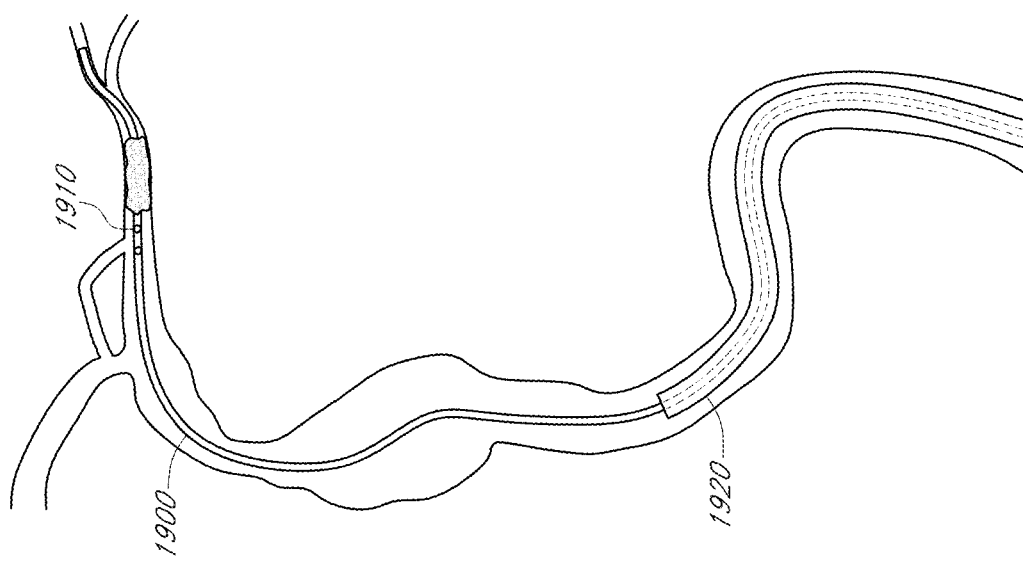
Figure 19C:
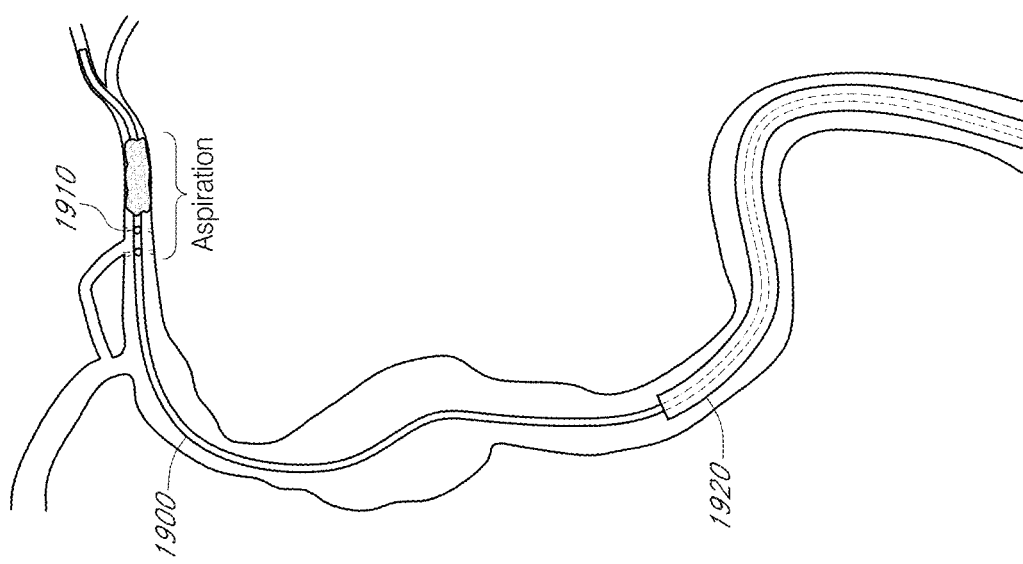
Figure 19D:
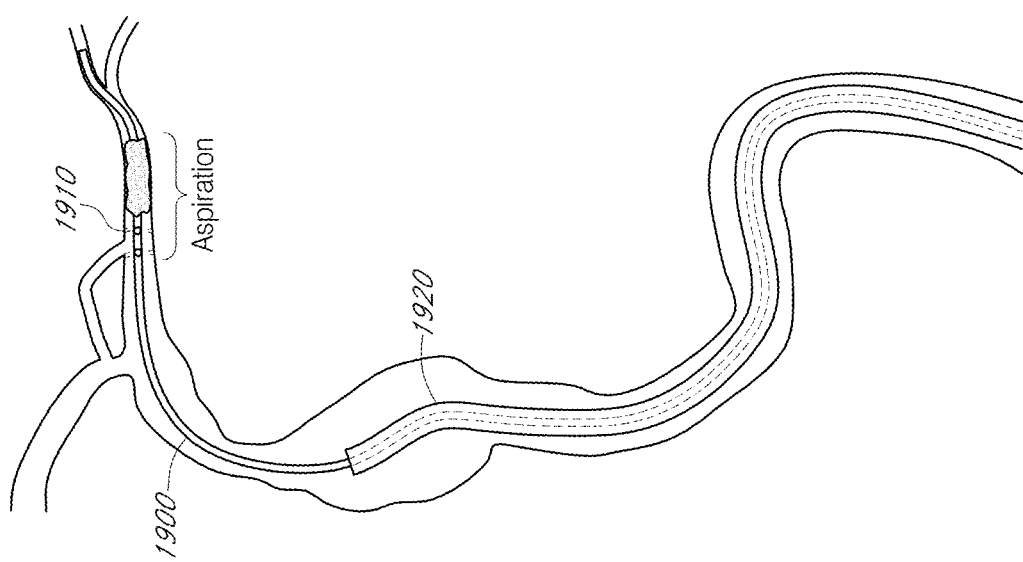
Figure 19E:
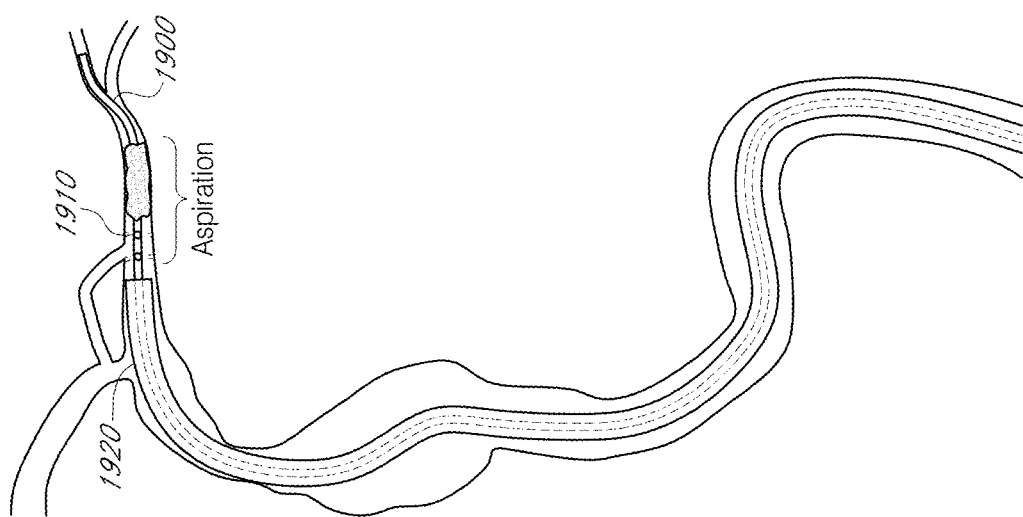
Figure 19F:
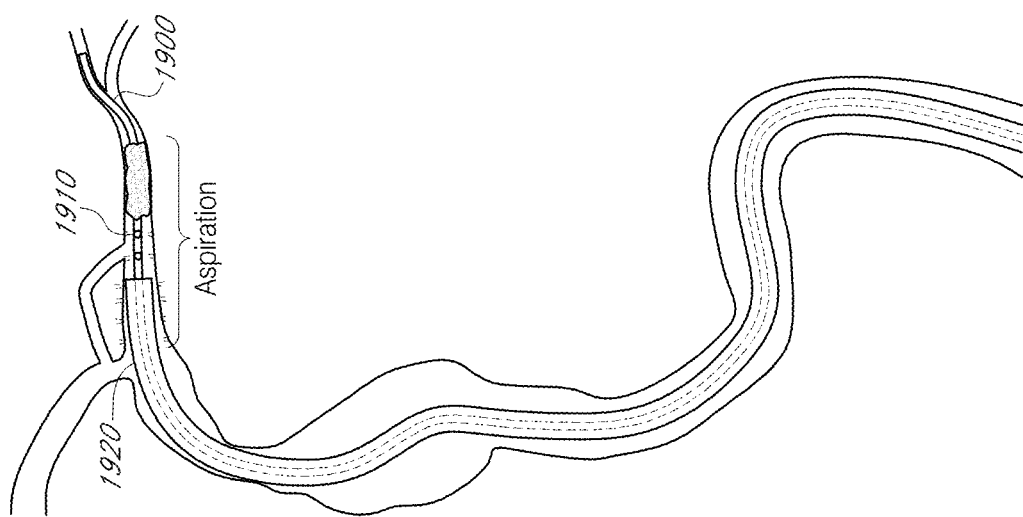
Figure 19G:
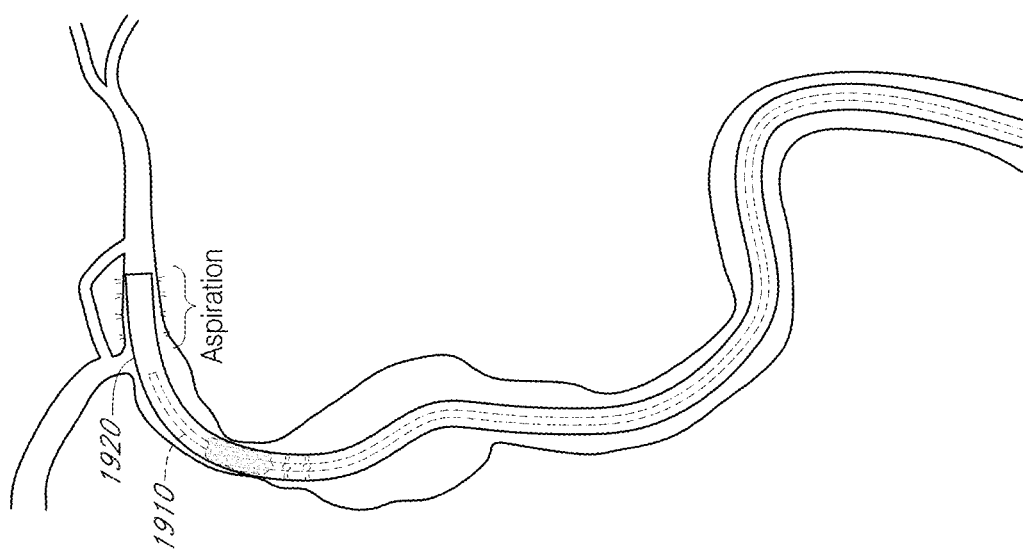

A method of using any of the three-dimensional aspiration devices described herein may include: advancing a three-dimensional aspiration device 1900 through a clot 1912 (FIG. 19A); advancing an active aspiration region 1910 of the three-dimensional aspiration device 1900 through the clot 1912 (optionally over a guidewire or similar device); advancing an active aspiration region to a proximal face of the clot (FIG. 19B); activating aspiration through the three-dimensional aspiration device 1900 to lock or secure the device in position in the clot 1912 (FIG. 19C); advancing a catheter 1920 over the three-dimensional aspiration device 1900, using the locked three-dimensional aspiration device 1900 as a rail (FIG. 19D); positioning the catheter 1920 at the proximal face of the clot 1912 (FIG. 19E); activating aspiration through the catheter 1920 (FIG. 19F); and retracting the three-dimensional aspiration device 1910 with the clot 1912 attached into the catheter 1920 (FIG. 19G).

Figure 20C:
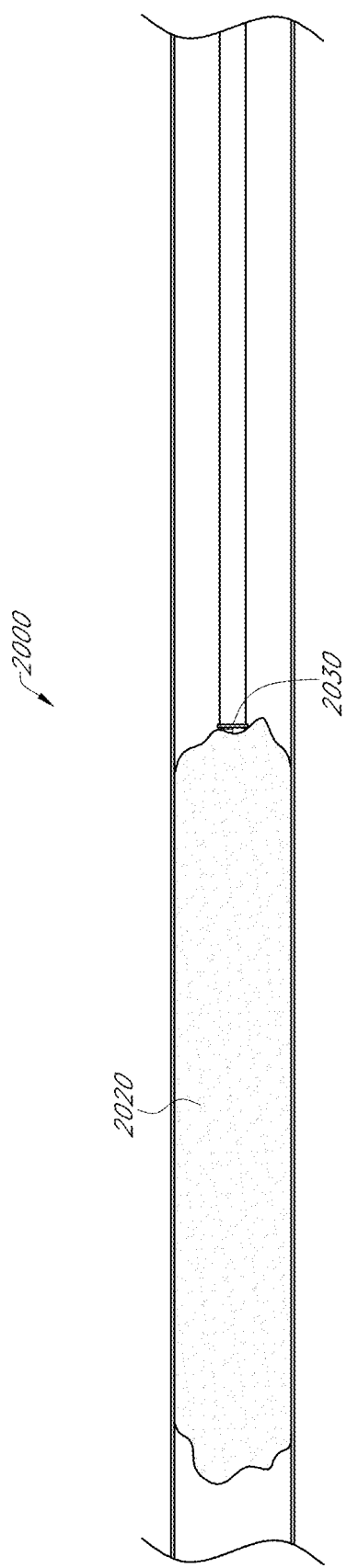
Figure 20D:
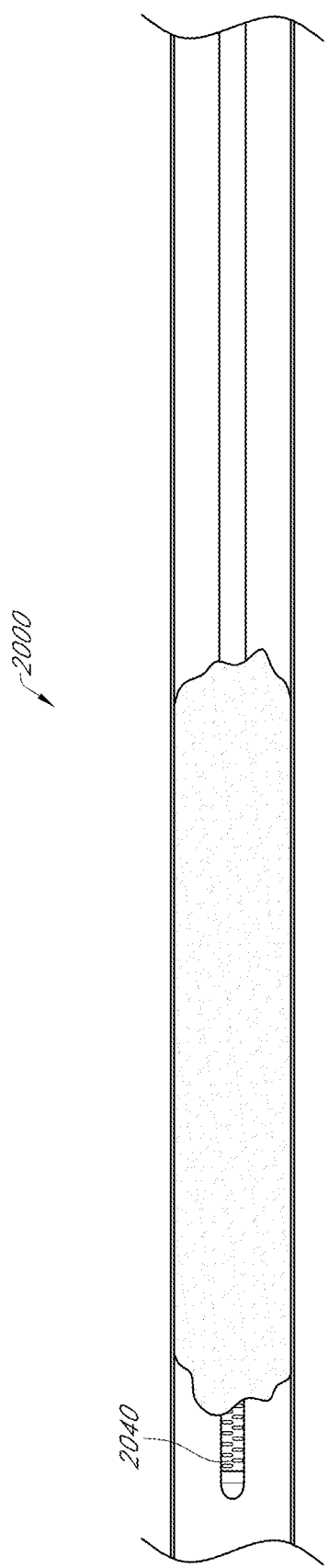
Figure 20E:
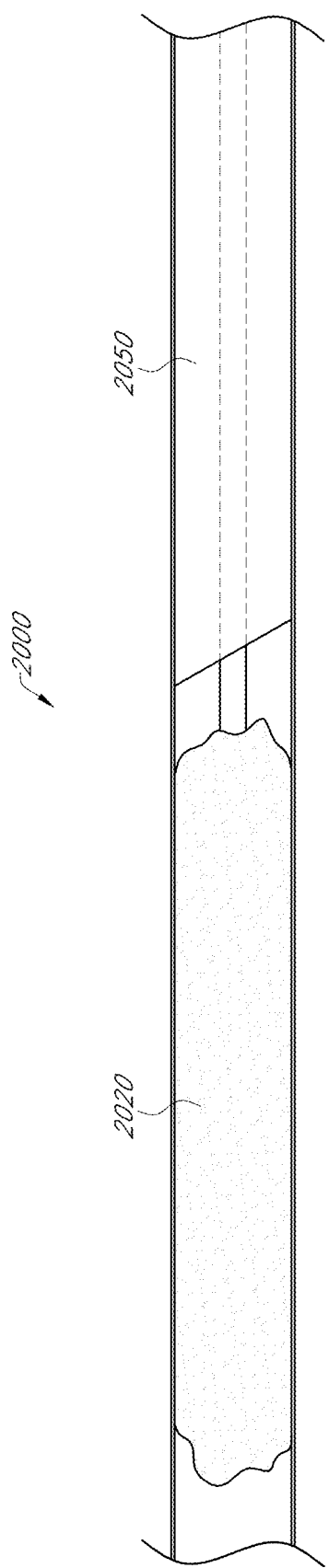
Figure 20F:
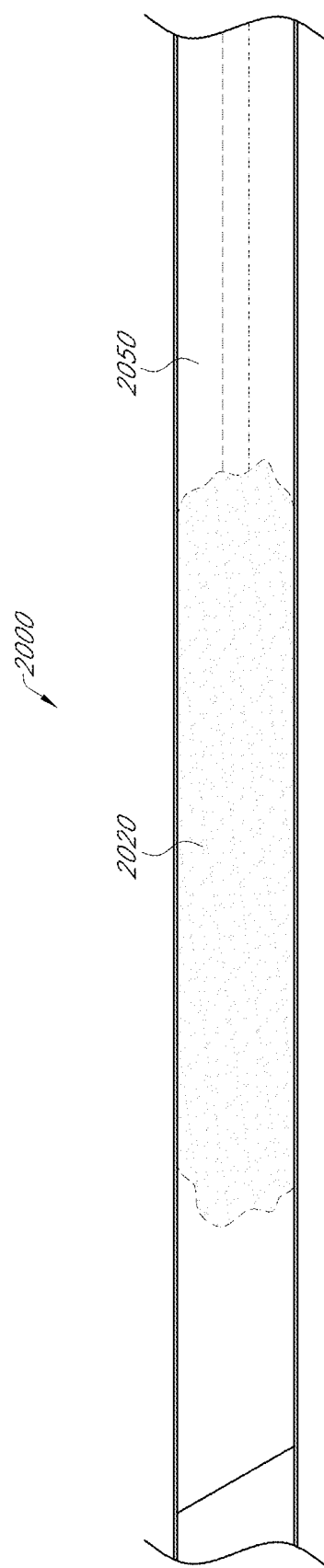
Figure 21:
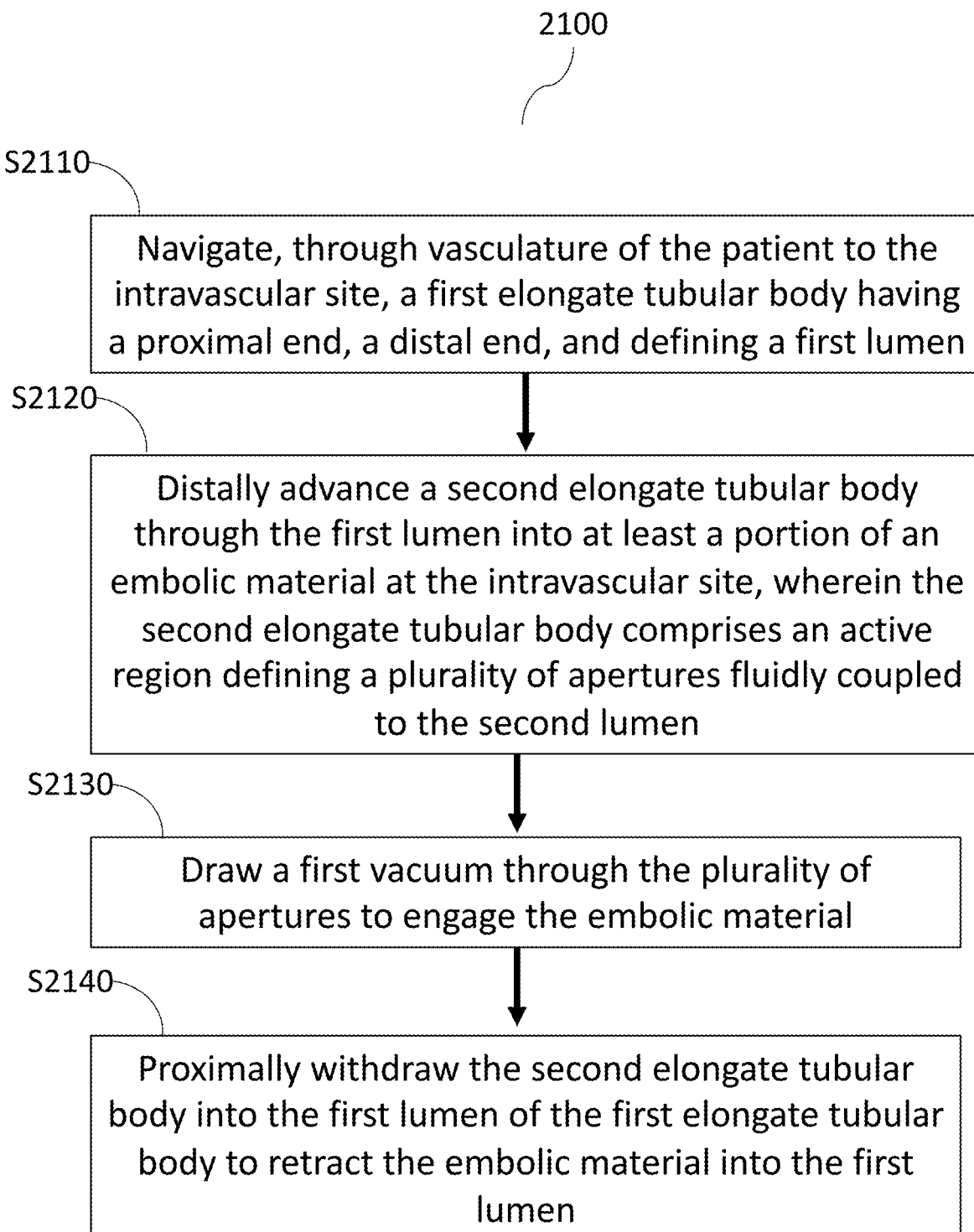
FIG. 21 depicts a flow chart of one embodiment of a method of using a three-dimensional aspiration device.

Another embodiment of a method 2000 of using any of the three-dimensional aspiration devices described herein may include: advancing a three-dimensional aspiration device 2010 to a proximal face of a clot 2020 (FIG. 20A); passing through the clot 2020 with the three-dimensional aspiration device 2000 (may be optionally advanced and passed through over a guidewire) (FIG. 20B); aligning a radiopaque marker band 2030 of the three-dimensional aspiration device 2010 with the proximal face of the clot 2020; activating aspiration when radiopaque marker band 2030 is at proximal face of clot 2020 (FIG. 20C); preventing advancement of the a distal end 2040 of the device 2010 past a distal face of the clot 2020 (FIG. 20D); advancing a catheter 2050 over the three-dimensional aspiration device 2010, using the locked three-dimensional aspiration device as a rail (FIG. 20E); and retracting the three-dimensional aspiration device 2010 with the clot 2020 attached into the catheter 2050 (FIG. 20F).

Another method 2100 of using any of the three-dimensional aspiration devices described herein may include: navigating, through vasculature of the patient to the intravascular site, a first elongate tubular body (e.g., catheter) having a proximal end, a distal end, and defining a first lumen S2110; distally advancing a second elongate tubular body through the first lumen into at least a portion of an embolic material at the intravascular site, wherein the second elongate tubular body comprises: a proximal end, a distal end, and defines a second lumen; and an active region defining a plurality of apertures fluidly coupled to the second lumen S2120; drawing a first vacuum through the plurality of apertures to engage the embolic material S2130; and proximally withdrawing the second elongate tubular body into the first lumen of the first elongate tubular body to retract the embolic material into the first lumen S2140.

Withdrawing the second elongate body into the first lumen of the first elongate tubular body may further include distally advancing the first elongate body toward the embolic material; and drawing a second vacuum through the first lumen and proximally withdrawing the second elongate body into the first lumen to retract the embolic material into the first lumen.

In some embodiments where a three-dimensional aspiration device includes a radiopaque marker, the method 2100 may include distally advancing the second elongate body into at least a portion of the embolic material to position the radiopaque marker adjacent a proximal face of the embolic material.

In some embodiments, navigating the first and second elongate bodies includes navigating an elongate shaft (e.g., guidewire) to the intravascular site; and navigating, over the elongate shaft, the first and second elongate bodies to the intravascular site.

In some embodiments where the second elongate body comprises a sleeve extending around at least a portion of a perimeter of the active region, the method may further include adjusting an axial position of the sleeve to control a number of exposed apertures of the plurality of apertures.

Figure 22:
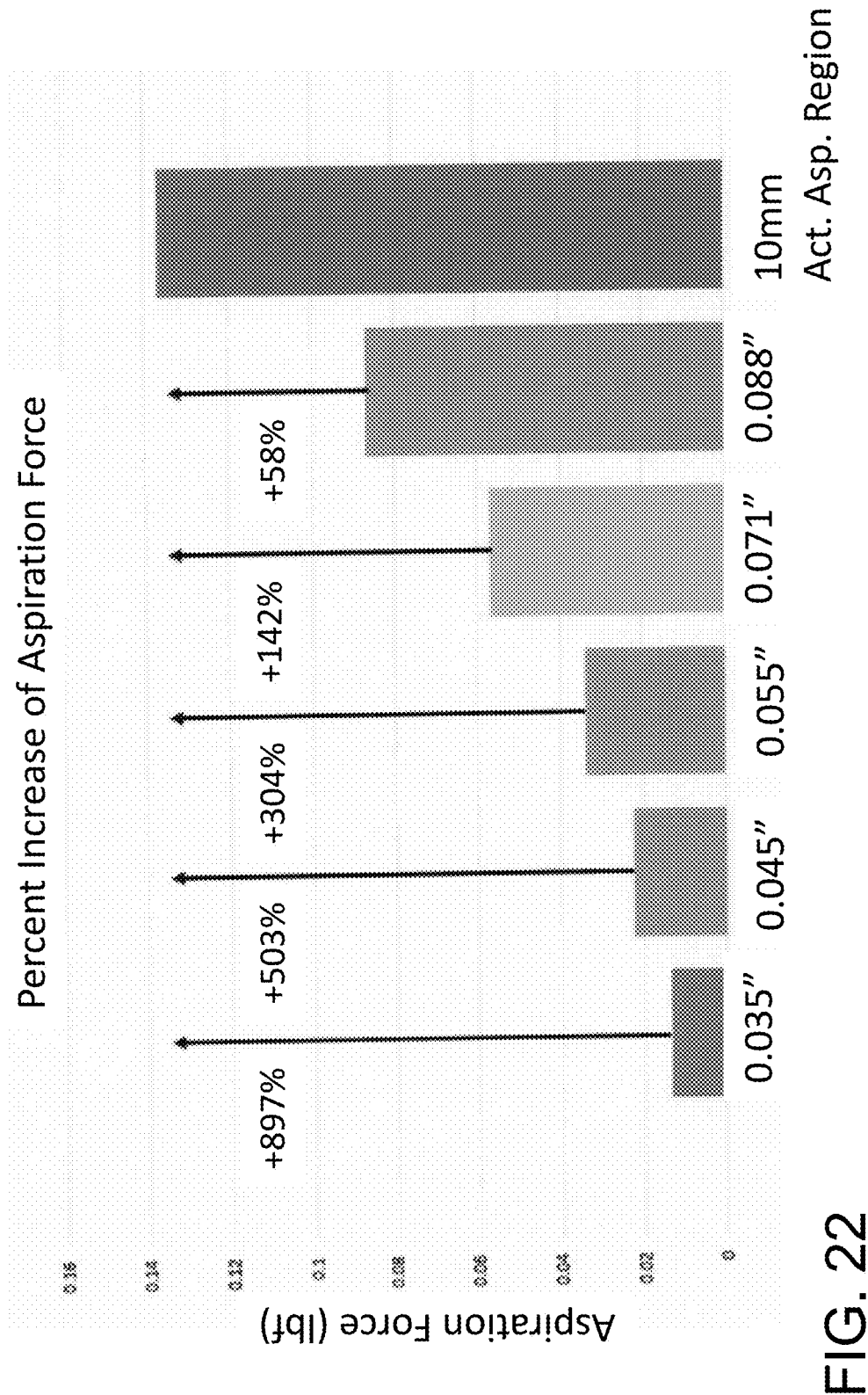
FIG. 22 depicts a graph of aspiration force and percent increase in aspiration force using a three-dimensional aspiration device as compared to conventional aspiration catheters.
Figure 23:
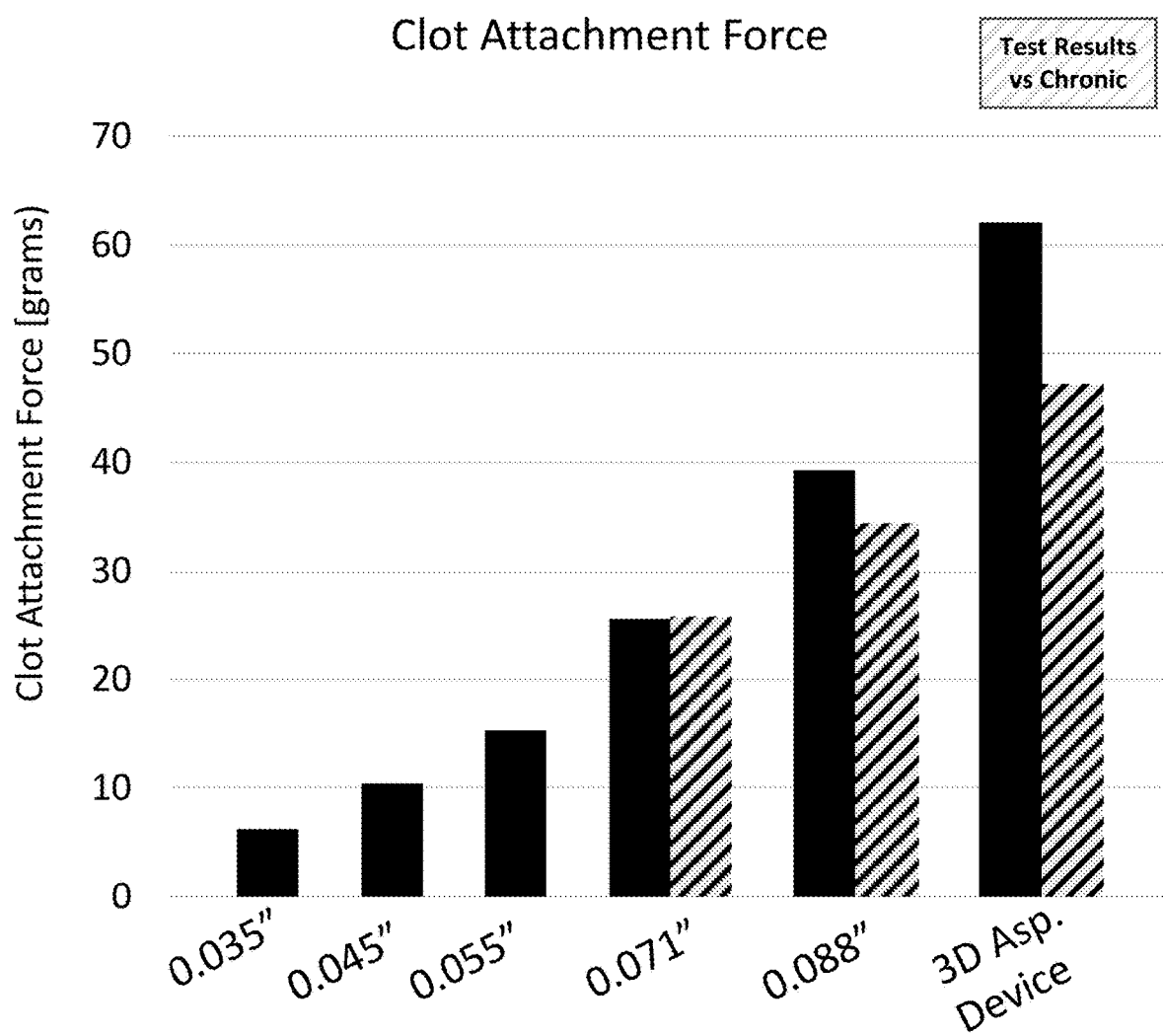
FIG. 23 depicts a graph of clot attachment force shown as projected force (solid bars) vs. actual test force (hashed bars) for convention catheters compared to a three-dimensional aspiration device.

A three-dimensional aspiration device offers several advantages, as shown in FIGS. 22-24. When a 10 mm active aspiration region of a three-dimensional aspiration device (with an outer diameter of 0.023 inches and an 18% open area) was compared to conventional aspiration catheters of varying inner diameters (0.035 inches to 0.088 inches), the three-dimensional aspiration device outperformed conventional aspiration catheter based on measured aspiration force (lbF), as shown in FIG. 22. Aspiration force was measured by using a vacuum pressure gauge while the catheter was attached to a standard aspiration pump. Force was then calculated. As shown in FIG. 22, the percent increase in aspiration force over conventional aspiration catheters ranged from about or substantially 50% to 900%. Another advantage of a three-dimensional aspiration device is that a length or an open area percentage of the active aspiration region can be adjusted for various clot lengths, desired aspiration force, etc. For example, a three-dimensional aspiration device may include a sleeve extending around at least a portion of a perimeter (outer diameter) of the active aspiration region. Alternatively, a sleeve may extend around at least a portion of an inner diameter of the active aspiration region. The sleeve may be slidably engaged with the active region to adjustably control a number of exposed apertures of the plurality of apertures.

Further, as shown in FIG. 23, clot attachment force was increased when a three-dimensional aspiration device was used as compared to conventional aspiration catheters. The solid bars in FIG. 23 represent projected or modeled clot attachment force (in grams) and the hashed bars represent test data. Briefly, clots were formed in tubes and a constant vacuum force was applied to a first end of the clot while a test device with vacuum force applied therethrough was applied to the opposite end of the clot. The test was run for one minute. As shown in FIG. 23, clot attachment force projected versus test data were highly similar for the conventional catheters having an outer diameter of 0.071 inches and 0.088 inches and for the tested three-dimensional aspiration device (10 mm active aspiration area; 18% open area). The three-dimensional aspiration device had improved and increased clot attachment force as compared to the conventional aspiration catheters having an outer diameter of 0.071 inches and 0.088 inches.

To achieve equivalent aspiration as conventional aspiration catheters of varying inner diameters, a segment length of an active aspiration region was determined. As shown in FIG. 24, an active aspiration region of 1 mm is about or substantially equivalent to a 0.035 inch inner diameter catheter; an active aspiration region of 1.3 mm is about or substantially equivalent to a 0.040 inch inner diameter catheter; an active aspiration region of 2.5 mm is about or substantially equivalent to a 0.055 inch inner diameter catheter; an active aspiration region of 4.2 mm is about or substantially equivalent to a 0.071 inch inner diameter catheter; and an active aspiration region of 6.5 mm is about or substantially equivalent to a 0.088 inch inner diameter catheter.

Although the present invention has been described in terms of certain preferred embodiments, it may be incorporated into other embodiments by persons of skill in the art in view of the disclosure herein. The scope of the invention is, therefore, not intended to be limited by the specific embodiments disclosed herein, but is intended to be defined by the full scope of the following claims.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of making a flexible distal zone on a neurovascular catheter, having an elongate tubular body with a distal end, comprising:
    dip coating a removable mandrel to form a tubular inner liner on the mandrel;
    softening a portion of the tubular inner liner on the mandrel, softening comprising applying tension axially to the portion of the tubular inner liner such that the tubular inner liner comprises a stretched portion and an unstretched portion after softening the portion of the tubular inner liner;
    applying a helical coil to an outside of the inner liner;
    positioning a plurality of tubular segments over the helical coil, the plurality of segments having durometers that decrease in a distal direction;
    heating the tubular segments to form the flexible distal zone on the neurovascular catheter; and
    removing the mandrel.

2. The method of claim 1, wherein the softened portion of the tubular inner liner comprises a distal 15 mm to 20 mm of the tubular inner liner.

3. The method of claim 1, further comprising achieving a thickness of the softened portion of the tubular inner liner of 0.00025 inches to 0.00075 inches.

4. The method of claim 1, further comprising aligning one or more polymer chains of the stretched portion of the tubular inner liner relative to one another in a similar or substantially similar direction as the applied tension.

5. The method of claim 1, further comprising coating the tubular inner liner with a tie layer.

6. The method as in claim 5, wherein the tie layer comprises polyurethane.

7. The method as in claim 5, wherein the tie layer has a wall thickness of no more than 0.005 inches.

8. The method as in claim 5, wherein the tie layer extends along at least a most distal 20 cm of the neurovascular catheter.

9. The method as in claim 5, further comprising positioning at least one axially extending tensile strength enhancing filament over the tie layer.

10. The method as in claim 9, further comprising overlapping the softened portion of the tubular inner liner with the at least one axially extending filament.

11. The method of claim 9, wherein the at least one axially extending filament includes an anchoring section, such that the method further comprises anchoring the at least one axially extending filament in a section of the catheter that includes the helical coil.

12. The method as in claim 9, wherein the filament extends along at least a most distal 15 cm of a length of the catheter.

13. The method as in claim 9, wherein the filament extends along at least a most distal 20 cm of a length of the catheter.

14. The method as in claim 9, wherein the filament comprises multiple fibers.

15. The method of claim 1, wherein the plurality of tubular segments form a proximal section having a proximal end and a distal end and a durometer equal to or greater than 65D at all points along a length from the proximal end to the distal end of the proximal section, a distal section having a proximal end and a distal end and a durometer equal to or less than 35D at all points along a length extending from the proximal end to the distal end of the distal section, and a transition section extending from the distal end of the proximal section to the proximal end of the distal section, the transition section comprising at least two tubular segments of the plurality of tubular segments and having a durometer less than 65D and greater than 35D at all points along a length extending from the distal end of the proximal section to the proximal end of the distal section, the transition section being shorter in length than the proximal section and shorter in length than the distal section.

16. The method as in claim 15, wherein the transition section comprises at least three tubular segments of the plurality of tubular segments.

17. The method as in claim 15, wherein the distal section is at least twice as long as the transition section.

18. The method as in claim 1, wherein removing the mandrel step includes axially elongating the mandrel.

19. The method as in claim 1, wherein positioning segments on the helical coil comprises positioning at least seven tubular segments of the plurality of tubular segments on the helical coil.

20. The method as in claim 1, wherein positioning segments on the helical coil comprises positioning at least nine tubular segments of the plurality of tubular segments on the helical coil.

21. The method as in claim 1, wherein the tubular inner liner comprises PTFE.

22. The method as in claim 1, wherein the coil comprises a shape memory material.

23. The method as in claim 22, wherein the coil comprises Nitinol.

24. The method as in claim 23, wherein the Nitinol comprises an Austenite state at body temperature.

25. The method as in claim 1, wherein the stretched portion is on a distal portion of the tubular inner liner.

26. The method as in claim 1, wherein softening the portion of the inner liner comprises stretching the portion of the tubular inner liner 50% to 90% of a pre-stretch length.

* * * * *